United States Patent
Weitzner et al.

(10) Patent No.: US 9,533,122 B2
(45) Date of Patent: Jan. 3, 2017

(54) CATHETER DRIVE SYSTEM WITH CONTROL HANDLE ROTATABLE ABOUT TWO AXES SEPARATED FROM HOUSING BY SHAFT

(75) Inventors: Barry Weitzner, Acton, MA (US);
Paul Smith, Smithfield, RI (US);
Michael Barenboym, Framingham, MA (US); Gary Kappel, Acton, MA (US);
John Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 341 days.

(21) Appl. No.: 12/008,502

(22) Filed: Jan. 11, 2008

(65) Prior Publication Data
US 2008/0287862 A1    Nov. 20, 2008

Related U.S. Application Data

(60) Provisional application No. 60/938,924, filed on May 18, 2007.

(51) Int. Cl.
*A61B 34/00* (2016.01)
*A61M 25/01* (2006.01)
*A61B 17/00* (2006.01)

(52) U.S. Cl.
CPC .......... *A61M 25/0136* (2013.01); *A61B 34/70* (2016.02); *A61B 34/71* (2016.02);
(Continued)

(58) Field of Classification Search
CPC ... A61B 17/062; A61B 1/0055; A61B 1/0052; A61B 34/70; A61B 34/71; A61B 34/74; A61M 25/0138; A61M 25/0147; A61M 25/0122; A61M 25/0116; A61M 25/0158; A61M 25/0136
(Continued)

(56) References Cited

U.S. PATENT DOCUMENTS 3,485,234 A    12/1969    Stevens
3,605,725 A     9/1971    Bentov
(Continued)

FOREIGN PATENT DOCUMENTS

EP    0640319 A1    1/1995
EP    1582138 A2    9/2008
(Continued)

OTHER PUBLICATIONS

International Search Report and Written Opinion for Application No. PCT/US2008/050923 mailed Sep. 10, 2008.
(Continued)

*Primary Examiner* — Bhisma Mehta
*Assistant Examiner* — Matthew A Engel
(74) *Attorney, Agent, or Firm* — Bookoff McAndrews, PLLC

(57) ABSTRACT

Drive systems and methods of use are disclosed herein for performing medical procedures on a patient. The drive systems include various handle types and triggers for controlling catheters and end effectors. The various handle types include a flexible handle and ambidextrous handles that can alter the handedness of the handle for particularized use. The handles drive articulation sections of the catheter and end effectors with various degrees of freedom, and include locks for holding the catheter and/or end effector in place. The catheter systems include structures for allowing degrees of freedom, such as notches, mechanical interlocks, and articulation joints. In addition, the catheters articulate via cables or fluids.

9 Claims, 49 Drawing Sheets

(52) U.S. Cl.
CPC ........ *A61B 34/74* (2016.02); *A61B 2017/003* (2013.01); *A61B 2017/00446* (2013.01); *A61B 2034/301* (2016.02); *A61B 2034/715* (2016.02)

(58) Field of Classification Search
USPC ........... 604/95.01, 95.04, 528; 600/141, 142, 600/146, 147, 148, 149, 150
See application file for complete search history.

(56) References Cited

U.S. PATENT DOCUMENTS

| | | | |
|---|---|---|---|
| 3,949,757 A | 4/1976 | Sabel | |
| 4,499,895 A | 2/1985 | Takayama | |
| 4,503,842 A | 3/1985 | Takayama | |
| 4,539,976 A | 9/1985 | Sharpe | |
| 4,688,555 A * | 8/1987 | Wardle | 600/149 |
| 4,696,544 A | 9/1987 | Costella | |
| 4,826,087 A | 5/1989 | Chinery | |
| 4,854,301 A | 8/1989 | Nakajima | |
| 5,007,406 A | 4/1991 | Takahashi et al. | |
| 5,025,778 A | 6/1991 | Silverstein et al. | |
| 5,120,323 A | 6/1992 | Shockey et al. | |
| 5,159,446 A | 10/1992 | Hibino et al. | |
| 5,188,591 A | 2/1993 | Dorsey, III | |
| 5,234,443 A | 8/1993 | Phan et al. | |
| 5,250,054 A | 10/1993 | Li | |
| 5,254,088 A | 10/1993 | Lundquist et al. | |
| 5,271,381 A * | 12/1993 | Ailinger et al. | 600/128 |
| 5,284,130 A | 2/1994 | Ratliff | |
| 5,325,845 A * | 7/1994 | Adair | 600/114 |
| 5,383,852 A | 1/1995 | Stevens-Wright | |
| 5,395,367 A | 3/1995 | Wilk | |
| 5,402,793 A | 4/1995 | Gruner et al. | |
| 5,423,848 A | 6/1995 | Washizuka et al. | |
| 5,441,483 A * | 8/1995 | Avitall | A61B 18/1492 604/95.05 |
| 5,462,527 A | 10/1995 | Stevens-Wright et al. | |
| 5,477,856 A | 12/1995 | Lundquist | |
| 5,480,406 A | 1/1996 | Nolan et al. | |
| 5,501,654 A | 3/1996 | Failla et al. | |
| 5,575,755 A | 11/1996 | Krauter et al. | |
| 5,636,634 A | 6/1997 | Kordis | |
| 5,643,294 A | 7/1997 | Tovey et al. | |
| 5,681,331 A | 10/1997 | de la Torre et al. | |
| 5,749,828 A * | 5/1998 | Solomon et al. | 600/141 |
| 5,797,928 A | 8/1998 | Kogasaka | |
| 5,813,813 A | 9/1998 | Daum et al. | |
| 5,827,323 A | 10/1998 | Klieman et al. | |
| 5,916,146 A | 6/1999 | Benedetto et al. | |
| 5,931,849 A * | 8/1999 | Desvignes et al. | 606/167 |
| 5,976,121 A | 11/1999 | Matern et al. | |
| 5,984,939 A | 11/1999 | Yoon | |
| 6,001,114 A | 12/1999 | Ouchi | |
| 6,007,482 A | 12/1999 | Madni et al. | |
| 6,017,322 A | 1/2000 | Snoke et al. | |
| 6,059,719 A | 5/2000 | Yamamoto et al. | |
| 6,066,090 A | 5/2000 | Yoon | |
| 6,093,195 A | 7/2000 | Ouchi | |
| 6,126,665 A | 10/2000 | Yoon | |
| 6,143,006 A | 11/2000 | Chan | |
| 6,156,027 A | 12/2000 | West | |
| 6,270,508 B1 * | 8/2001 | Klieman et al. | 606/147 |
| 6,325,808 B1 | 12/2001 | Bernard et al. | |
| 6,352,503 B1 | 3/2002 | Matsui et al. | |
| 6,364,828 B1 * | 4/2002 | Yeung et al. | 600/142 |
| 6,451,027 B1 | 9/2002 | Cooper et al. | |
| 6,527,753 B2 | 3/2003 | Sekine et al. | |
| 6,638,268 B2 | 10/2003 | Niazi | |
| 6,648,816 B2 | 11/2003 | Irion et al. | |
| 6,656,111 B2 | 12/2003 | Fujii et al. | |
| 6,740,030 B2 | 5/2004 | Martone et al. | |
| 6,743,227 B2 | 6/2004 | Serraj et al. | |
| 6,755,812 B2 | 6/2004 | Peterson et al. | |
| 6,817,974 B2 | 11/2004 | Cooper et al. | |
| 6,833,912 B2 | 12/2004 | Lei et al. | |
| 6,837,849 B2 | 1/2005 | Ogura et al. | |
| 6,858,024 B1 | 2/2005 | Berg et al. | |
| 6,899,673 B2 | 5/2005 | Ogura et al. | |
| 6,899,973 B2 | 5/2005 | Nakanishi et al. | |
| 6,991,602 B2 | 1/2006 | Nakazawa et al. | |
| 7,029,435 B2 | 4/2006 | Nakao | |
| 7,090,683 B2 | 8/2006 | Brock et al. | |
| 7,153,314 B2 | 12/2006 | Laufer et al. | |
| 7,156,857 B2 | 1/2007 | Pasricha et al. | |
| 7,199,790 B2 | 4/2007 | Rosenberg et al. | |
| 7,537,550 B1 * | 5/2009 | Krull | 482/98 |
| 7,803,137 B2 | 9/2010 | Stefanchik et al. | |
| 7,833,156 B2 | 11/2010 | Williams et al. | |
| 7,871,371 B2 | 1/2011 | Komiya et al. | |
| 8,046,049 B2 | 10/2011 | Govari et al. | |
| 8,579,902 B2 | 11/2013 | Bleich et al. | |
| 2001/0049497 A1 | 12/2001 | Kalloo et al. | |
| 2002/0068868 A1 * | 6/2002 | Thompson et al. | 600/434 |
| 2002/0128633 A1 | 9/2002 | Brock et al. | |
| 2002/0138082 A1 | 9/2002 | Brock et al. | |
| 2002/0177750 A1 | 11/2002 | Pilvisto | |
| 2003/0004460 A1 * | 1/2003 | Bedell | 604/95.04 |
| 2003/0050649 A1 | 3/2003 | Brock et al. | |
| 2003/0092965 A1 | 5/2003 | Konomura et al. | |
| 2003/0135091 A1 | 7/2003 | Nakazawa et al. | |
| 2004/0019359 A1 | 1/2004 | Worley et al. | |
| 2004/0034365 A1 | 2/2004 | Lentz et al. | |
| 2004/0059191 A1 | 3/2004 | Krupa et al. | |
| 2004/0092794 A1 | 5/2004 | Chin et al. | |
| 2004/0138525 A1 | 7/2004 | Saadat et al. | |
| 2004/0138529 A1 | 7/2004 | Willshire et al. | |
| 2004/0176751 A1 | 9/2004 | Weitzner et al. | |
| 2004/0181140 A1 | 9/2004 | Falwell et al. | |
| 2004/0193016 A1 * | 9/2004 | Root | A61B 1/0052 600/146 |
| 2004/0236316 A1 * | 11/2004 | Danitz et al. | 606/1 |
| 2004/0260245 A1 | 12/2004 | Clem et al. | |
| 2005/0033355 A1 | 2/2005 | Frank et al. | |
| 2005/0054899 A1 | 3/2005 | Miyake | |
| 2005/0075538 A1 * | 4/2005 | Banik | A61B 1/00071 600/141 |
| 2005/0096694 A1 | 5/2005 | Lee | |
| 2005/0117118 A1 | 6/2005 | Miller et al. | |
| 2005/0119522 A1 | 6/2005 | Okada | |
| 2005/0165277 A1 | 7/2005 | Carrillo et al. | |
| 2005/0182292 A1 | 8/2005 | Suzuki | |
| 2005/0222495 A1 | 10/2005 | Okada et al. | |
| 2005/0228224 A1 | 10/2005 | Okada et al. | |
| 2005/0240078 A1 | 10/2005 | Kwon et al. | |
| 2005/0251091 A1 | 11/2005 | Saadat et al. | |
| 2005/0277945 A1 | 12/2005 | Saadat et al. | |
| 2005/0288549 A1 | 12/2005 | Mathis | |
| 2006/0020287 A1 | 1/2006 | Lee et al. | |
| 2006/0079873 A1 | 4/2006 | Scopton et al. | |
| 2006/0089626 A1 | 4/2006 | Vlegele et al. | |
| 2006/0155247 A1 | 7/2006 | Lampropoulos | |
| 2006/0178560 A1 | 8/2006 | Saadat et al. | |
| 2006/0178562 A1 | 8/2006 | Saadat et al. | |
| 2006/0206006 A1 | 9/2006 | Schara et al. | |
| 2006/0264705 A1 | 11/2006 | Adams et al. | |
| 2007/0010800 A1 | 1/2007 | Weitzner et al. | |
| 2007/0010801 A1 * | 1/2007 | Chen | A61B 10/06 606/1 |
| 2007/0021737 A1 * | 1/2007 | Lee | A61B 17/062 606/1 |
| 2007/0049435 A1 | 3/2007 | Jinno et al. | |
| 2007/0088340 A1 | 4/2007 | Brock et al. | |
| 2007/0100201 A1 | 5/2007 | Komiya et al. | |
| 2007/0100254 A1 | 5/2007 | Murakami et al. | |
| 2007/0129605 A1 | 6/2007 | Schaaf | |
| 2007/0135803 A1 | 6/2007 | Belson | |
| 2007/0156225 A1 | 7/2007 | George et al. | |
| 2007/0167679 A1 | 7/2007 | Miyamoto et al. | |
| 2007/0167680 A1 | 7/2007 | Miyamoto et al. | |
| 2007/0219411 A1 | 9/2007 | Dejima et al. | |
| 2007/0225562 A1 | 9/2007 | Spivey et al. | |
| 2007/0249896 A1 | 10/2007 | Goldfarb et al. | |
| 2007/0249897 A1 | 10/2007 | Miyamoto et al. | |
| 2007/0255100 A1 | 11/2007 | Barlow et al. | |

(56) References Cited

U.S. PATENT DOCUMENTS

| | | |
|---|---|---|
| 2007/0255291 A1 | 11/2007 | Brock et al. |
| 2007/0270752 A1 | 11/2007 | LaBombard |
| 2007/0282371 A1 | 12/2007 | Lee et al. |
| 2007/0287992 A1 | 12/2007 | Diolaiti et al. |
| 2008/0045803 A1 | 2/2008 | Williams et al. |
| 2008/0051629 A1 | 2/2008 | Sugiyama et al. |
| 2008/0051631 A1 | 2/2008 | Dejima et al. |
| 2008/0172038 A1* | 7/2008 | Dollar et al. ............... 604/528 |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0221391 A1 | 9/2008 | Weitzner et al. |
| 2008/0243176 A1 | 10/2008 | Weitzner et al. |
| 2008/0287862 A1 | 11/2008 | Weitzner et al. |
| 2012/0165829 A1 | 6/2012 | Chen et al. |

FOREIGN PATENT DOCUMENTS

| | | |
|---|---|---|
| JP | 08-224241 | 9/1996 |
| JP | 10-118072 | 5/1998 |
| JP | 10-262983 | 10/1998 |
| JP | 11-099124 | 4/1999 |
| JP | 11-276489 | 10/1999 |
| JP | 2001-104315 | 4/2001 |
| JP | 2001-277177 | 10/2001 |
| JP | 2002-287613 | 10/2002 |
| JP | 2002-291765 | 10/2002 |
| JP | 2003-111769 | 4/2003 |
| JP | 2004-173963 | 6/2004 |
| JP | 2004-180781 | 7/2004 |
| JP | 2005-103140 | 4/2005 |
| JP | 2005-296412 | 10/2005 |
| JP | 2009-537233 | 10/2009 |
| WO | WO 94/21179 | 9/1994 |
| WO | WO 97/12557 | 4/1997 |
| WO | WO 97/32528 | 9/1997 |
| WO | WO 02/07611 A2 | 1/2002 |
| WO | WO 2007/033379 A2 | 3/2007 |
| WO | WO 2008/070556 A1 | 6/2008 |

OTHER PUBLICATIONS

English translation of JP 08-224241 (15 pages).
English abstract of JP 10-262983 (2 pages).
English abstract of JP 11-099124 (2 pages).
English abstract of JP 2001-277177 (2 pages).
English abstract of JP 2002-287613 (2 pages).
English abstract of JP 2002-291765 (2 pages).
English abstract of JP 2004-180781 (2 pages).
English abstract of JP 2003-111769 (1 page), Published Apr. 15, 2003.
English abstract of JP 2004-173963 (1 page), Published Jun. 24, 2004.
English translation of JP 2005-103140 (40 pages), Published Apr. 21, 2005.
English abstract of JP 2005-296412 (1 page), Published Oct. 27, 2005.

\* cited by examiner

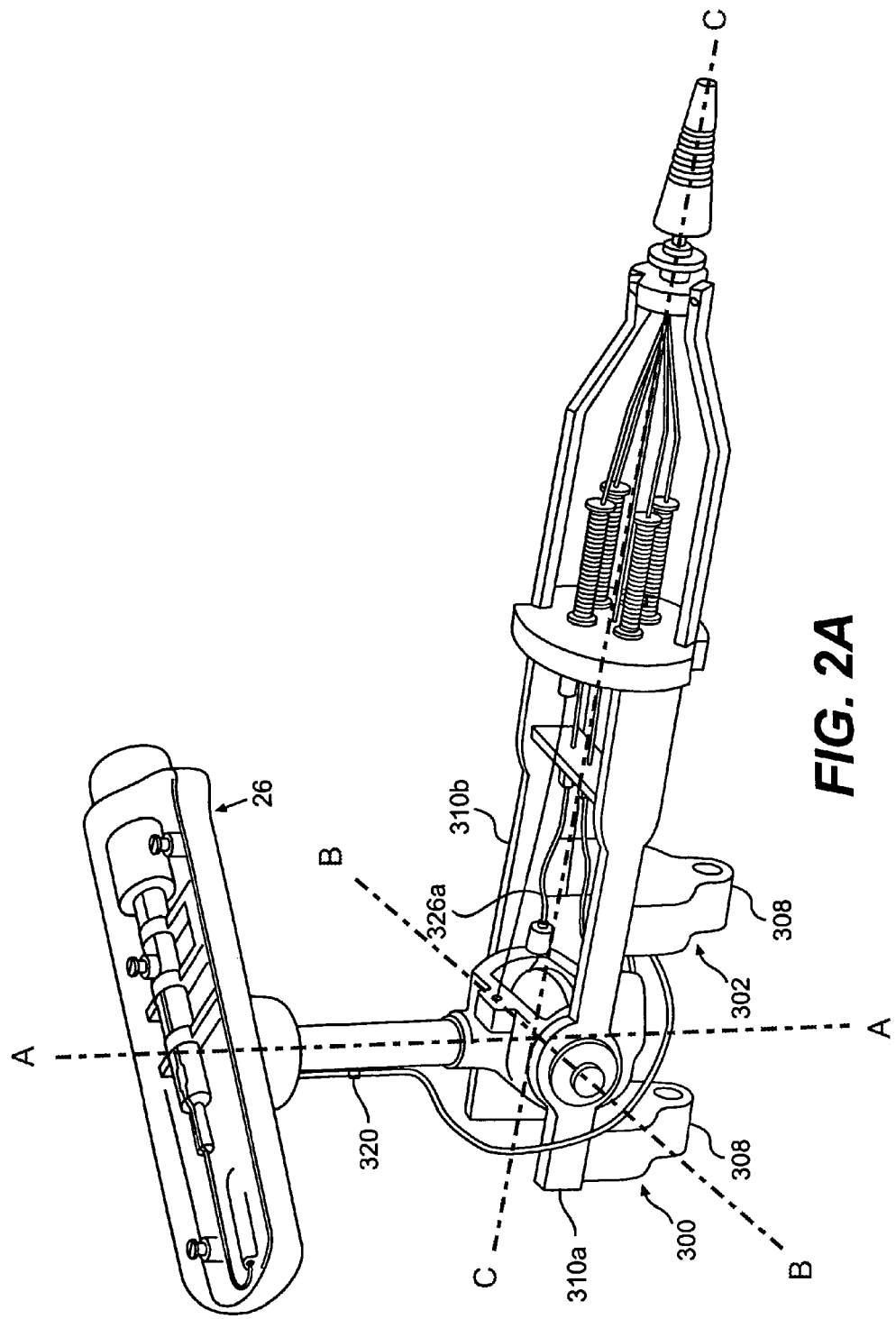

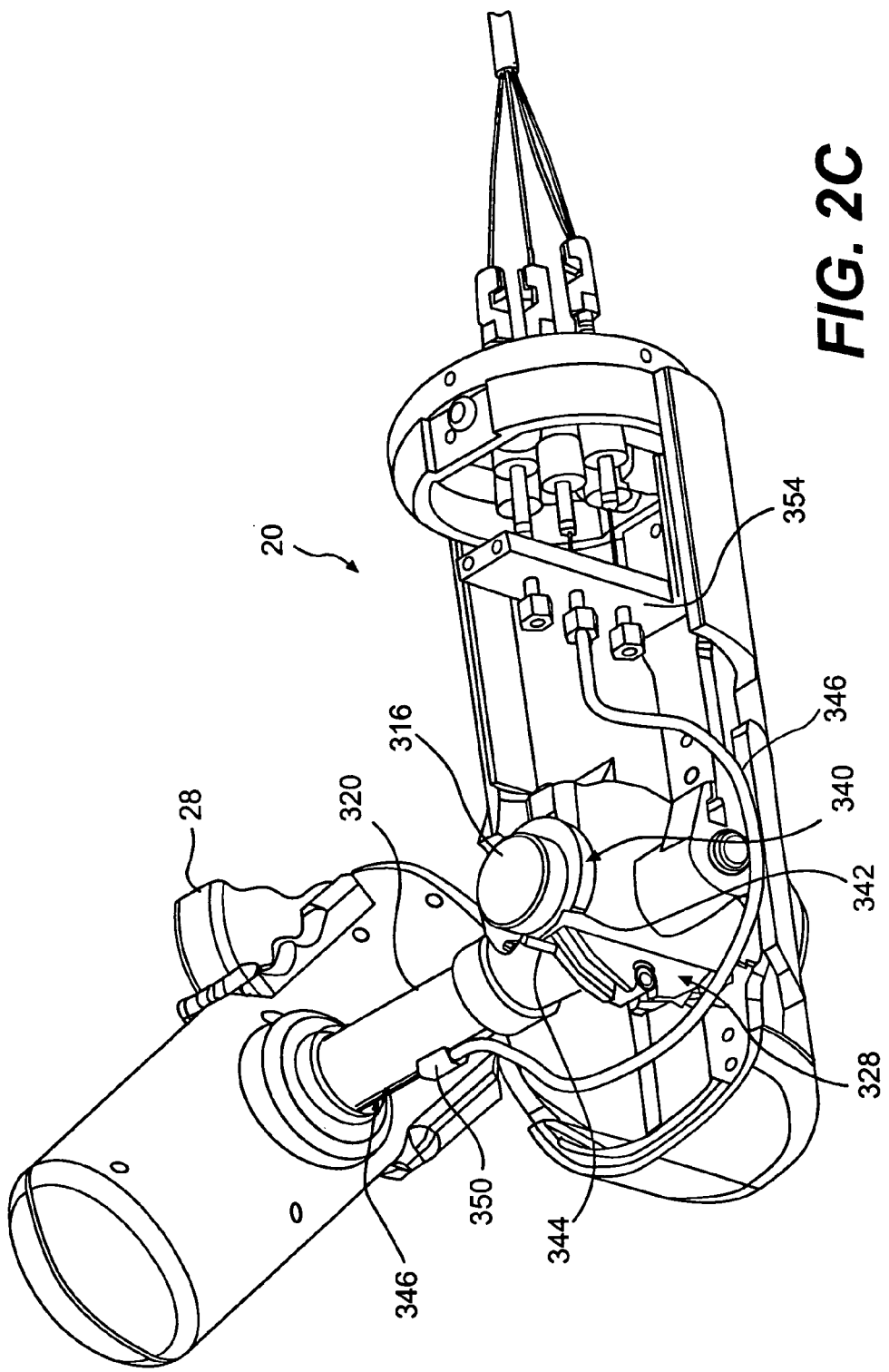

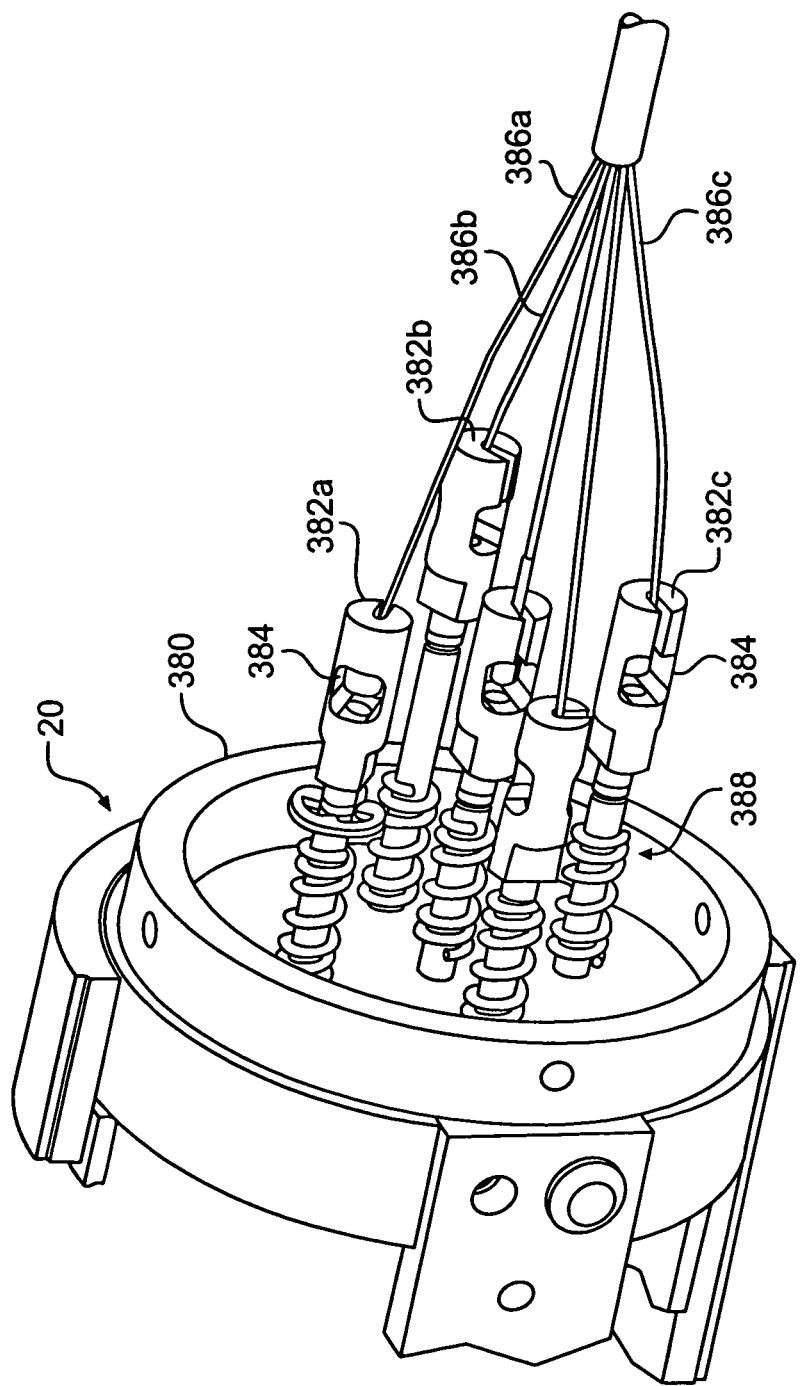

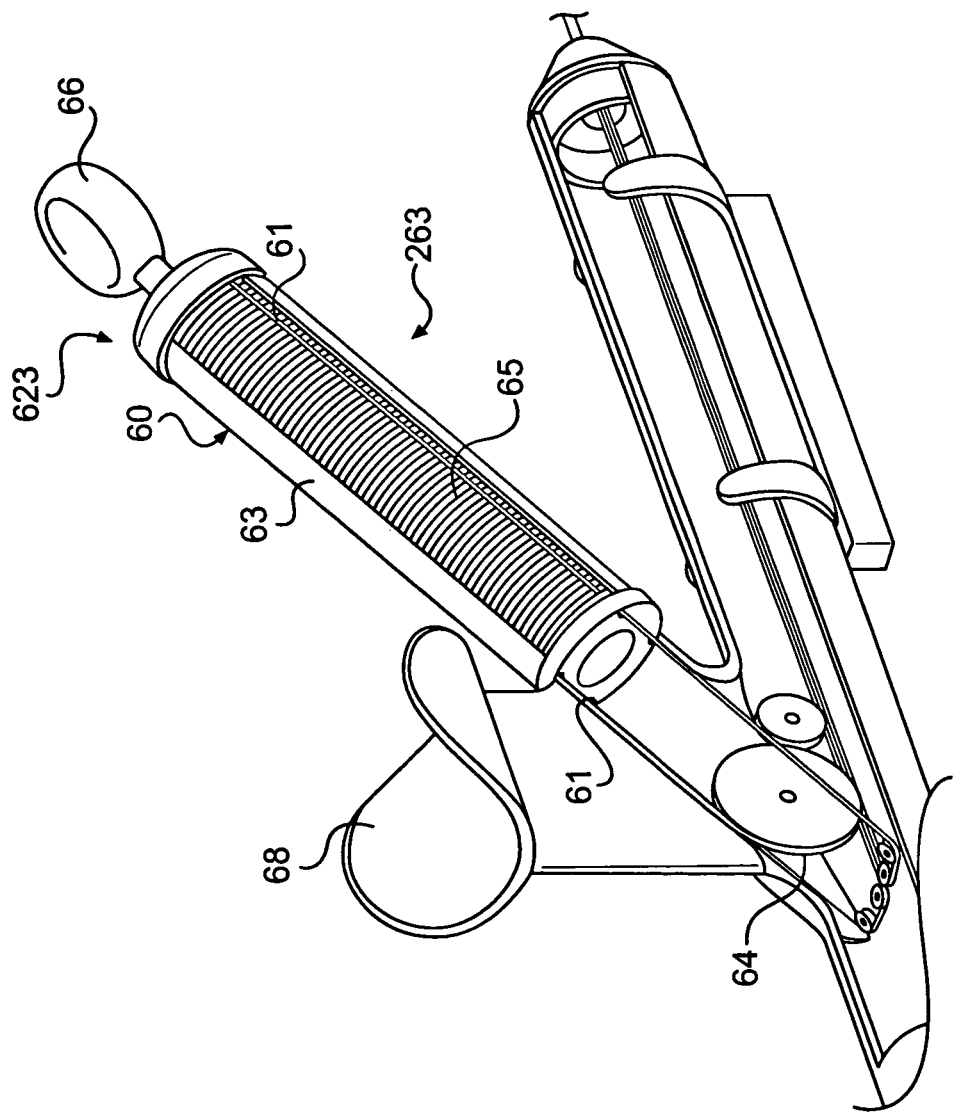

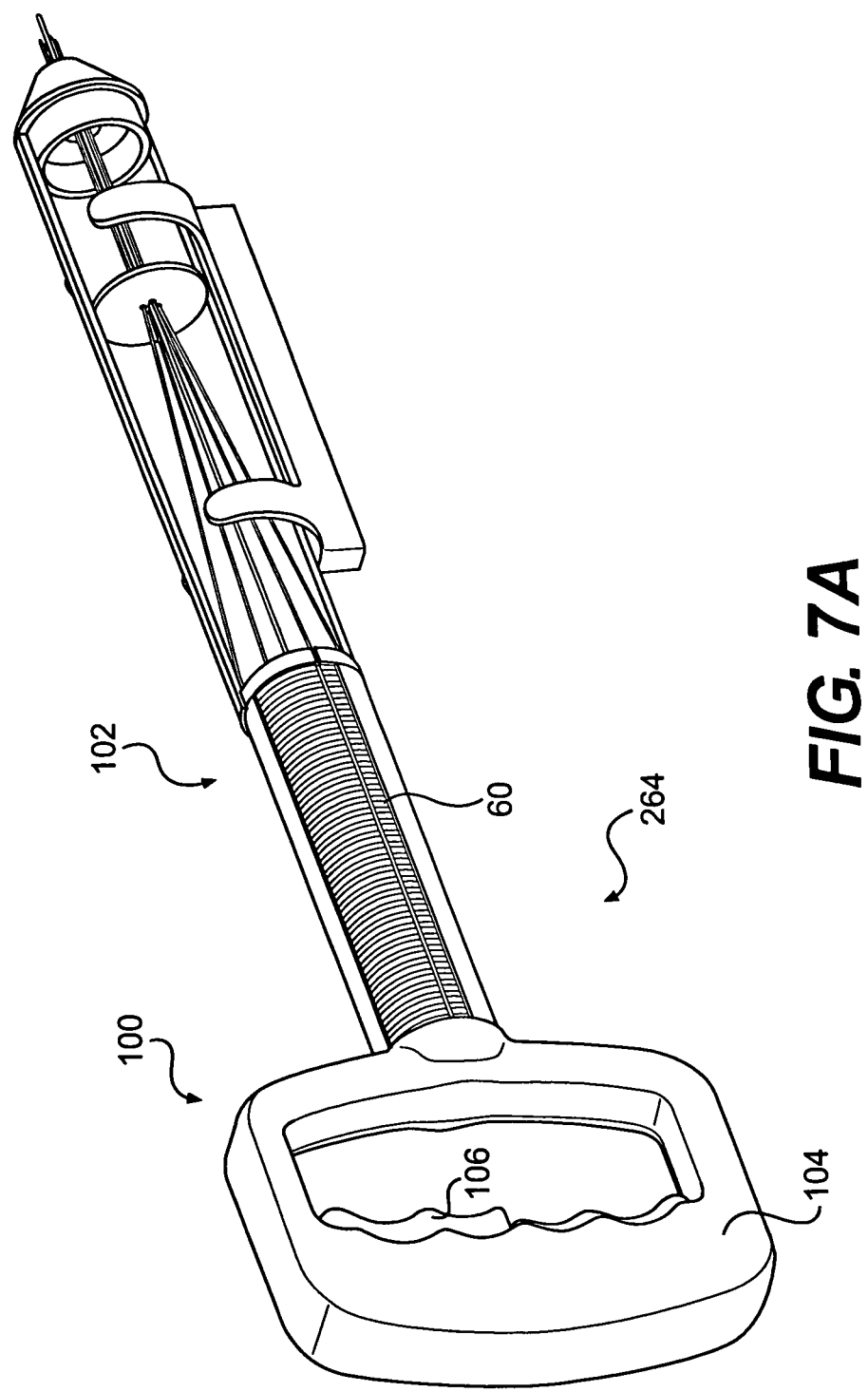

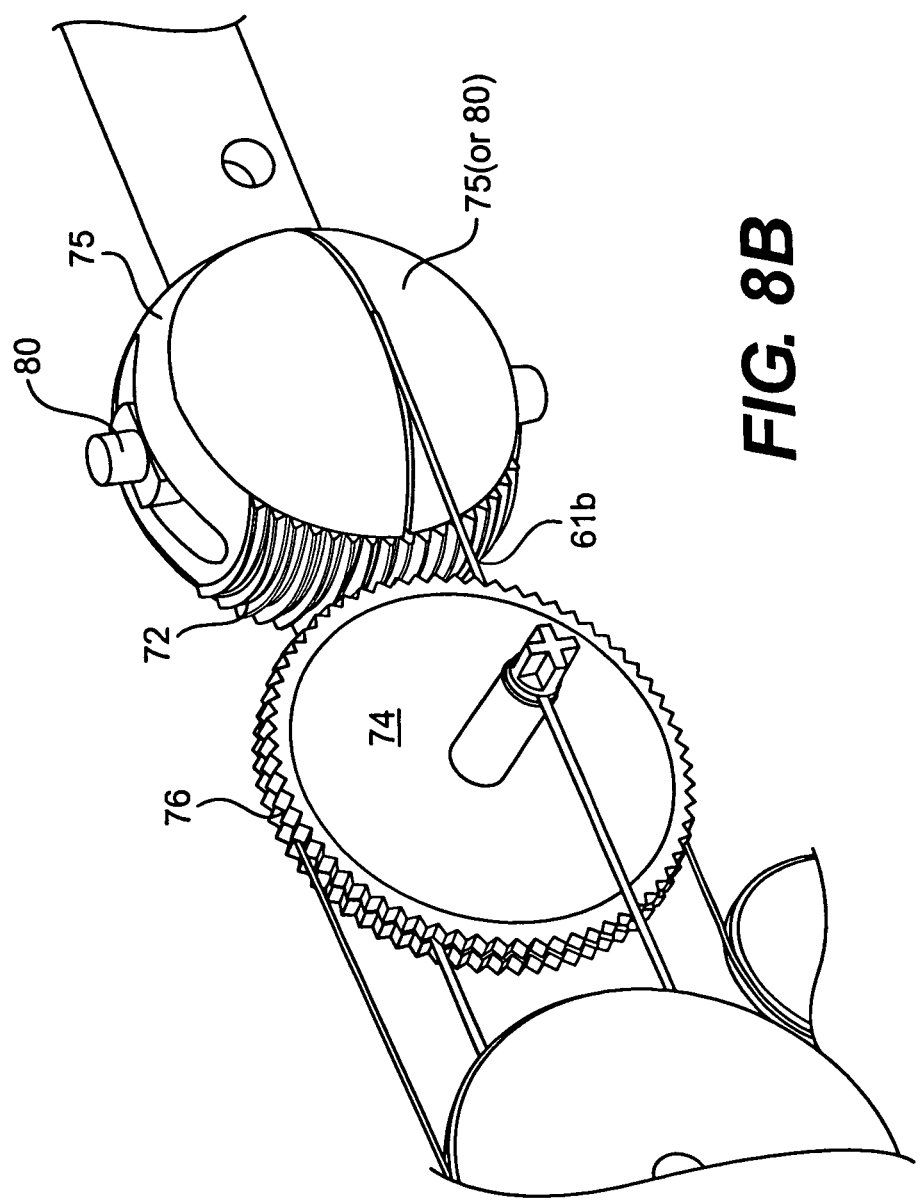

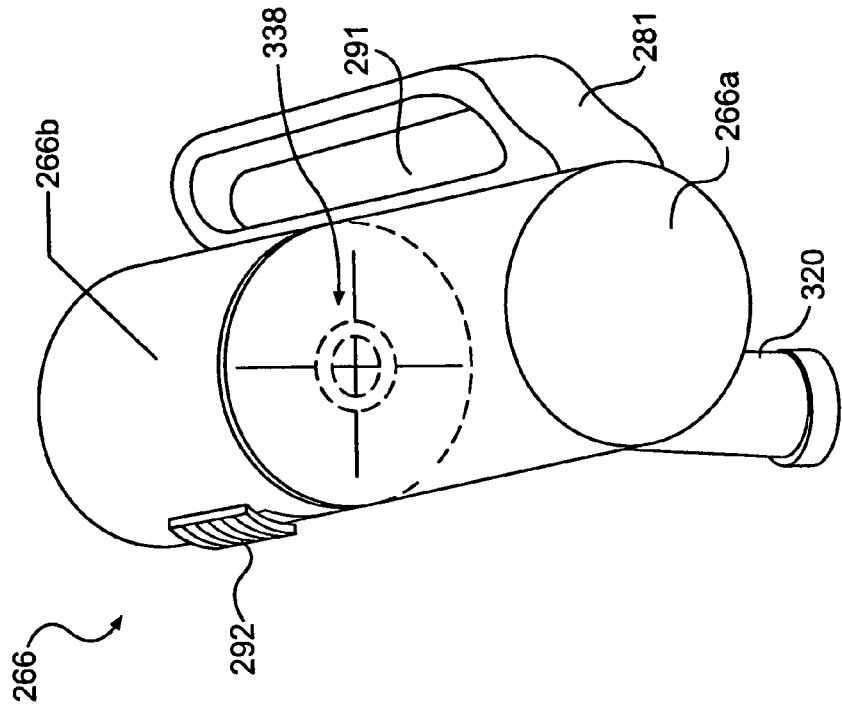
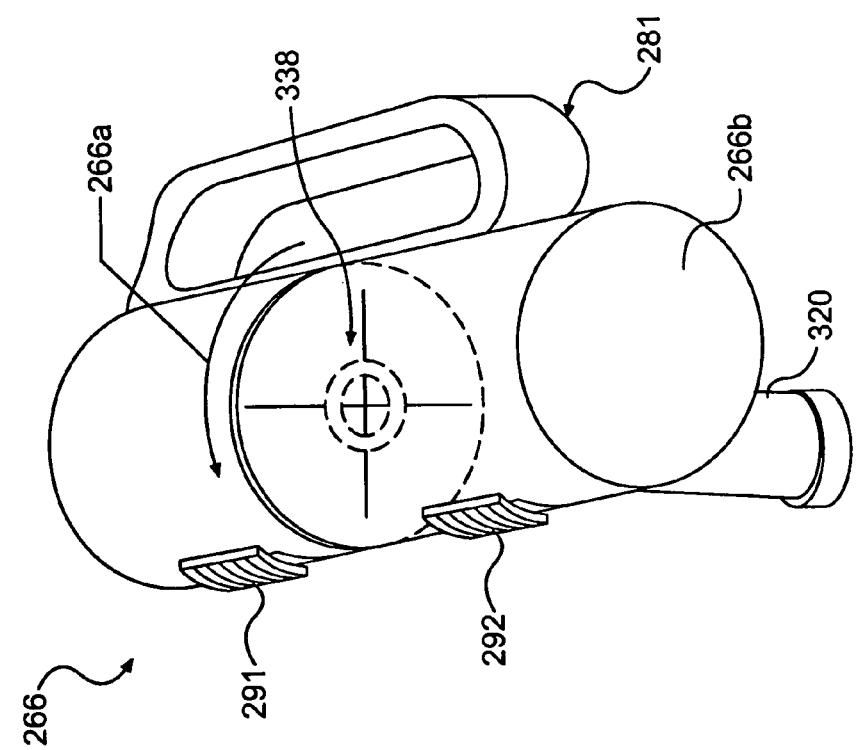

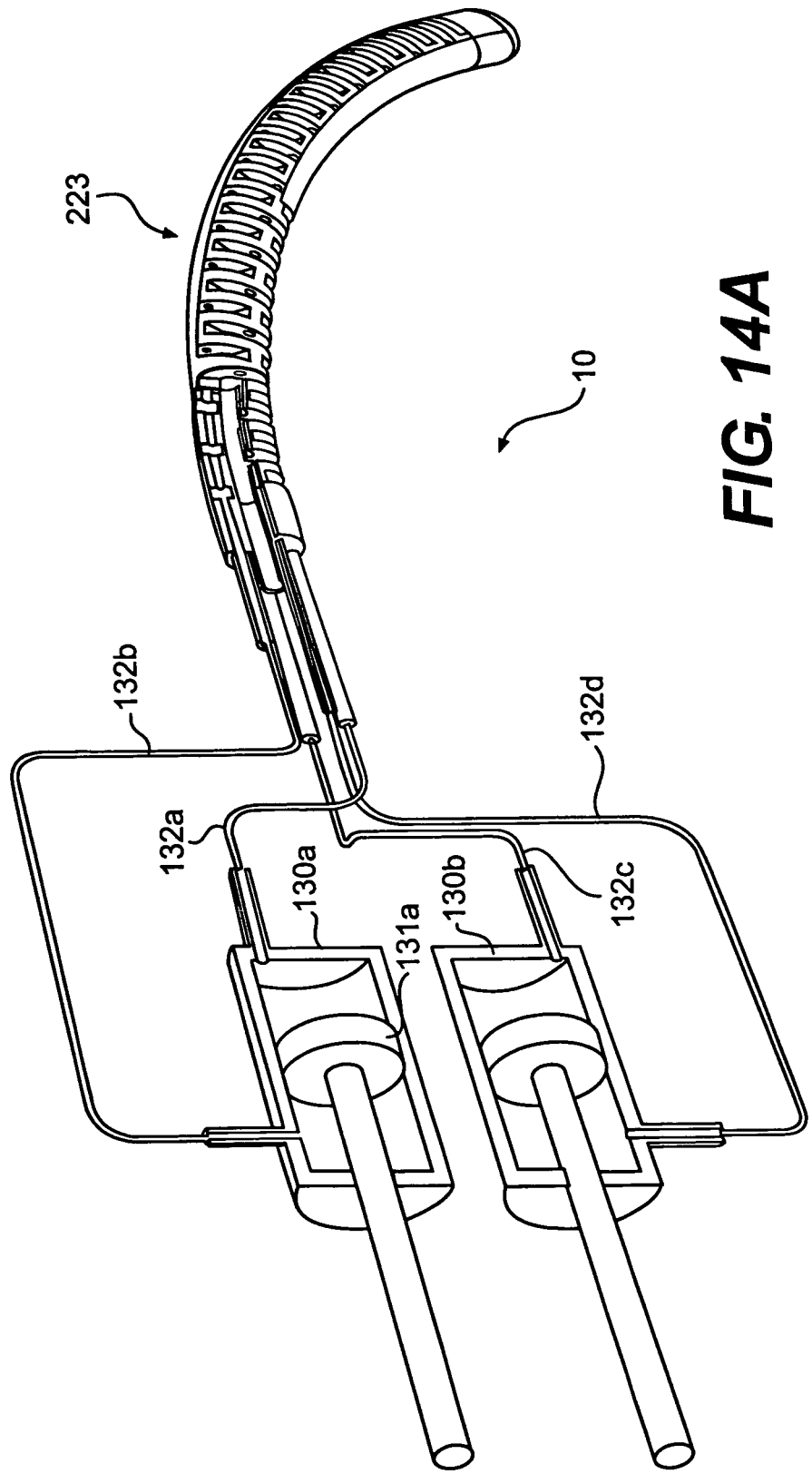

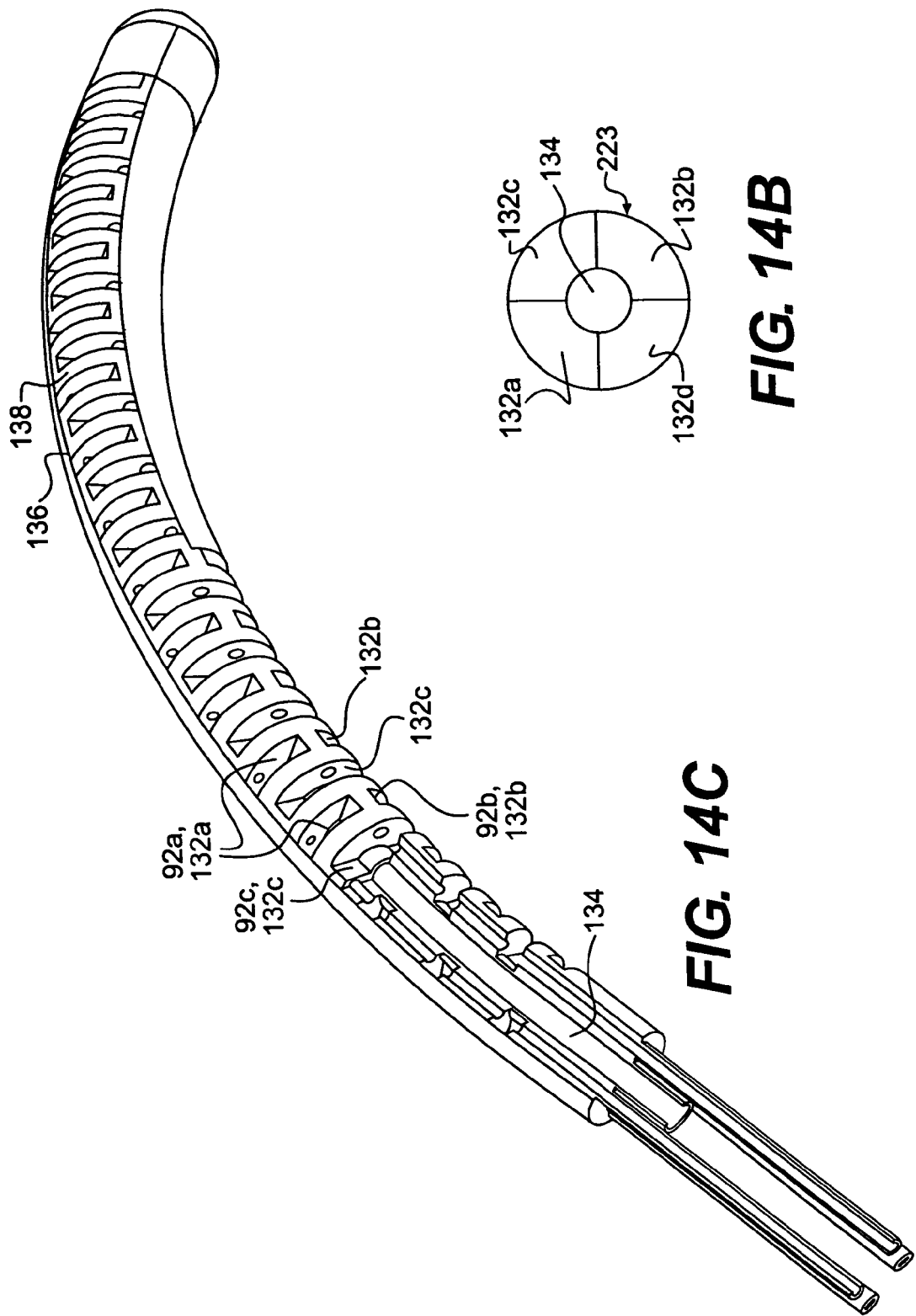

CATHETER DRIVE SYSTEM WITH CONTROL HANDLE ROTATABLE ABOUT TWO AXES SEPARATED FROM HOUSING BY SHAFT

CROSS-REFERENCE TO RELATED APPLICATIONS

This application claims priority to Provisional Application No. 60/938,924 entitled "Drive Systems and Methods of Use," filed May 18, 2007.

BACKGROUND OF THE INVENTION

Conventional surgical tools, such as endoscopic and laparoscopic devices, can provide surgical access to surgical sites while minimizing patient trauma. Although the growing capabilities of such therapeutic devices allow users to perform an increasing variety of surgeries through traditional minimally invasive routes, further refinements may allow surgical access through even less invasive routes and/or facilitate conventional surgical procedures. Currently some robotic systems have been proposed to allow surgical access via a natural orifice. The user interface is remote from surgical tools and/or end effectors. Unfortunately, these systems are generally expensive and complicated. In addition, they fail to provide the tactile user feedback that traditional devices can provide.

Accordingly, there is room for further refinement to surgical devices and a need to develop new surgical systems.

SUMMARY

An embodiment includes a tool for use in performing medical procedures on a patient. The tool can include various novel handle types and triggers for controlling a catheter and/or end effector. In one embodiment, a control member (or control handle) allows a user to control one, two, three, four, five, six, or more than six degrees of freedom. The control handle controls degrees of freedom via a bendable shaft in one embodiment.

The handle also provides for ambidextrous use in an embodiment. The user can change the handedness of the handle and/or stand the handle on its end in a joystick configuration for a particularized use. These handles can also change orientation in other ways. By manipulating handle orientation, a user can more easily articulate a catheter and/or actuate an end effector.

In one embodiment, catheter articulation is accomplished by creating tension along cables via a spring-loaded pin, while, in another embodiment, the spring-loaded pin is absent. In still another embodiment, fluid pathways, instead of cables, articulate the articulation section of a catheter. The articulation section can lock into a particular position or shape in at least one embodiment.

The articulation section of a catheter can include notches to allow articulation. In another embodiment, the articulation section includes ball sockets. In still another embodiment, articulation joints facilitate the catheter articulation.

Additional objects and advantages of the embodiments will be set forth in part in the description which follows, and in part will be obvious from the description, or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the embodiments, as claimed.

The accompanying drawings, which are incorporated in and constitute a part of this specification, illustrate several embodiments and together with the description, serve to explain the principles of the embodiments.

BRIEF DESCRIPTION OF THE DRAWINGS

The accompanying drawings, which are incorporated in and constitute a part of this specification, illustrate several embodiments and together with the description, serve to explain the principles of the embodiments.

FIG. 2A is an exemplary illustration of inner components of a tool, in accordance with an embodiment.

FIGS. 2C and 2D are exemplary illustrations of a trunnion within a control member, in accordance with an embodiment.

FIGS. 2J and 2K are exemplary illustrations of a "firewall" coupling mechanism for coupling the control member to one or more control cables.

FIGS. 6A and 6B are exemplary illustrations of a handle with a flexible shaft, in accordance with an embodiment.

FIGS. 7A through 7C are exemplary illustrations of another handle with a flexible shaft, incorporating a grip, in accordance with an embodiment FIGS. 8A through 8D are exemplary illustrations of gears that permit a user to control degrees of freedom, in accordance with an embodiment.

FIGS. 9D and 9E are exemplary illustrations of an ambidextrous control handle with a split grip being changed from right-handedness to left-handedness by rotating the grip portions, in accordance with an embodiment.

FIGS. 14A through 14E are exemplary illustrations of a tool including hydraulic control of the catheter, in accordance with an embodiment.

DESCRIPTION OF THE EMBODIMENTS

Described below are exemplary embodiments of tools that allow a user to perform a procedure, such as a surgical procedure, at a distance. In one aspect, a tool generally includes a proximal user interface (referred to herein as a control member or handle), an elongate catheter body, and a distal end. The proximal control member can control movement of the catheter and/or an end effector positioned proximate to the distal end of the tool. The tools described herein permit control of one, two, three, four, five, six, or more than six degrees of freedom via the handle and/or control member.

In one embodiment, user input forces upon the handle can control movement of the handle relative to the control member and/or can control movement of the (entire) tool relative to a reference point (e.g., relative to a patient). For example, movement of the handle can control articulation of a catheter articulation section and/or actuation of an end effector. In one aspect, movement of the handle can drive one, two, three, or more than three degrees of freedom of the catheter and/or end effector. In another aspect, moving the control member (e.g., rotational and/or longitudinal movement relative to a point of reference) can control one, two, or more than two degrees of freedom.

The tools described herein can be used with a variety of surgical or non-surgical system, including, for example, those described in U.S. patent application Ser. Nos. 11/946,779; 11/946,790; 11/946,799; 11/946,807; 11/946,812; and 11/946,818, which are incorporated herein by reference.

While the discussion of devices, systems, and methods below may generally refer to "surgical tools," "surgery," or a "surgical site" for convenience, the described devices, systems, and their methods of use are not limited to tissue resection and/or repair procedures. In particular, the described systems can be used for inspection and diagnosis in addition, or as an alternative, to surgery.

Figure 1:
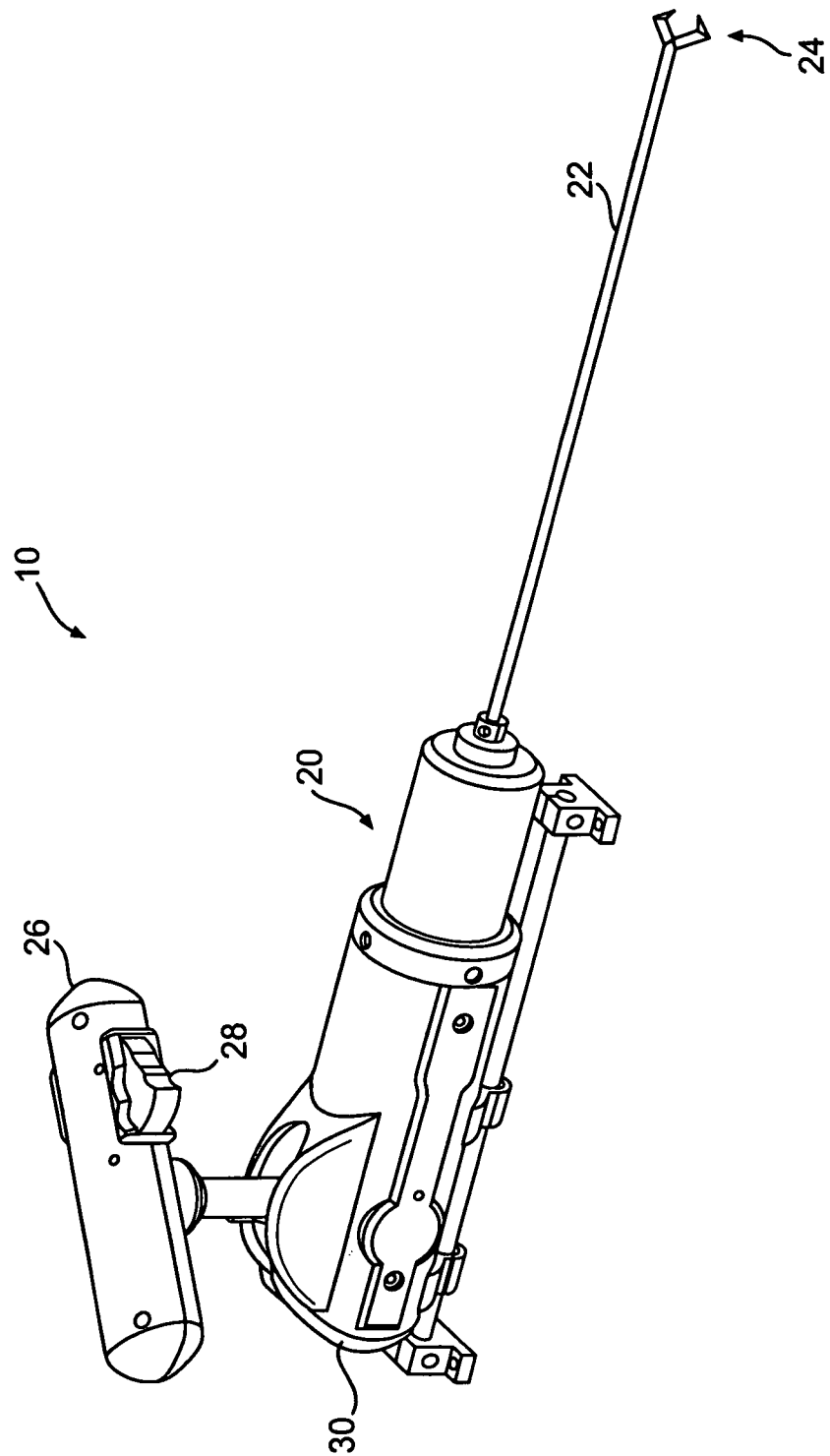
FIG. 1 is an exemplary perspective view of a tool comprising a control member, catheter, and end effector, in accordance with an embodiment.
Figure 1A:
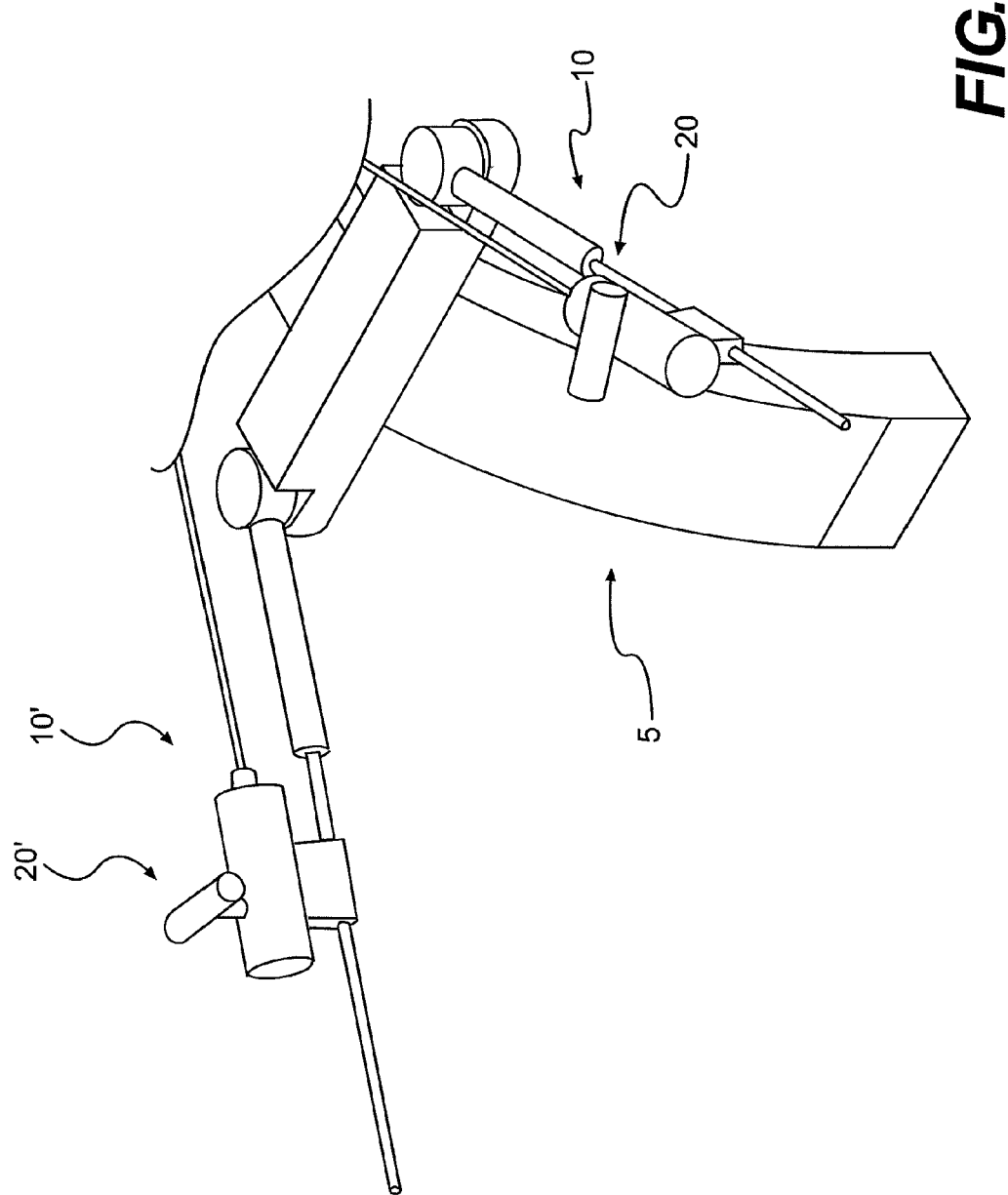
FIG. 1A is an exemplary perspective view of a drive system including a first tool adapted for use by a left hand and a second tool adapted for use by a right hand, in accordance with an embodiment.

FIG. 1 illustrates one exemplary embodiment of a tool 10 comprising a control member 20, catheter 22, and end effector 24. Control member 20 is illustrated in more detail in FIGS. 2A through 2G and can include a handle 26 that allows a user to control actuation of catheter 22 and a trigger 28 that allows a user to actuate the end effector.

In one embodiment, control member 20 includes a body 30 that houses a control mechanism for transferring user inputs on handle 26 to catheter 22 and/or end effector 24. User input forces can be directed into pull and/or push forces on one or more control wires that extend between the control mechanism and the catheter articulation section and/or end effector. As used herein, "control cable" refers to the various filaments, wires, cables, bowden cables (inner cable and/or outer sheath) which can transmit user inputs between the control mechanism and the distal portion of the catheter. Descriptions of exemplary cables, catheters, and end effector are disclosed below and in the above referenced United States Patent Applications.

Described below and illustrated in FIGS. 2A through 2G are various exemplary control mechanisms. In one aspect, user inputs to the handle can rotate or pivot at least a portion of the control mechanism. Rotation around a first axis can control one degree of movement of the catheter and rotation around a second axis can control a second degree of freedom. Tool 10 can also, or alternatively, include a trigger mechanism for driving an additional degree of freedom. In one aspect, the trigger mechanism is position, at least partially, on or in the handle of tool 10. As used herein, the term "trigger mechanism" can refer to the variety of switches, buttons, rockers, and/or other such features for mechanically or hydraulically driving a degree of freedom, such as, for example, movement of the end effector.

Figure 2B:
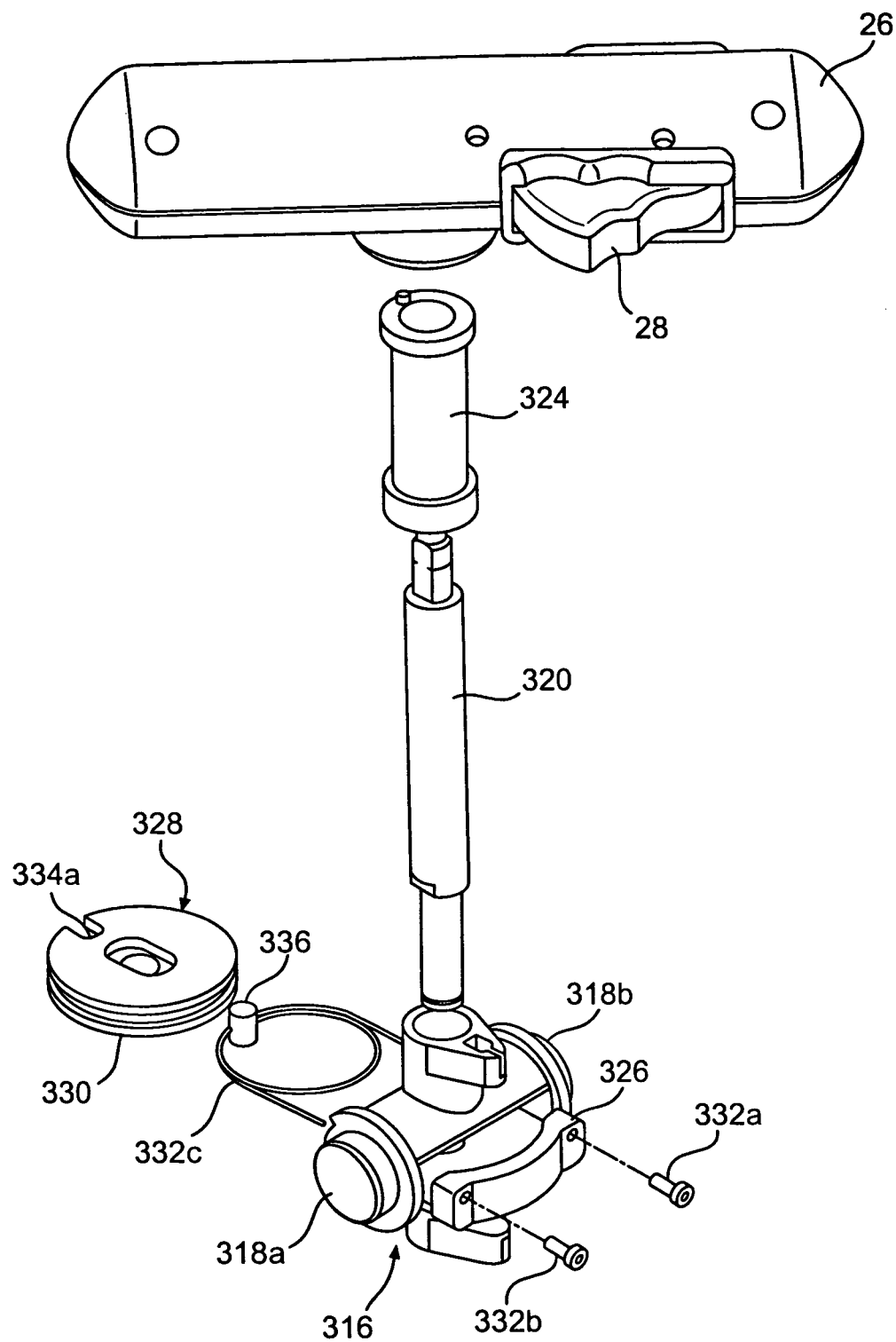
FIG. 2B is an exemplary illustration of tool components in accordance with an embodiment.

As shown in FIGS. 2A and 2B, handle 26 can be rotatably coupled to the body of control member 20 such that the handle is able to move forward and aft. In one aspect, the handle rotatably couples with side rails 310a and 310b to rotate about axis B-B. The rails are included as part of the housing and/or frame in one embodiment. In addition, handle 26 can rotate about an axis, such as, for example, an axis A-A defined by or parallel with shaft 320. Movement of the handle back and forth during rotation about axis B-B can cause the distal tip of the tool 10 to move in one plane while rotation of handle 26 about the longitudinal axis A-A of the shaft 320 can cause movement of the distal tip of the tool 10 in another plane. As shown in FIG. 2A, rotation axes A-A and B-B are different from the longitudinal axis C-C of the body of control member 20.

The handle can be secured to side rails 310a and 310b with a trunnion 316. Trunnion 316 includes a pair of outwardly extending posts 318a, 318b that fit in corresponding holes formed in side rails 310a, 310b. The connection between the posts and side rails can allow movement of the trunnion within the control member. In one aspect, a mating mechanism such as, for example, a snap ring or other fastener can secure posts 318a, 318b into the side rails. Alternatively, or additionally, the post can be secured by sandwiching between the side rails.

Figure 2D:
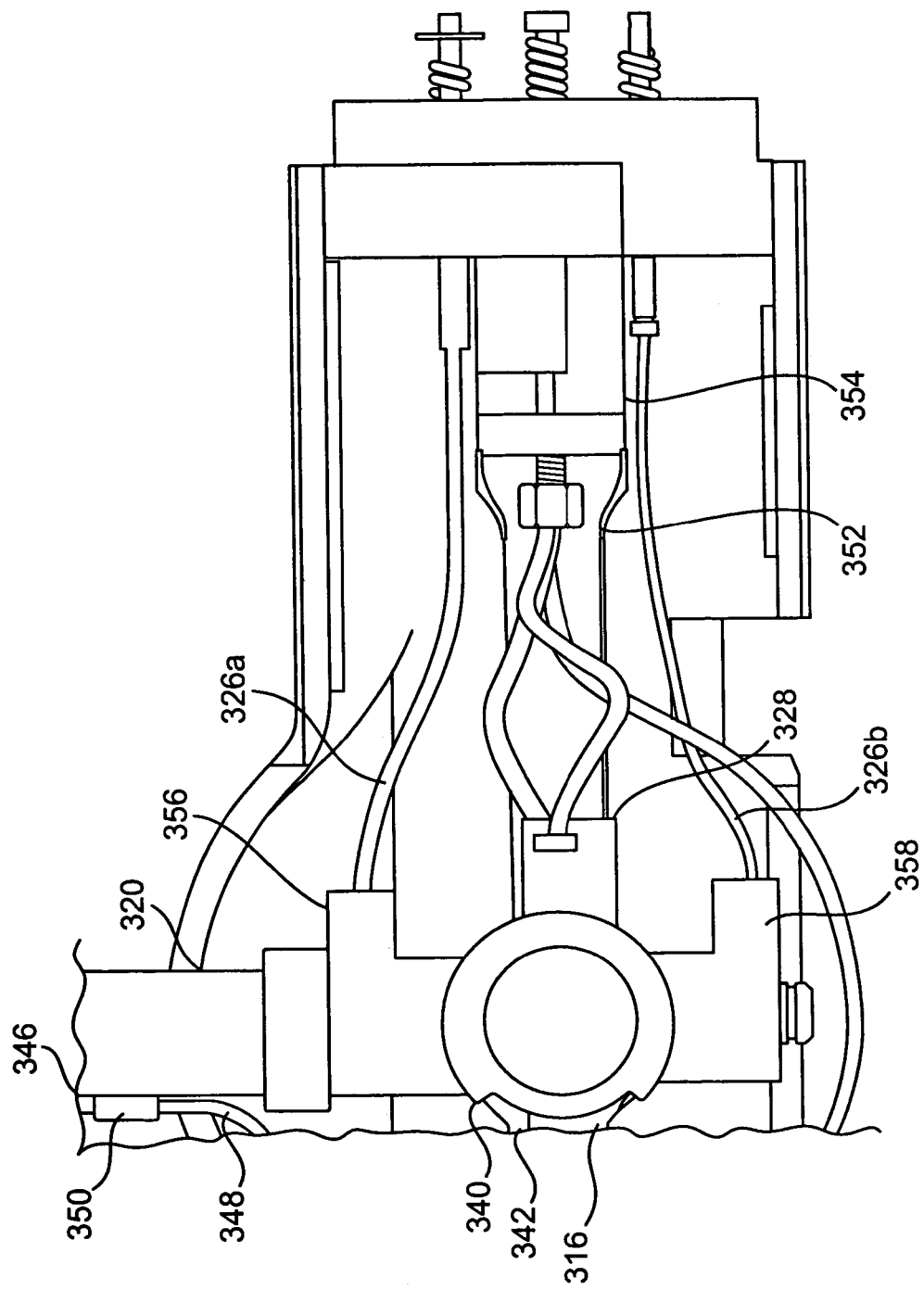

Forward/aft movement of the handle can pivot trunnion 316, for example, around an axis B-B extending through posts 318a, 318b. The trunnion can mate with control cables such that pivoting the trunnion applies for to one or more control cables and drives at least one degree of freedom. The trunnion can include a pair of cable receivers 356, 358 having a slot or other receptacle therein that secures an end of an articulation cable. As shown in FIGS. 2C and 2D, one of the cable receivers 358 is below the pivot point of trunnion 316, and the other is above the pivot point. Upon tilting trunnion 316 in the control member, the cable receivers 356, 358 selectively tension or release control cables that move the distal tip of tool 10.

FIGS. 2C and 2D illustrate further detail of trunnion 316. The control mechanism can include a stop to limit the amount of forward and aft movement of the handle 26. In one aspect, a ring 340 fits over the posts of trunnion 316 and has a notch 342 therein. A pin 344 secured in the side rail (not shown) limits how far the handle can travel by engaging the ends of the notch 342. Other structures besides pins can also be used. While the FIGS. illustrate a ring/pin configuration, one skilled in the art will appreciate that a variety of alternative mechanisms can be used to limit motion of the cable guide plate. In addition, the illustrated configuration could be reversed such that the notch could be located on the side rail and the pin could be located on the trunnion.

Trunnion 316 can further includes an opening or slot in which a cable guide plate or disk 328 is located. In the illustrated embodiment of FIGS. 2B, 2C, and 2D, cable guide plate 328 is generally circular and mates with at least one control cable. In one aspect, control guide plate 328 includes a groove 330 therein in which control cable 332c is fitted. In addition, cable guide plate 328 can include a notch 334a that receives a corresponding cable stop 336 that is secured to cable 332c (while a single notch/stop/cable is illustrated, additional notches, stops, and/or cables are contemplated). Movement of the cable guide plate causes corresponding tension or relaxing of cable 332c.

The cable guide plate 328 can be fitted into a slot within the trunnion such that it lies behind the stop plate 326. In one aspect, the shaft 320 fits through a corresponding hole in the cable guide plate 328 and a snap ring or other fastening mechanism secures the components together. Rotation of the handle 26 causes a corresponding rotation of the shaft 320 which in turn is coupled to the cable guide plate 328 to tension or release cable 332c.

Cable 332 is illustrated as wrapped around disk 328 more than 360 degrees. In another aspect, cable 332 can be wrapped around the disk more than about 180 degrees, and in another aspect more than about 270 degrees. In yet another aspect, cable 332 mates to disk 328 without wrapping around a portion of the disc. In embodiments where the control mechanism includes a force limiter, the cable may also attach to the force limiter.

While a single cable 332c is illustrated as mated with disk 328, in another embodiment two control cables can mate with the disk. Rotation in a first direction can tension one of the two cables, while rotation in the other direction tensions the other of the two cables.

In one aspect, trunnion 316 further includes a stop plate 326 that provides an anchor for the ends of control cable sheaths 332a, 332b, or more particularly, the sheaths of bowden cables. Control cable 332a, mated with disk 328, can extend through bowden cable sheaths 332a, 332b. The stop plate 326 pivots up and down with the trunnion 316 as the handle 26 is moved forward and aft. The bowden cables can permit the trunnion to pivot around posts 318a, 318b (controlling one degree of freedom) without (or with minimal) effect on control cable 332a (which controls a different degree of freedom).

Also shown in FIGS. 2C and 2D is a control cable 346 that is actuated by the trigger mechanism 28 on the handle. Depressing trigger 28 causes a tensioning of the cable 346 to actuate, for example, an end effector 24 at the distal end of the tool. In the illustrated embodiment, cable 346 is a bowden-type cable having an outer sheath 348 with one end secured to a cable stop 350 positioned on the shaft 320 (or collar 324, or handle 26). The cable is not exposed outside the handle in one embodiment. The other end of the bowden cable housing extends through a cross bar 354 and joins a stop at the distal end of the catheter. The crossbar 354 also includes stops for the bowden cable housings 332a, 332b that are driven by rotation of the handle as described above.

Figure 2E:
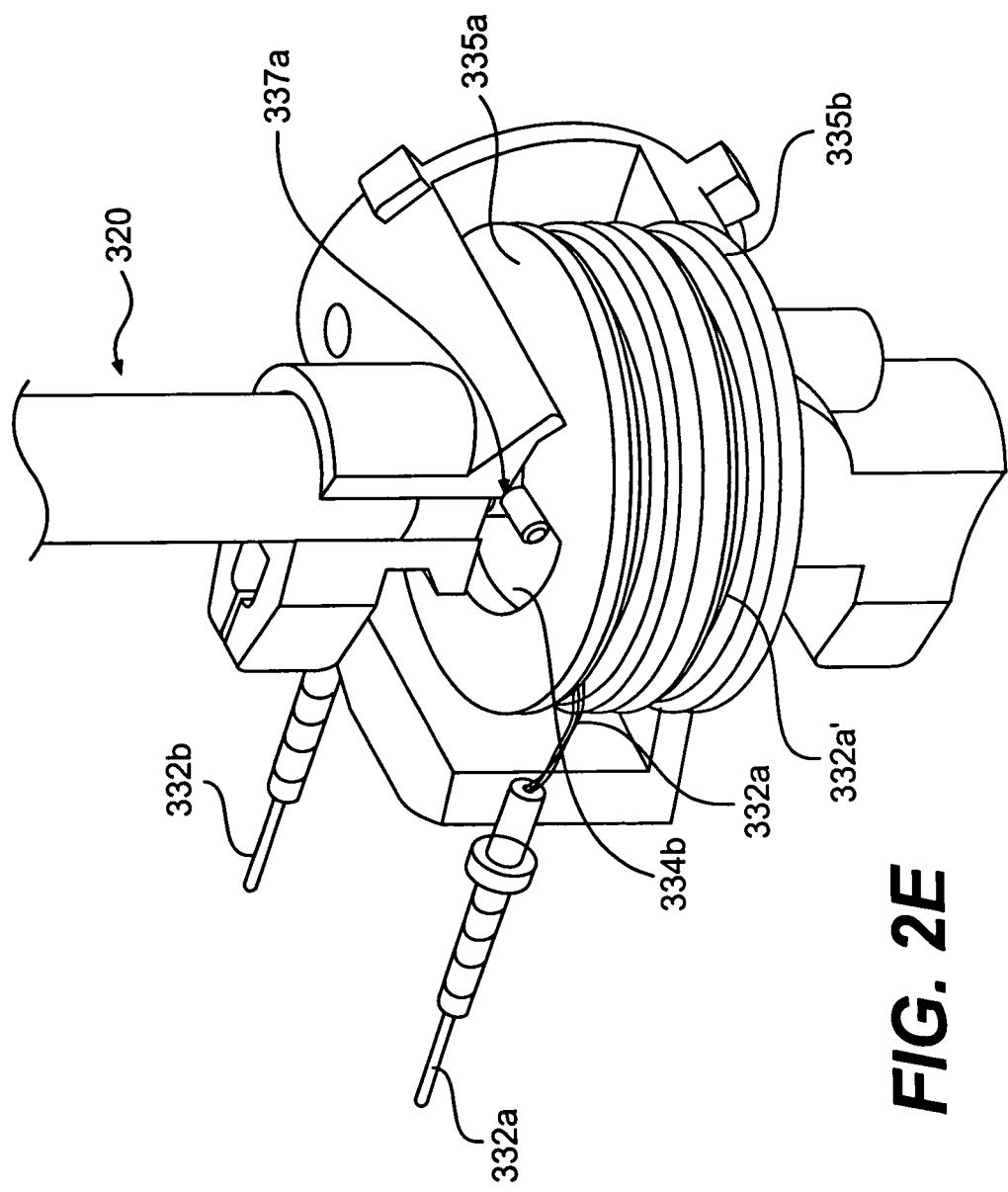
FIG. 2E is an exemplary illustration of a trunnion with a double-pulley system and a control stem in a neutral position, in accordance with an embodiment.
Figure 2F:
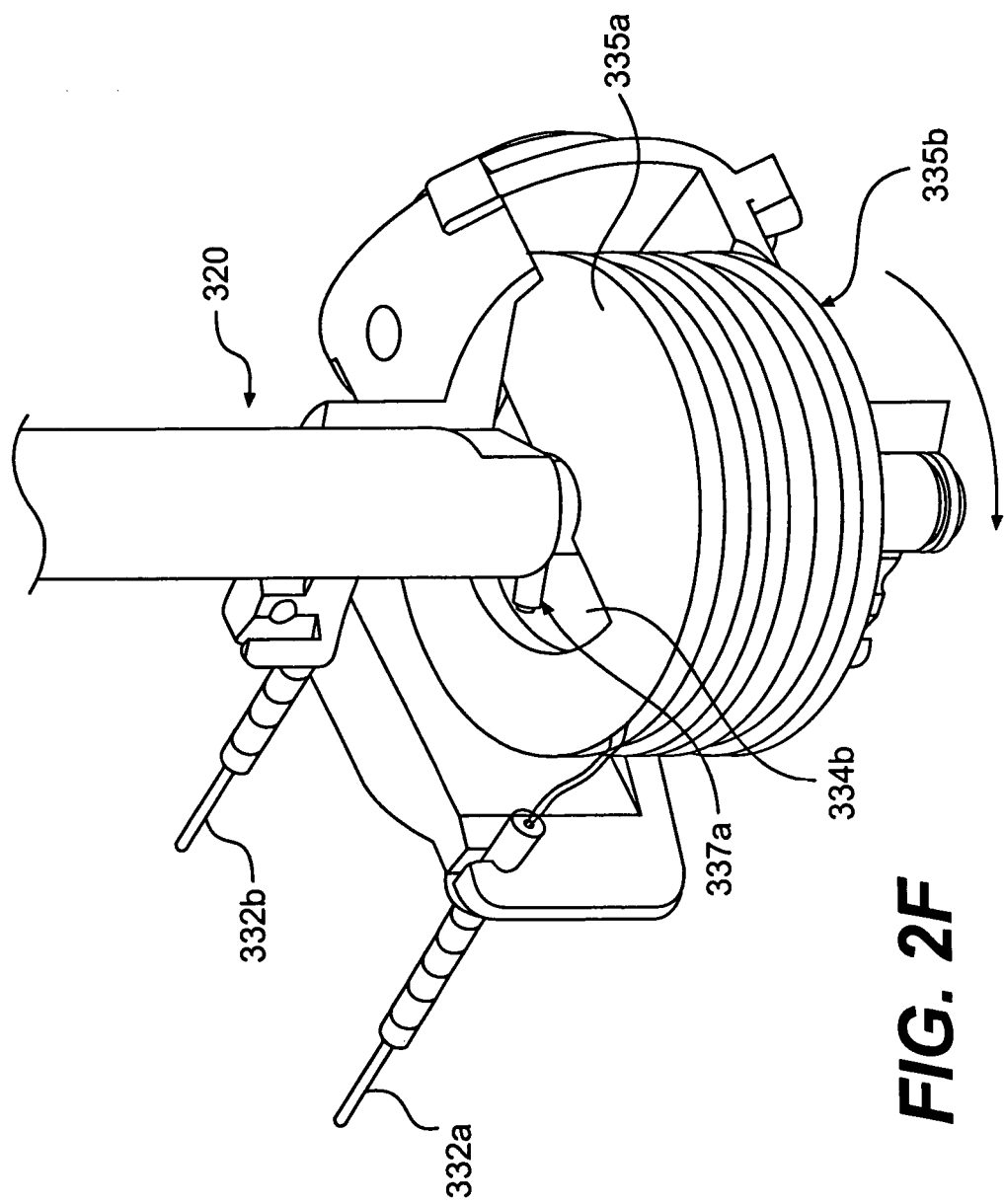
FIG. 2F is an exemplary illustration of a trunnion with a double-pulley system and a control stem turning clockwise, in accordance with an embodiment.

FIGS. 2E and 2F illustrate a trunnion with a dual pulley (or dual disk) system that serves as an alternate embodiment to the single-pulley system previously described. As used herein, the pulley or disk can comprise a rotating mechanism and is not limited to a circular member. As the tool handle is rotated in a first and second direction, the double-pulley configuration can apply a pulling force on control wire 332a or 332a' without pushing on the other of control wires 332a, 332a'. A top pulley 335a corresponds to first cable 332a, and a bottom pulley 335b corresponds to cable 332b. Each pulley contains only one control cable 332d and 332e. Typically, the two pulleys 332a and 332b are stacked on top of one another, separated by a frictionless washer, such as a piece of Teflon™.

A top pin 337a drives the top pulley 335a, while a bottom pin (not shown) drives the bottom pulley 335b. Unlike the single-pulley embodiment, the top and bottom pulleys each include a rut 334b, such that the respective pin 337a can rotate freely in the rut 334b without driving the respective pulley. Although referred to herein as pins, both the top pin 337a and bottom pin (not pictured) can have other shapes, such as a protrusion with a flat surface for engaging the stop.

FIG. 2E illustrates a double-pulley trunnion with the control stem 320 in a neutral position. In this position, a counterclockwise turn of the control stem 320 will engage the top pin 337a with the stop of top pulley 335a. As a result, top pulley 335a pulls on first cable 332a, and the catheter bends. However, the bottom pin (not shown) swings in the rut of the bottom pulley 335b, and does not force bottom pulley 335b to rotate.

Conversely, FIG. 2F illustrates the double pulley interaction when the control stem 320 rotates clockwise. The top pin 337a rotates in rut 334b, and consequently does not push or pull first cable 332a. On the other hand, the bottom pin engages the stop of the bottom pulley 335b, and the bottom pulley 335b rotates clockwise. This rotation applies tension to the right wire, which is pulled towards the bottom pulley 335b.

As a result, neither wire 332a gets forcefully pushed out by the top or bottom pulleys 335a and 335b. Instead, the pulleys only pull on their respective wires. However, in one embodiment, the wires are free to move back to respond to other tensions applied on the catheter.

Figure 2G:
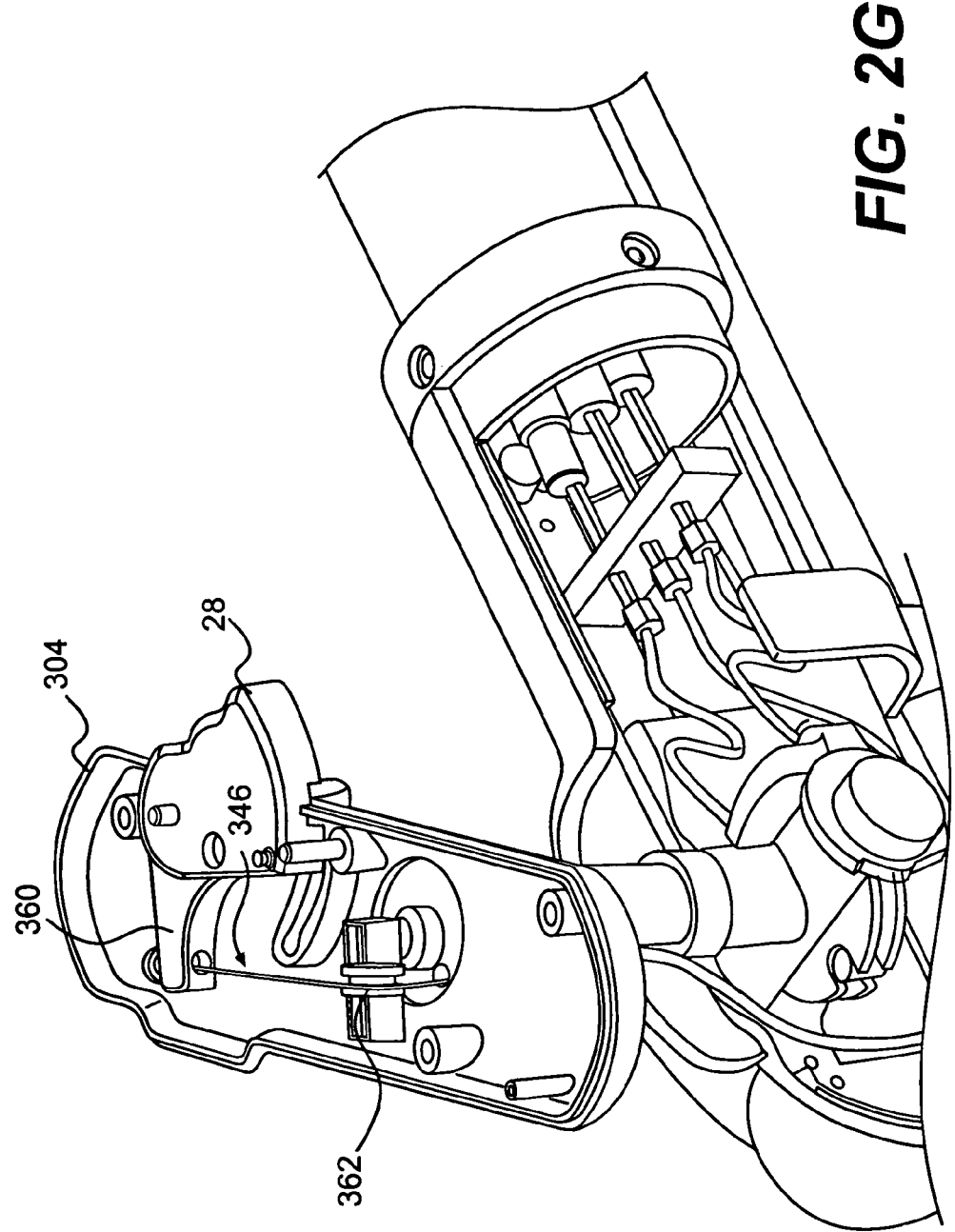
FIG. 2G is an exemplary illustration of trigger mechanism components in accordance with an embodiment herein.

Further detail of one embodiment of a trigger mechanism 28 is shown in FIG. 2G. In the illustrated embodiment, the trigger 28 is rotatably received within the handle 26 such that squeezing the trigger 28 causes it to rotate about a pivot point. The trigger 28 includes an arm 360 to which an end of the actuation cable 346 is secured. As the arm 360 is moved by pressing the trigger, tension on the control cable 346 is increased to actuate the end effector. A roller or pulley 362 changes the direction of the control cable 346 from within the handle to a direction that extends along the shaft 320.

Figure 2H:
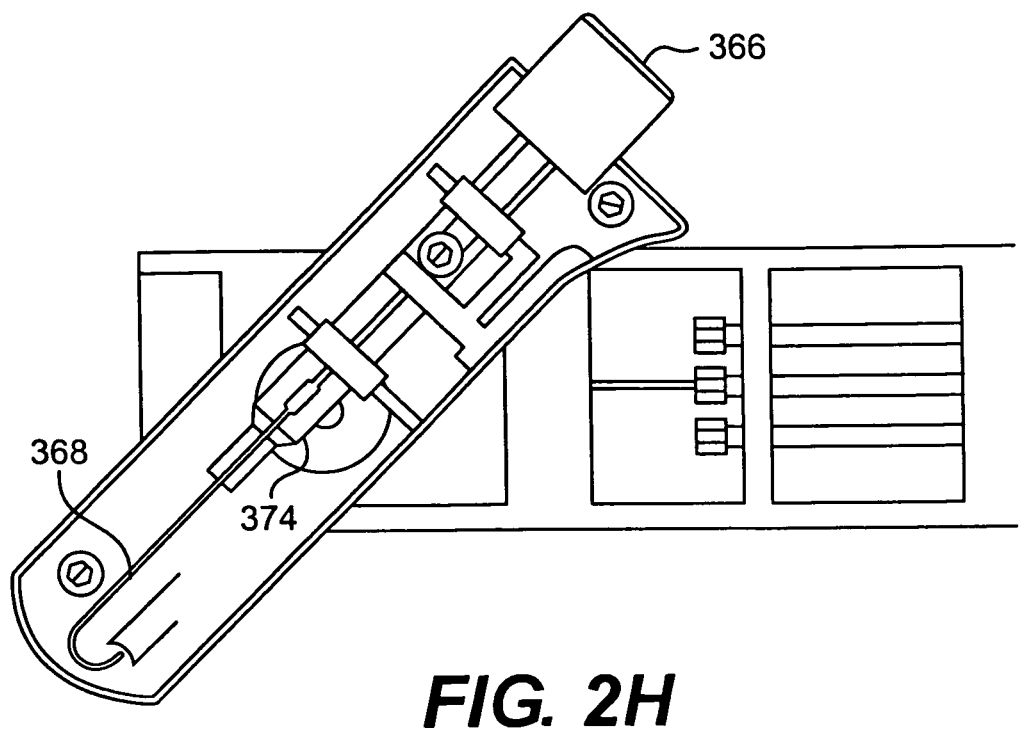
FIGS. 2H and 2I are exemplary illustrations of another trigger mechanism in accordance with an embodiment.
Figure 2I:
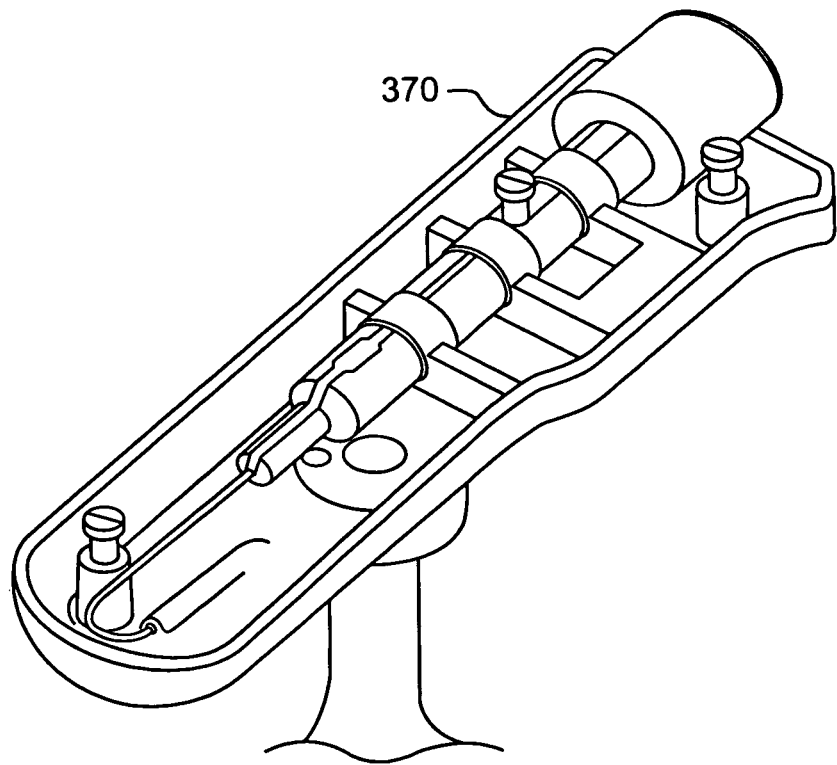

FIGS. 2H and 2I illustrate another embodiment of a trigger mechanism that includes a button 366 for activating the distal end of tool 10. A bowden cable 368 can extend into handle 26 to trigger mechanism 370. The second end of the outer sheath 372 of the bowden cable extends in clearance through crossbar 354 and through the body of surgical tool where it terminates proximate to end effector. The outer sheath 372 of the bowden cable 368 can mate with a stop 374 in the trigger mechanism while the inner filament 376 extends into trigger mechanism 370. When button 366 is depressed, trigger mechanism 370 tensions inner filament 376. In one aspect, trigger mechanism 370 include a ratchet-type lock that prevents the release of inner filament 376 once tensioned. A button 378 can be depressed to release inner filament 376 and allow the distal end of tool 10 to return to its original configuration.

Figure 2K:
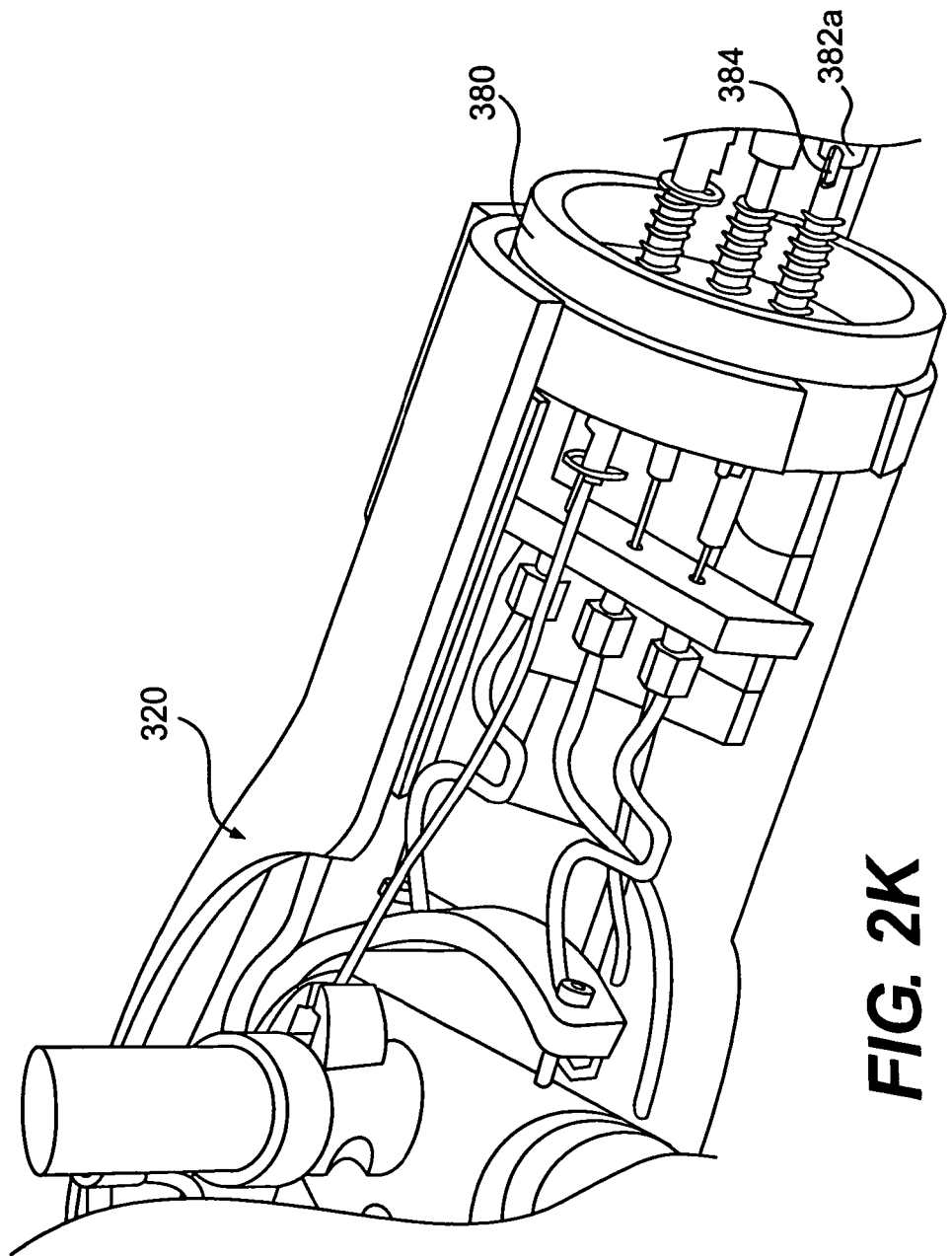

FIGS. 2J and 2K illustrate one embodiment of a coupling mechanism that can be used to selectively couple the control member 20 to one or more control wires (i.e., control cables) within the tool 10 (e.g., within catheter 22). The coupler 380 forms an end-wall that is positioned within the actuator housing between the support rails 310a, 310b. The coupler 380 has a number of spring loaded pins 382a, 382b, 382c, etc., positioned therethrough. Each of the pins 382a, 382b, 382c, etc., is connected to a control cable that is moved by the handle 26 or the trigger mechanisms as described above. Each pin includes a cable receiving notch 384 therein that receives the ball or stop at the end of a corresponding control cable 386a, 386b, 386c, etc. for the medical device. Secured by a cable terminal in the slots 384, each pin allows the tensioning or release of the corresponding cables 386a, 386b, 386c, etc. In the embodiment shown, each of the pins 382a, 382b, 382c, etc. includes a spring 388a, 388b, 388c that biases the pin toward the distal end of the control member 20. The springs 388 serve to tension the control cables within the body of the control when not being pulled by the actuator and biases the control handle to return to a home position.

To connect the cables of catheter 22 of tool 10 to the control member 20, the terminal ends of each of the control cables 386a, 386b, 386c, etc. are inserted into each of the cable receiving slots 384 of the corresponding pins. Similarly, to disconnect the cable, the balls or cable ends are removed from the cable receiving slots 384. Upon completion of a procedure, the catheter can be uncoupled from the control member 20, cleaned or sterilized for re-use or thrown away.

In one aspect, the various cables within control member 20 can be adjustably tensioned. For example, in one embodiment spring loaded pins 382 can have a threaded connection with coupler 380 (additional disconnect configurations are described below). Rotating pins 382 can move pins laterally to control the tension on control wires mated to pins 382. For example, rotating the pins 382 can compress or relax springs 388 and adjust tension on the control wires.

In another embodiment, tool 10 does not include the coupler 380 or the spring and pin arrangement shown in FIG. 2J. In such an embodiment, the disc 328 mates with one end of the control wire(s) while a catheter articulation section and/or end effector mates with the other end of the control wire(s). Removing the springs can increase the tactile feedback and efficiency of the tool 10, because the user need not overcome the bias of the springs when controlling the tool 10.

Because the springs also return the catheter articulation to a home position (such as straight), a spring-less embodiment may not have this feature. However, for some procedures, it is preferable for the catheter and/or end effector to remain in a current position without automatically returning to a home position. The ability to leave the tool 10 in a current position can free the user to perform another task instead of maintaining constant control over tool 10.

In accordance with this need, either type of tool 10 (springs or no springs) can include a mechanism for locking the catheter and/or end effector into place. One such mechanism includes a pawl that interlocks with teeth to stop actuation. In one aspect, the user can lock and unlock the actuation by manipulating a button, slide, or trigger mechanism that engages and disengages the pawl with the teeth.

The location of the pawl and teeth can vary, depending on the type of actuation it controls. For example, a handle 26 can be locked by providing a locking mechanism for the stem. A locking mechanism on the trigger, push-pull mechanism, etc. can lock the end effector in place. This can allow the user to position and lock a clamp in place for the duration of some other step of the procedure.

Figure 3:
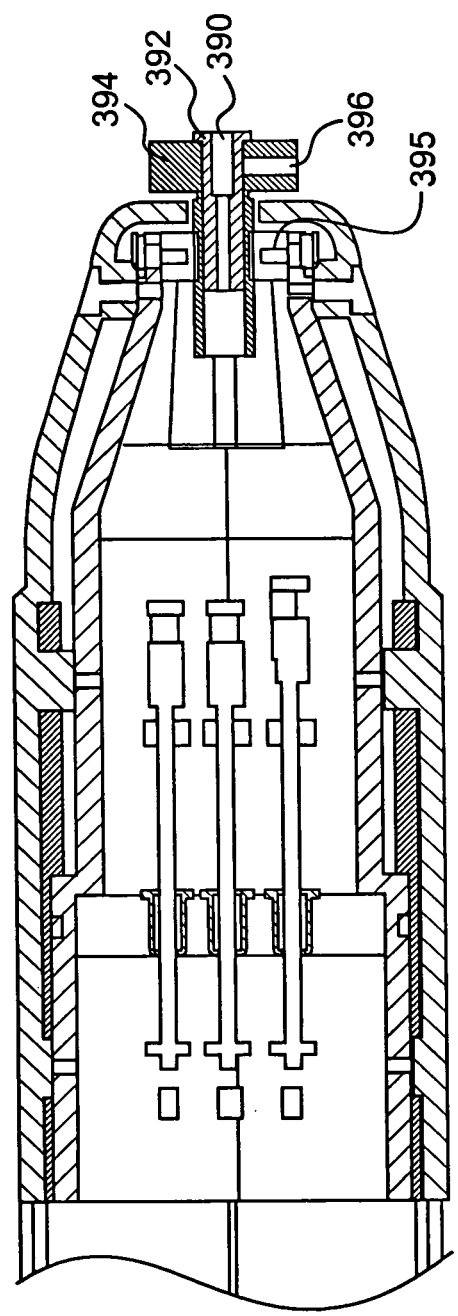
FIG. 3 is an exemplary cross-section of the distal end of a control mechanism with an adjuster, in accordance with an embodiment.

In another embodiment of control mechanism 20, tool 10 can include a orientation adjuster. In use, the orientation adjuster can allow a user to rotate the elongate body and distal end of a tool relative to control mechanism 20. FIG. 3 illustrates a cross-section of the distal end of control mechanism 20 with adjuster 394. Adjuster 394, in one aspect, can include an inner member 392 having a passageway 390. The passageway 390 can mate with the elongate body (not illustrated) of catheter 22. In one embodiment, the elongate body of catheter 22 includes an outer sheath that fixedly mates to the inner surface of passageway 390. One skilled in the art will appreciate that a variety of mating mechanisms, such as, for example an adhesive, mechanical interlock, and/or frictional engagement can be used. In addition, the inner member 392 can mate with the inner surface of adjuster 394. For example, as illustrated in FIG. 3, adjuster 394 includes an aperture 396 for a set screw for mating adjuster and inner member 392. In another aspect, adjuster and 394 and inner member 392 can be fixedly mate via, for example, an adhesive. In addition, the adjuster and the inner member can be formed as a single body.

To change the rotational orientation of catheter 22, adjuster 394 can be rotated within control member 20. In one aspect, a locking collar 395 can be tensioned to control the amount of friction between the control member and orientation adjuster 394. For example, the locking collar 395 can be set to inhibit, but not prevent rotation of the adjuster, or set to prevent rotation until adjustment is desired. Since adjuster 394 is mated to inner member 392, and inner member 392 is mated to the body of catheter 22, rotating adjuster 394 causes catheter 22 to rotate relative to control member 20.

Alternate Handle Configurations

Figure 4:
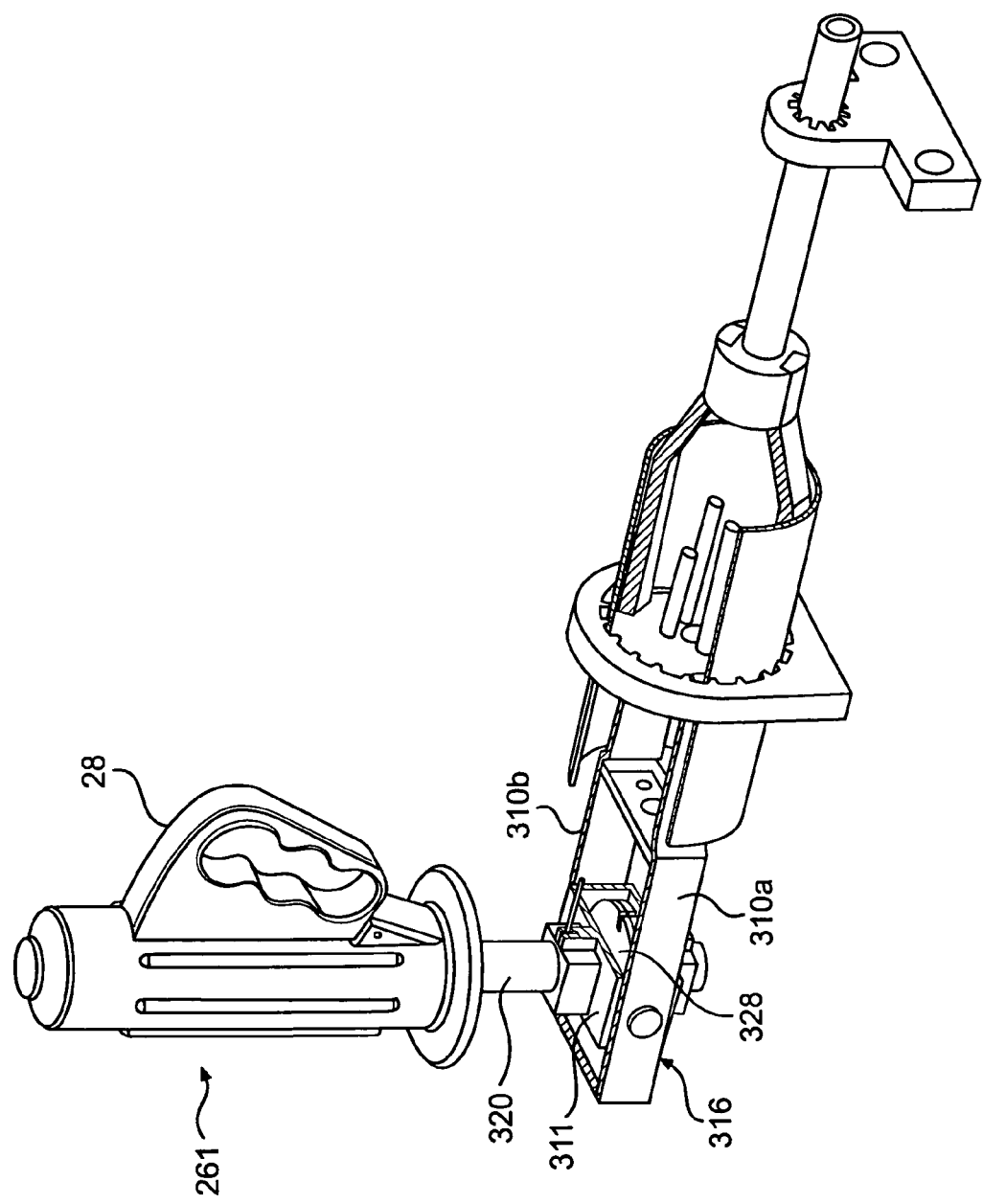
FIG. 4 is an exemplary illustration of a handle with a joystick configuration, in accordance with an embodiment.

Described below are alternative control mechanisms for actuating catheter 22 and/or end effector 24. FIG. 4 illustrates handle 261 having a "joystick" configuration. In general, a handle in joystick configuration stands on its end rather than on its side. In one aspect, the control member can include a trunnion-type configuration as describe above, that provides at least one degree of freedom to handle 261. However, instead of the handle positioned orthogonally to shaft 320 as described above, handle 261 can be parallel to the axis of shaft 320. For example, handle 261 can be co-linear with shaft 320.

Forward-aft movement of handle 261 can be achieved in a similar fashion to the trunnion and disk configuration discussed above. For example, control member 20 of FIG. 4 can include trunnion 316 that rotatably mates with side rails 310a, 310b and a base 317 that houses disk 328. Base 317 can mate with cables (not illustrated) to control one degree of freedom as handle 261 is moved forward-aft.

Disk 328 can reside in base 317 and movably mate therewith. Twisting or rotating handle 261 can rotate disk 328 to control another degree of freedom. For example, rotating handle 261 about its axis can direct side-to-side movement of the catheter.

Handle 261 can also include a trigger 28 that controls, for example, a third degree of freedom. Actuating trigger 28, in one aspect, can control distal end effector 24. The trigger mechanism within handle 261 can have a configuration similar to the triggers discussed above. Thus, the control mechanism of FIG. 4 can work in a similar fashion to the control members of FIGS. 2A through 3, but with handle 261 in a different orientation compared with handle 26.

Figure 5:
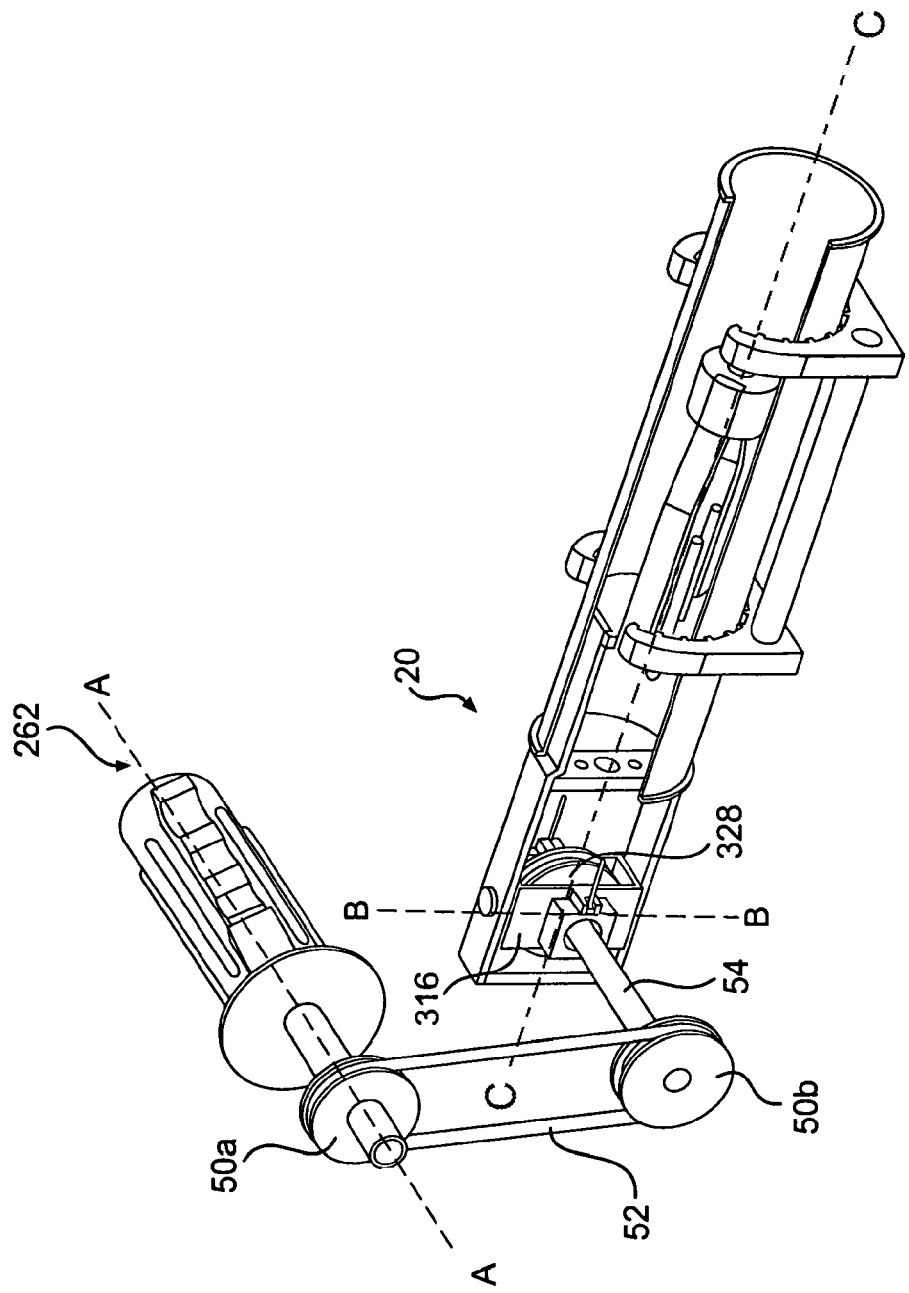
FIG. 5 is an exemplary illustration of an alternative handle orientation, in accordance with an embodiment.

FIG. 5 illustrates an alternative handle orientation. Rotating handle 262 around its axis (axis A-A) can control one degree of freedom. For example, rotating the top surface of handle 262 away from the user can move the distal tip of the catheter down and rotating the top surface of handle 262 toward the user can move the distal tip of the catheter up. Handle 262 can also be rotated around an axis, such as, for example, an axis orthogonal to the longitudinal axis of the tool, to control another degree of freedom. In one aspect, handle 262 can be rotated around axis B-B to control side-to-side movement of the distal end of the catheter. As shown in FIG. 5, rotation axes A-A and B-B are different from the longitudinal axis C-C of the body of control member 20.

In one aspect, actuation is achieved via a control mechanism similar to those described above. FIG. 5 illustrates a trunnion and disk configuration similar to that of handles 26, 261 described above. Movement around axis B-B can rotate trunnion 316, while rotation of handle 262 around its axis can move disk 328. However, unlike the mechanisms described above, handle 262 can drive disk 328 via a belt and/or chain drive. A pulley 50a connected to handle 262 can drive pulley 50b via belt 52. Pulley 50b can mate with a shaft 54 that extends to disk 328.

Rotation around axis B-B can be driven through a frame or shaft (not illustrated) extending between handle 262 and trunnion 316 to transfer rotational force between the handle and trunnion. Rotational forces can additionally, or alternatively, be applied on shaft 54 through the belt and pulley system.

In another embodiment, rotating the handle 262 around axis A-A actuates an end effector. This is just one of various actuation members discussed herein.

Figure 6B:
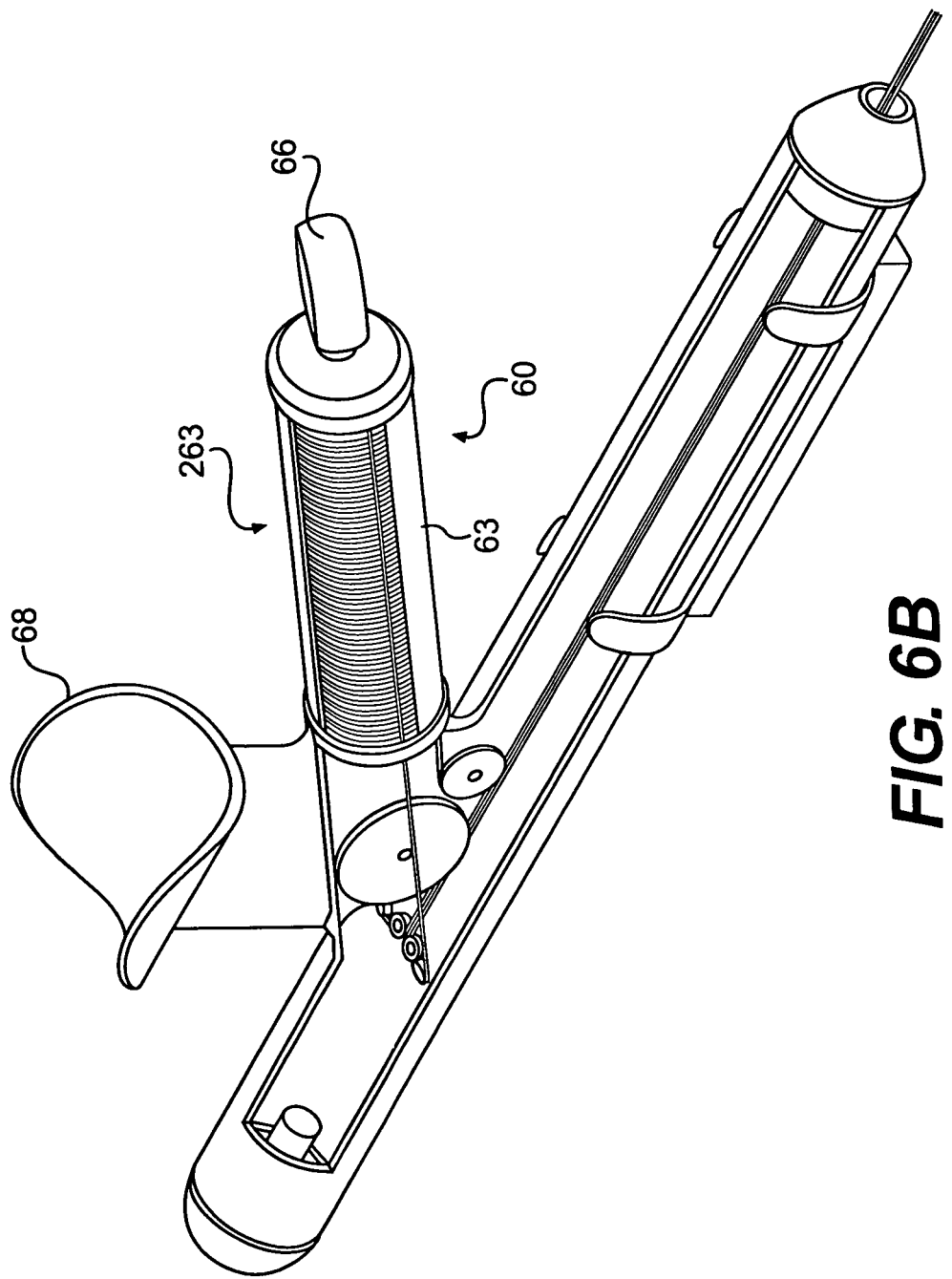

FIGS. 6A and 6B illustrate handle 263 defined at least in part by a flexible shaft 60 that is articulated to control catheter 22. In one aspect, bending shaft 60 up-down or left-right can control a degree of freedom. The distal end 62 of shaft 60 can mate with cables 61. Where two degrees of freedom are controlled via movement of shaft 60, four cables can mate with shaft 60 and extend along a path proximate to the outer surface of the shaft. Bending of the shaft can pull cables 61 by increasing the length of one side of the shaft. As the length of shaft 60 increases with bending, the cable adjacent to the lengthened side is pulled. While four cables and two degrees of freedom are illustrated in FIG. 6A, fewer cables and/or degrees of freedom could be provided.

In one aspect, shaft 60 allows a user to control two degrees of freedom at once. Bending the shaft outside of the forward-aft or side-to-side plane (e.g., at a 45° angle to the forward-aft movement) can pull on two control cables that control separate degrees of freedom. Thus, a single motion can of shaft 60 can control two degrees of freedom simultaneously.

Shaft 60 is formed, in one aspect, is formed from a spring 65. As the shaft is bent, the coils along inside surface of the curve converge while on the opposite side of the shaft the coils move away from one another. Spring 65 can also provide a neutral bias such that when the shaft is released, the catheter returns to a "home" or linear configuration. One skilled in the art will appreciate that the force required to bend the spring and the amount of bend can be chosen by varying the spring materials, the spring wind, pre-compression, and/or the spacing between coils.

Shaft 60 could additionally or alternatively be formed from an elastomic material, such as flexible, compressible, resilient, and/or elastic materials that allow bending. In one aspect, shaft 60 is formed from a flexible polymer or elastomer, such as, for example, silicon. In another aspect, shaft 60 is formed from a series of wafers. Bending is achieved by expanding the distance between wafers along one side of the shaft and/or decreasing the distance between wafers on the opposite side of the shaft.

Shaft 60 can further comprise an outer sheath 63 that covers spring 65 (or other material forming shaft 60) to provide a barrier between spring 65 and a user's hand. In one aspect, sheath 63 can be formed of stretchable or loose material to permit actuation of the shaft. In addition, or alternatively, sheath 63 can be formed of a lubricious material and/or include a lubricious coating to allow sheath 63 to slide over the outer surface of spring 65 as shaft 60 is bent.

The control member 20 can also include pulleys 64 which change the direction of the cables and the force applied through the cables. In one aspect, each cable corresponds to at least one pulley 64.

Handle 263 can, in one aspect, include a trigger, button, or finger loop to permit an additional degree of freedom. As illustrated in FIG. 6, handle 263 can include a finger loop 66 that is actuated by movement along the axis of the shaft. Pushing loop 66 away from the shaft can actuate, for example, distal end effector 24. Alternatively, or additionally, a user can move loop 66 toward shaft 60 to actuate the end effector.

To increase user comfort, control member 20 can include an arm rest 68. A user can place his or her forearm in arm rest 68 while grabbing and actuating shaft 60. The arm rest 68 can also deliver and/or isolate certain degrees of freedom of the control handle. For example, the tip movement can be isolated versus the entire control movement in one embodiment.

Figure 7B:
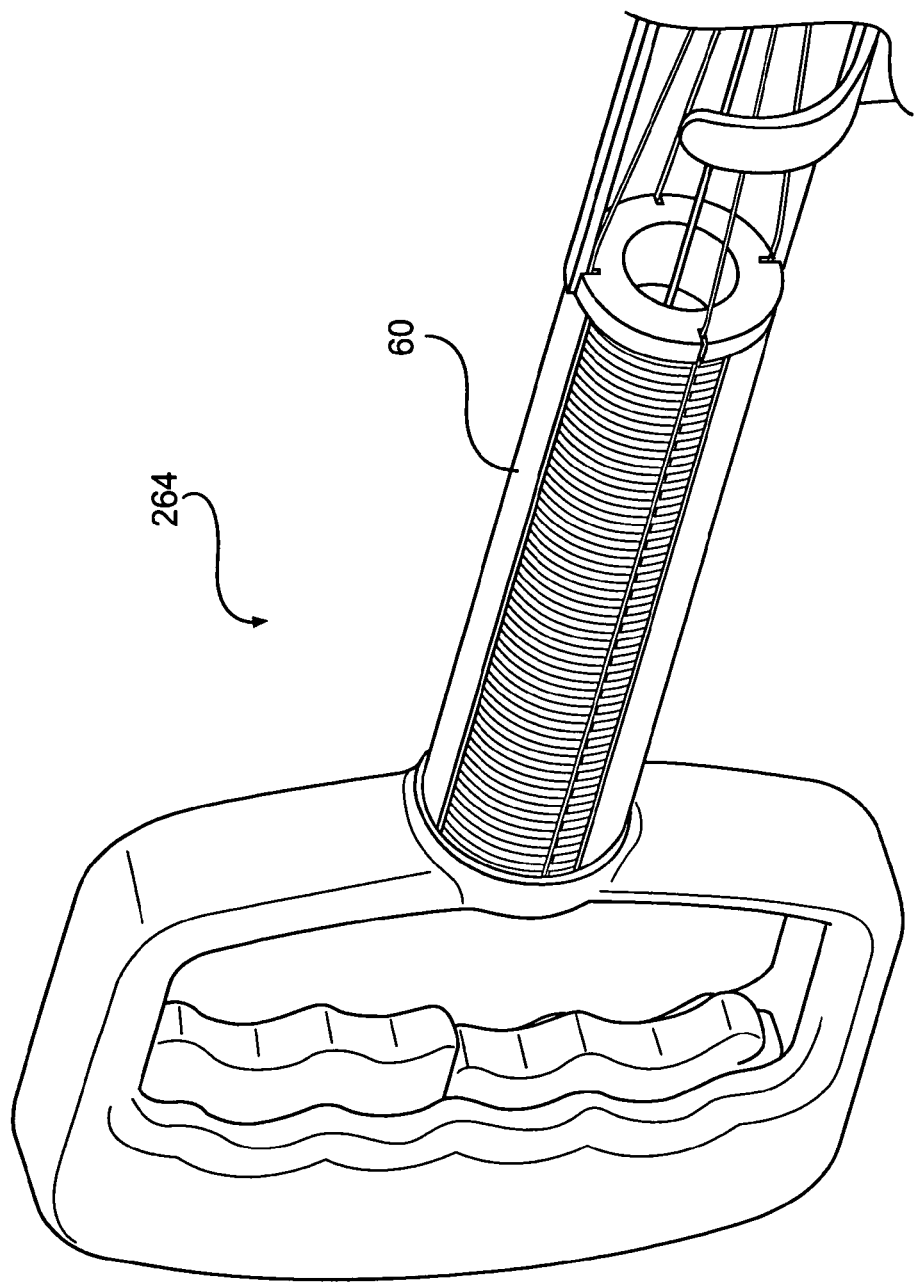
Figure 7C:
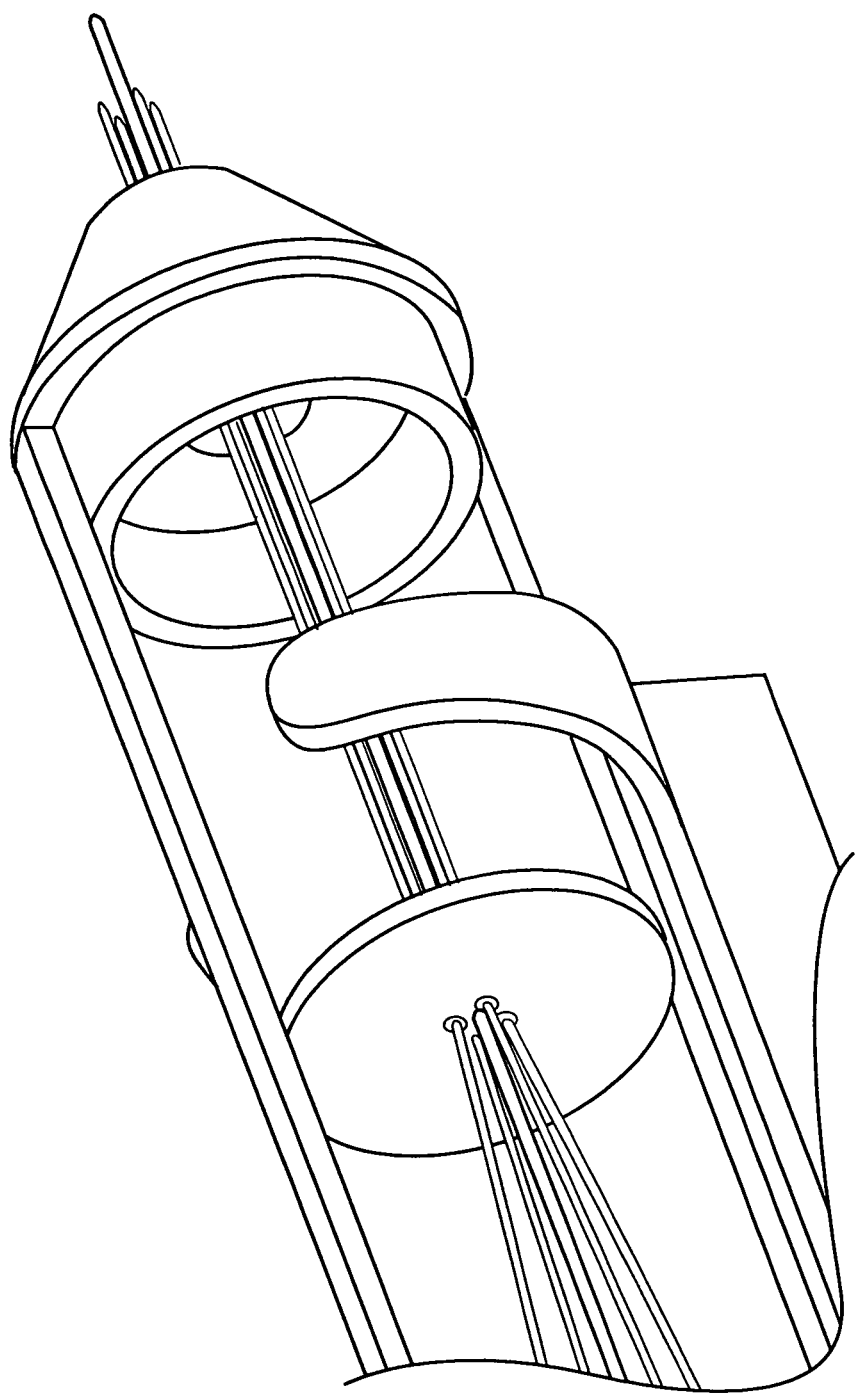
Figure 8A:
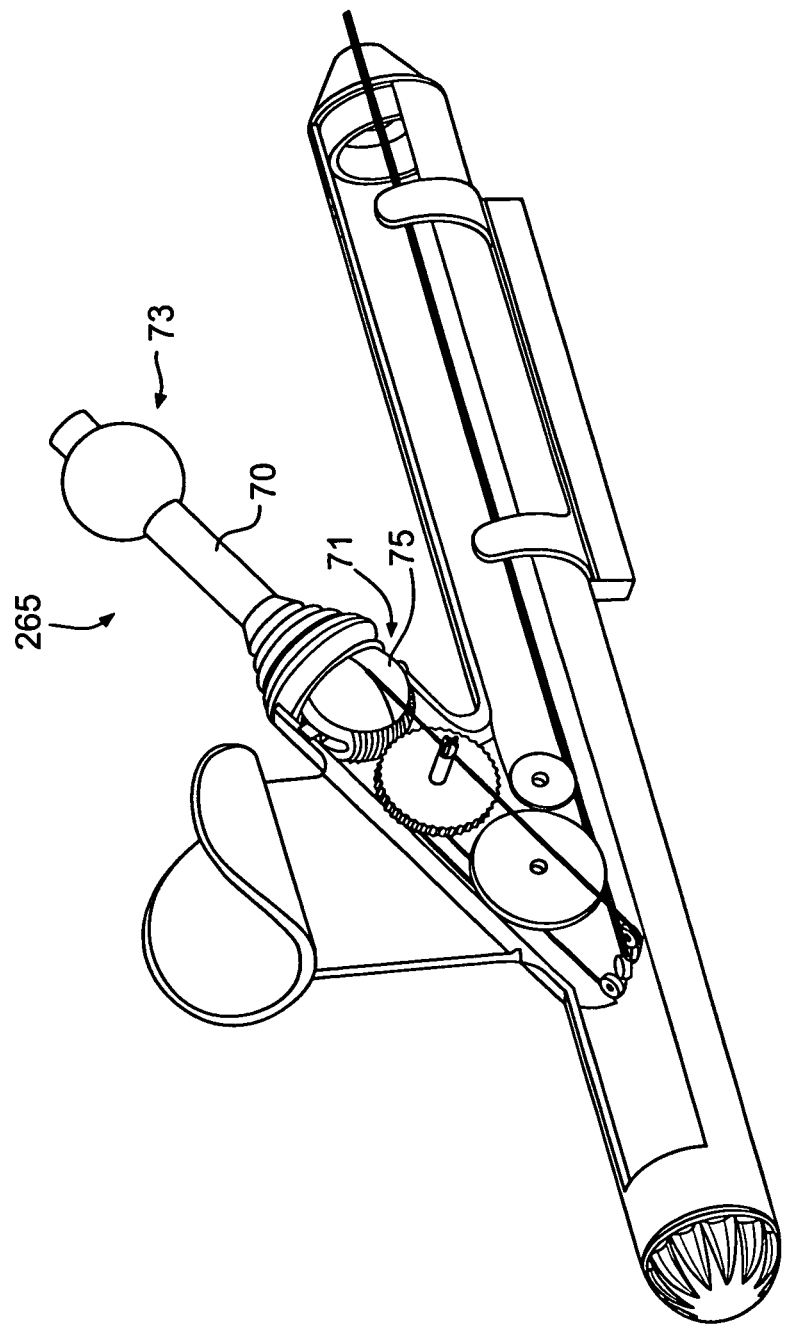
Figure 8C:
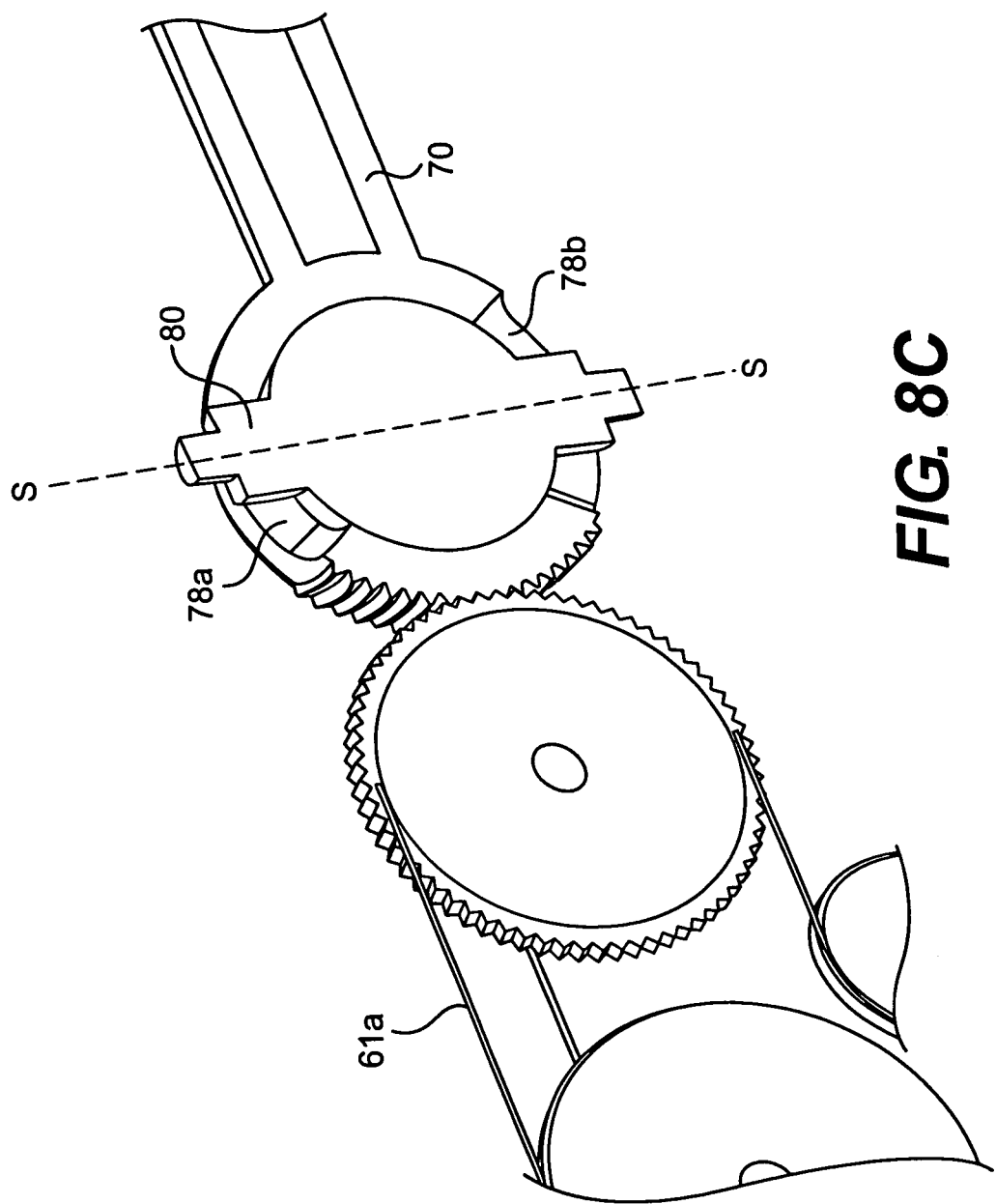
Figure 8D:
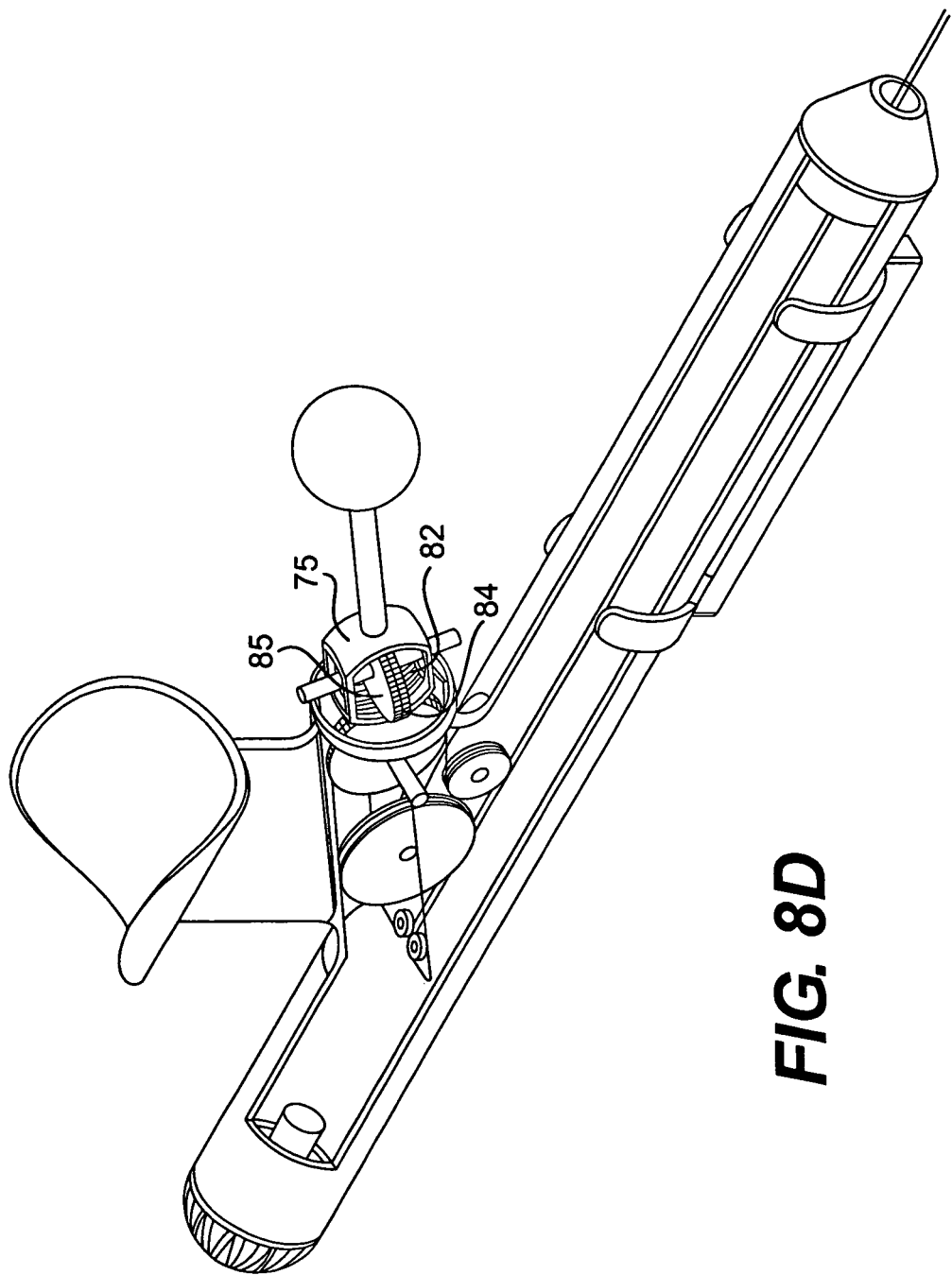

FIGS. 7A through 7C illustrate another exemplary embodiment of a handle 264 incorporating a flexible shaft 60 extending between a proximal end 100 and a distal end 102. However, instead of directly grasping flexible shaft 60, handle 264 can include a grip 104 for a user interface. Grip 104 can have a variety of configurations. In one embodiment, grip 104 includes an aperture for receiving a portion of a user's hand. In addition, the inner surface of grip 104 can include a trigger 106 for actuating an additional degree of freedom.

In one aspect, the distal end of flexible shaft 60 remains stationary while the proximal end of shaft 60 is bent. In particular, shaft 60 can extend in a distal to proximal direction from control member 20 and/or catheter 22 such that pulleys are not needed to change the direction of the control wires. In use, bending shaft 60 in one direction can move the distal tip of the catheter in the opposite direction.

For example, bending the shaft up can move the distal tip down and visa versa. However, control wires can be redirected or crossed if it is desired to change the correspondence between handle 264 and the distal tip of the catheter.

In another embodiment, instead of a flexible shaft, handle 265 can drive gears to control at least one degree of freedom. FIGS. 8A through 8D illustrate gears that permit a user to control two degrees of freedom. Handle 265 can include a rigid shaft 70 extending between a proximal and distal end 71, 73. In one aspect, shaft pivots around proximal housing 75 proximate to proximal end 71. The proximal housing can include a first set of teeth 72 (FIG. 8B) positioned on the proximal surface thereof. Forward-aft movement cause teeth 72 to drive a gear 74 as the first set of teeth 72 mesh with a second set of teeth 76 on gear 74. A control wire 61*a* mated with gear 74 is then driven as gear 74 rotates to control one degree of freedom.

To permit an addition degree of freedom, shaft 70 can be moved side-to-side. FIG. 7B illustrate proximal housing 75 mating with and driving a control wire. Side-to-side movement of shaft 70 pivots housing 75 which in turn drives a second control wire 61*b* mated with the housing. As the shaft moves side-to-side, the first and second set of teeth 72, 76 can slide relative to one another. In one aspect, the proximal surface of shaft 70 has a semi-spherical shape such that as the shaft moves side-to-side, the first teeth do not loose contact with the second set of teeth.

In another aspect, instead of proximal housing mating with control wire 61*b*, a shaft 80 can include a surface for mating with and driving control wire 61*b*. Proximal housing 75 can be anchored or supported via a shaft 80 that extends through the proximal housing and through slots 78*a*, 78*b*. Forward-aft movement of the shaft does not interfere with shaft 80 because slots 78*a*, 78*b* have an elongate shape that permits shaft 80 to remain in place as housing 75 moves relative to shaft 80. Thus, forward-aft movement of housing 75 is independent from shaft 80 (for at least some distance). However, side-to-side movement of shaft 70 causes proximal housing 75 to rotate shaft 80 around an axis S-S (FIG. 8C) and drive control wire 61*b* mated with shaft 80. In particular, with respect to FIG. 8B, the surface on which control wire 61*b* rests can be defined by a portion of proximal housing 75 or by a bulbous portion of shaft 80.

Alternatively, or additionally, a third and fourth set of teeth within housing 75 can transmit side-to-side motion into push-pull motion on a control wire (e.g., control wire 61*b*). For example, as illustrated in FIG. 7D, proximal housing 75 can includes a third set of teeth 82 that mesh with a fourth set of teeth 84 on a second gear 85. As the proximal housing 75 moves side-to-side, teeth 82 on the inner surface of housing 75 drive teeth 84 on gear 85 causing gear 85 to rotate and drive control wire 61*b* (not illustrated). During forward-aft movement, the third and fourth sets of teeth 82, 84 can slide relative to one another without transmitting force therebetween to permit independent control of two degrees of freedom.

These and other handle embodiments can be oriented ergonomically for greater comfort and usability. For example, returning to FIG. 1, handle 26 is tilted off axis from parallel alignment with body 30 of control member 20. In combination with the location of trigger 28, the orientation of handle 26 provides for easy right-handed use of the control member 20.

An embodiment can include two control members 20, 20' mounted on a frame 5 and oriented for left and right handedness, respectively, for simultaneous use. For example, a user may wish to control a first tool 10 with the right hand while controlling a second tool 10' with the left hand. Orienting one handle 20' for left-hand use and the other handle 20 for right-hand use gives the user greater flexibility and comfort when using tools 10, 10'.

Various tools described herein can provide ambidextrous use by permitting changing handedness. In one aspect, the tool handle can be changed between left-handed and right-handed. In another aspect, the user can switch the orientation of a tool on-the-fly. By doing so, the user can operate multiple combinations of tools with either hand during a single procedure. FIGS. 9A through 9K illustrate a few exemplary implementations of this feature. However, the teachings of FIGS. 9A-9K can also apply to other handle embodiments described herein.

Figure 9A:
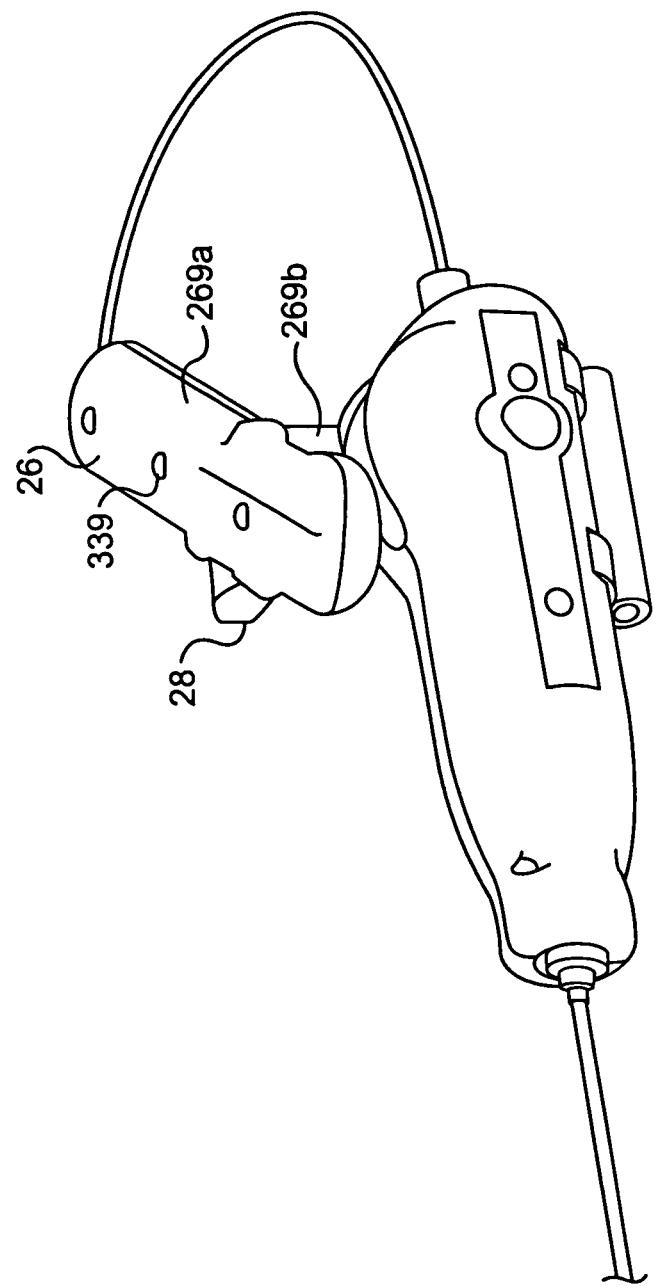
FIGS. 9A through 9C are exemplary illustrations of an ambidextrous handle being changed from right-handedness to left-handedness by detaching and flipping the handle, in accordance with an embodiment.
Figure 9B:
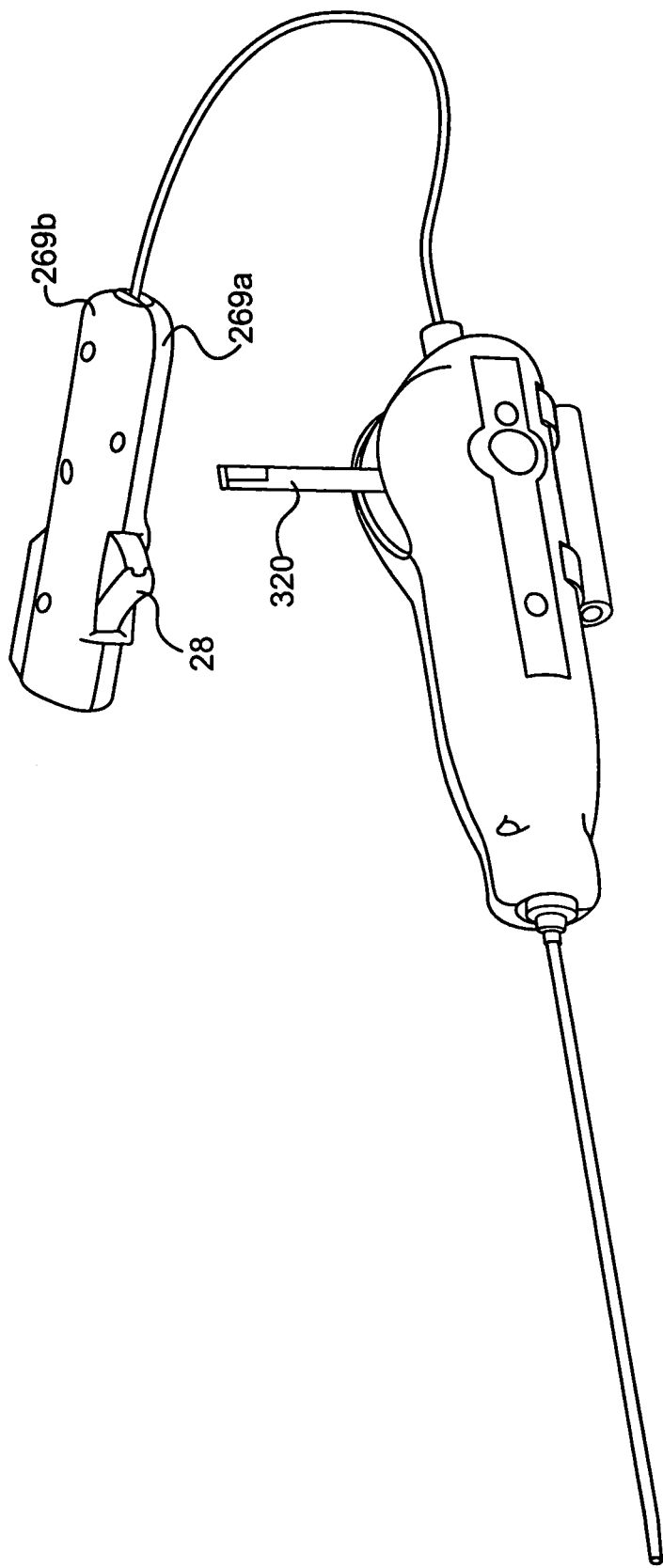
Figure 9C:
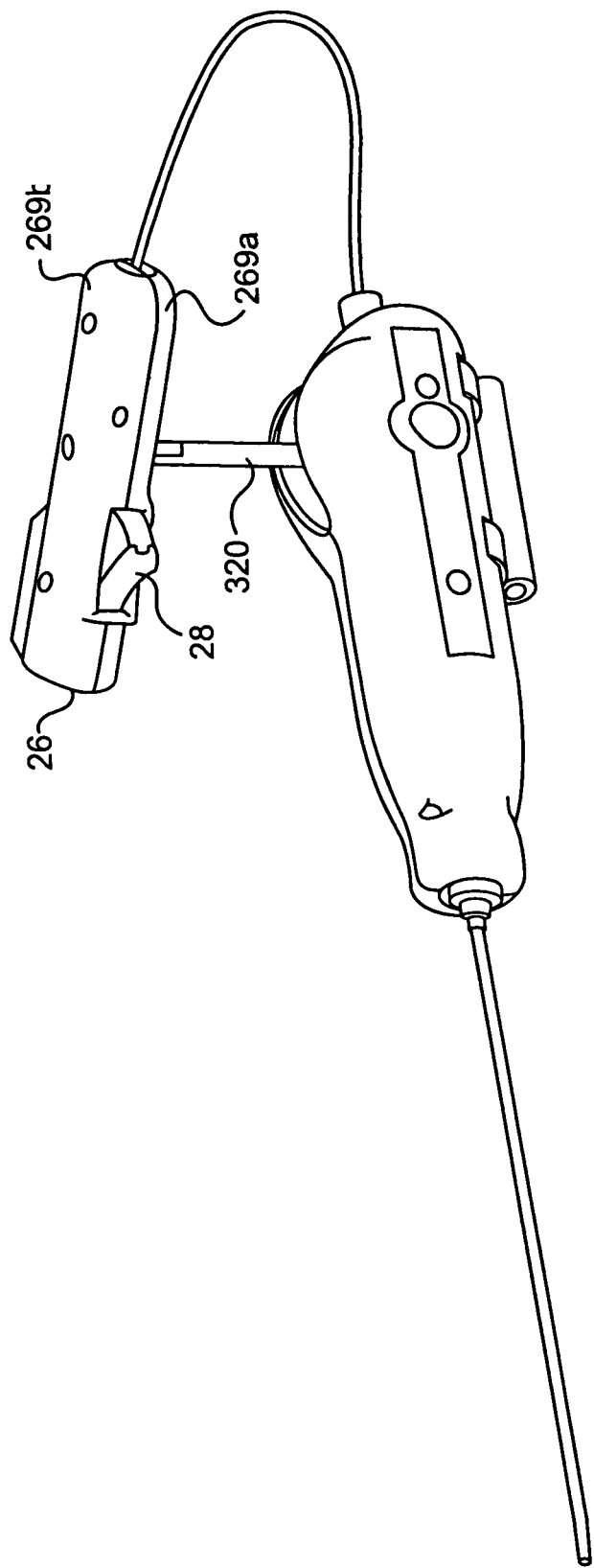

A first type of ambidextrous handle detaches from the control mechanism to permit a change in handedness. For example, the handle can be detached and flip upside down to change handedness. FIGS. 9A through 9C illustrate this concept with a tool similar to the one described with reference to FIG. 1. FIG. 9A presents the handle in a right-handed configuration. The handle 269 includes a first side 269*a* facing up and a second side 269*b* facing down. Each of the first and second sides 269*a*, 269*b* can includes mating features 339 for mating with the control stem 320. In this configuration, the trigger is positioned activation by a user's right hand index finger.

FIG. 9B illustrates handle 268 detached from stem 320 and flipped over into a left-handed orientation. The first side 269*a* now faces downward, while the second side 269*b* faces upward. The mating feature 339 on the first side 269*a* also faces downward, allowing the handle to mate with stem 320.

FIG. 9C illustrates handle 268 in the final mounted left-handed configuration. In this configuration, trigger 28 is positioned for activation by the index finger of the user's left hand.

The mating features 339 for engaging and disengaging the handle can comprise, for example, a variety of mechanical and frictional mating features. In one embodiment, the mating feature is an opening in for receiving a portion of stem 320. In another aspect, the opening extends from the top of the handle 267 to the bottom. The mating feature can also comprise a protrusion that mates with an opening in the shaft or control body. In still another embodiment, the two mating features 339 are located on the same side of the handle 267 grip, but allow for attaching with the stem 320 in order to suit different handedness.

A second type of ambidextrous handle is illustrated in FIGS. 9D and 9E. Unlike the previous type, the handle 266 can change the orientation of trigger 281 via rotating handle portion 266*a*. In addition, handle 266 can change orientation with respect to house 30 of control member 20 via rotation of handle 226 between a right-handed configuration and a left handed configuration.

In one aspect, handle 266 includes first and second handle portions 266*a* and 266*b* rotatably connect with one another via pivot 338. Rotating handle portion 266*a* with respect to 266*b*, changes the orientation of trigger 281. In addition, first handle portion 266*b* can rotatably connect to the stem or control body of the tool. Rotating handle portions 266*a*, 266*b* together around stem 320 changes the handedness of handle 266.

As illustrated in FIG. 9D, the rotatable portion 266*a* can include a push-pull mechanism 281 oriented for right-handed use. The push-pull mechanism 281 is a trigger that operates much like a scissor, and allows the user to control an end effector and/or actuate a catheter. For example, the push-pull mechanism 281 can push or pull a cable that runs through a hole in pivot 338, and down the stem 320 into the body of the control device.

By rotating both handle portions 266a and 266b by 180 degrees, as described above, the user effectively flips the push-pull mechanism 281 to a different handedness. FIG. 9D includes a stem axis (axis S-S) and handle axis (axis H-H) for further clarity. The first portion 266b and second portion 266a rotate around the stem axis, while the second portion 266a also rotates around the handle axis. As a result, the first portion 266b and the second portion 266a switch sides, as shown in FIG. 9E. The orientation of the trigger 281 also reverses because it is attached to the first portion 266a.

To allow for rotating the sections to change handedness, the handle 266 includes two switches 291 and 292 for locking/unlocking both handle portions. Switch 291 locks and unlocks the rotatable portion 266a from swiveling at the pivot 338 with angling portion 266b engaging and disengaging a first mating structure (not pictured). Switch 292 locks and unlocks the angling portion 266b of the handle 266 from the stem 320 by engaging and disengaging a second mating structure (not pictured). Potential mating structures include a tooth, pin, clamp, detent system, strap, or any other known structure for mechanically locking and inhibiting movement between two members.

In another embodiment, both portions 291 and 292 are unlocked with a single switch. As used herein, the switch can include a slide, button, or any other locking mechanism, such as a pin or screw.

The user can adjust the handle 266 to a more comfortable orientation in one embodiment by rotating the appropriate portion 266a and/or 266b. For example, the user can rotate the push-pull mechanism 281 upwards and/or manipulating the horizontal orientation of the handle grip. When the user positions the handle 266 as desired, the portions 266a and 266b are locked in place.

Figure 9F:
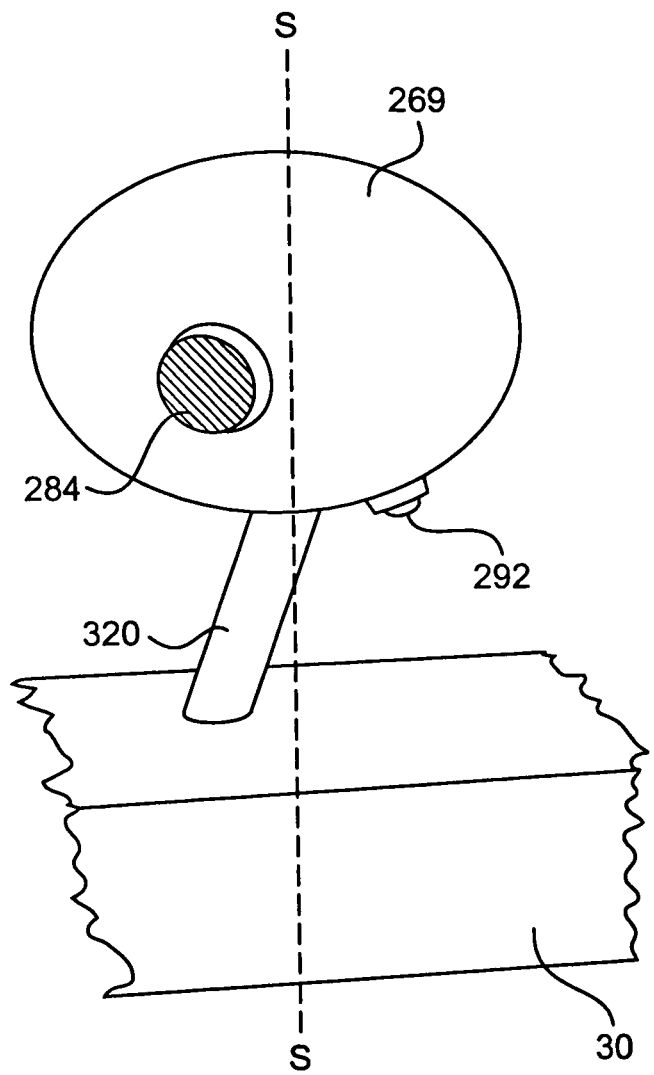
FIG. 9F is an exemplary illustration of an ambidextrous handle that can change handedness by rotating around an axis, in accordance with an embodiment.

A third type of ambidextrous handle, shown in FIG. 9F, can change handedness by rotating in only one plane. FIG. 9F illustrates a handle 269 that is round and contains a switch 284 in the form of a button. As illustrated, the handle 269 has a left-handed configuration, wherein the user controls switch 284 with their left thumb.

To change the handedness, handle 269 rotates relative to the control body 30 or stem 320. Switch 292 unlocks the handle 269 for rotation. In one embodiment, unlocking does not detach the handle 269 from the stem 320 or control body 30, but instead allows the handle 269 to rotate around the stem 320. In another embodiment, the handle 269 remains locked to the stem 320, but the handle 269 and stem 320 rotate together, relative to the control body 30. Similarly, in embodiments where no stem 320 exists, rotation may occur around some other axis, such as axis S-S. Even in embodiments that include a stem 320, such as FIG. 9F, rotation need not necessarily occur around an axis through the stem. For example, the handle 269 in FIG. 9F could alternatively rotate around axis S-S.

In an embodiment that accomplishes ambidexterity through this rotational approach, a single opening 339 can suffice for mating with the control stem.

FIGS. 9G through 9L illustrate some alternate handle embodiments that implement the rotational and detachable characteristics of handles already described. Some of these embodiments implement additional characteristics, such as a joystick configuration option.

Figure 9G:
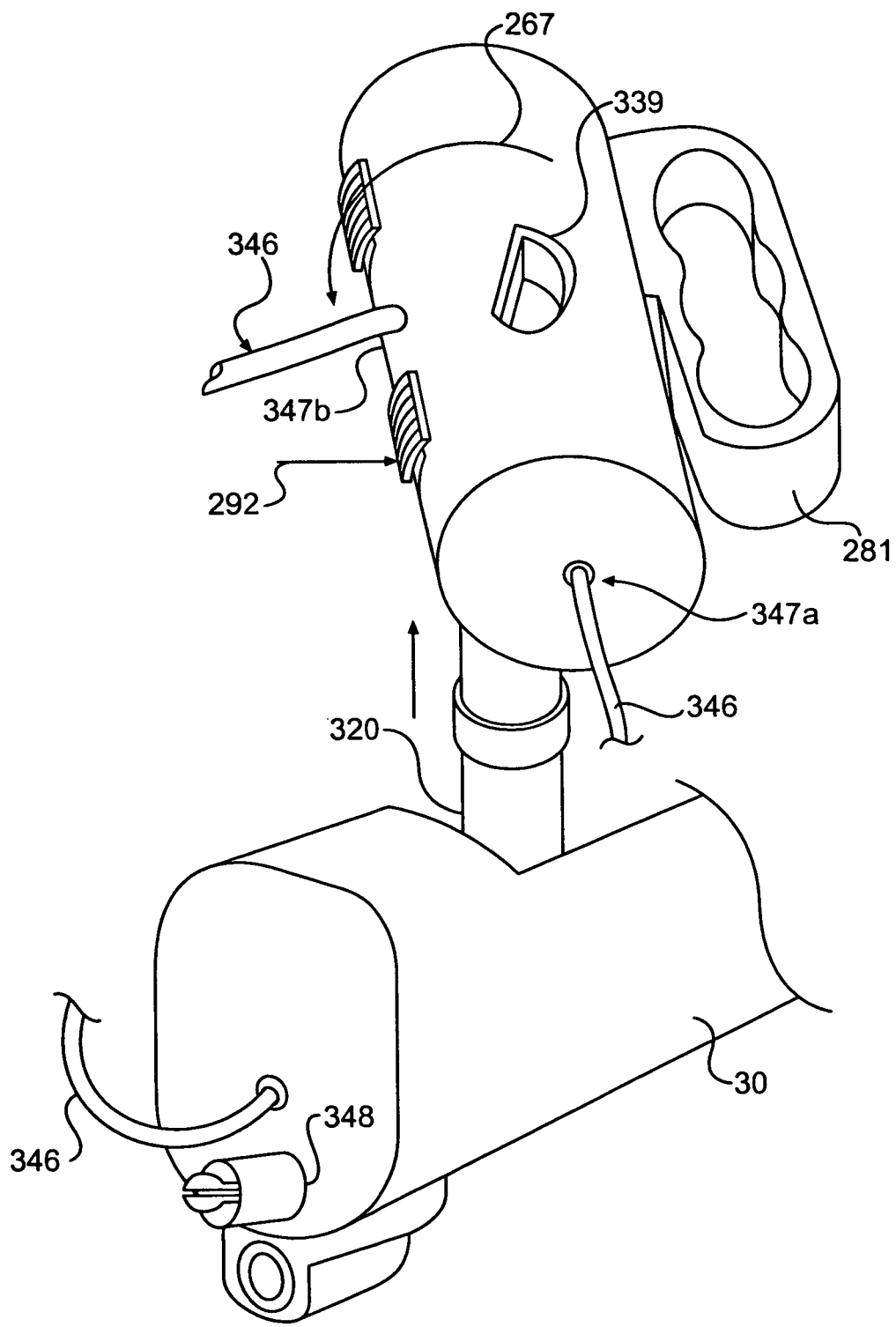
FIG. 9G is an exemplary illustration of an ambidextrous control handle that can be flipped in order to change handedness, in accordance with an embodiment.

FIG. 9G illustrates an ambidextrous handle 267 with a push-pull mechanism 281 (another type of trigger). The push-pull mechanism 281 pushes and pulls the inner-filament of cable 346, which transfers forces from the handle 267 to the end effector. As shown in FIG. 9G, the cable can exit the handle 267 from a first exit point 347a in one embodiment, or a second exit point 347b in another embodiment. An exterior cable allows the user to detach and flip the handle 267 even though handle 267 includes a trigger. In one embodiment, the trigger 281 can still be used when handle 267 is detached.

In one embodiment, the cable 346 passes though a firewall (such as described with reference to FIGS. 2H and 2I). Conversely, in another embodiment, the cable 346 passes directly from the handle to the articulation section of the catheter, without the use of the firewall.

FIG. 9G also illustrates an exemplary alternative cautery connection 348 for use in cauterization procedures. Of course, other embodiments do not implement this feature but still use the handle 267 shown in FIG. 9B.

Figure 9H:
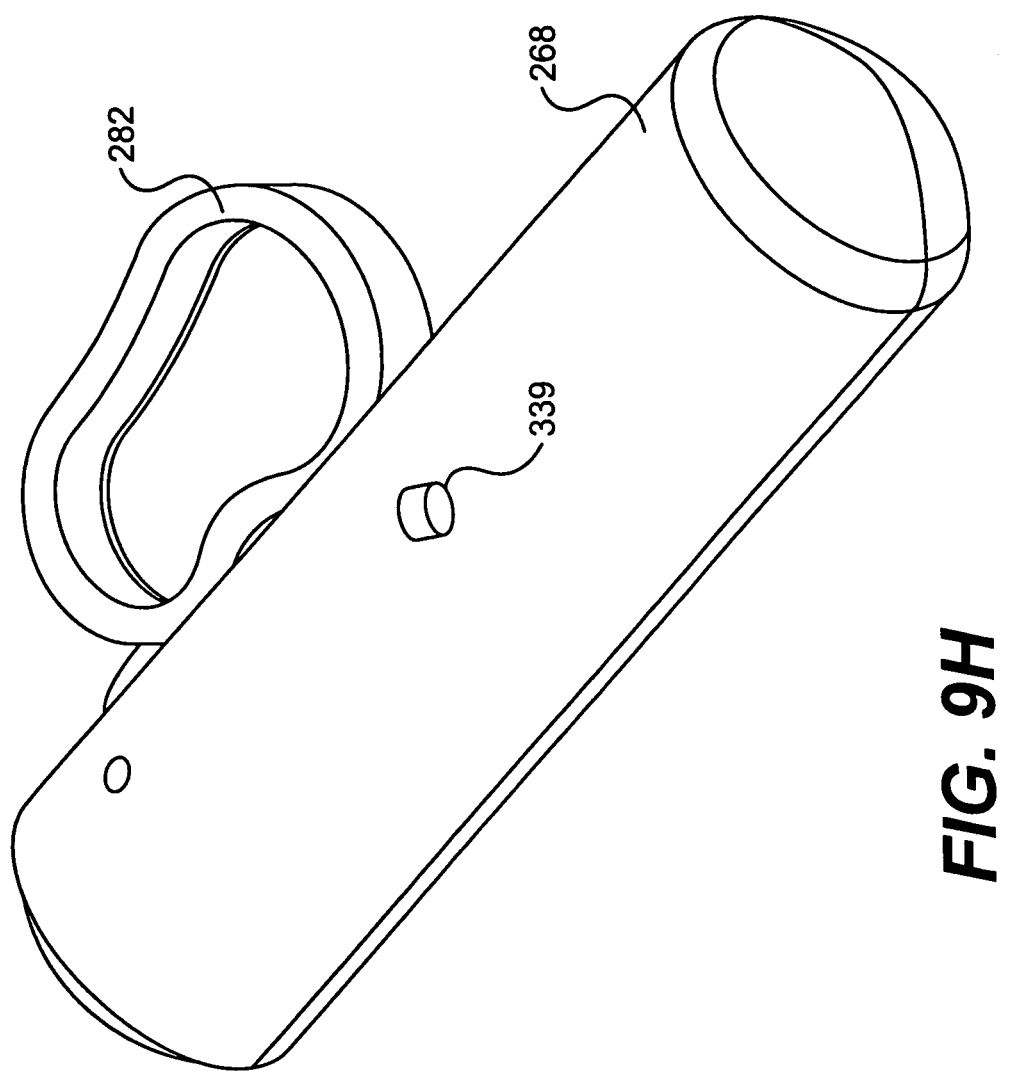
FIG. 9H is an exemplary illustration of another ambidextrous control handle that can be flipped in order to change handedness, in accordance with an embodiment.
Figure 9I:
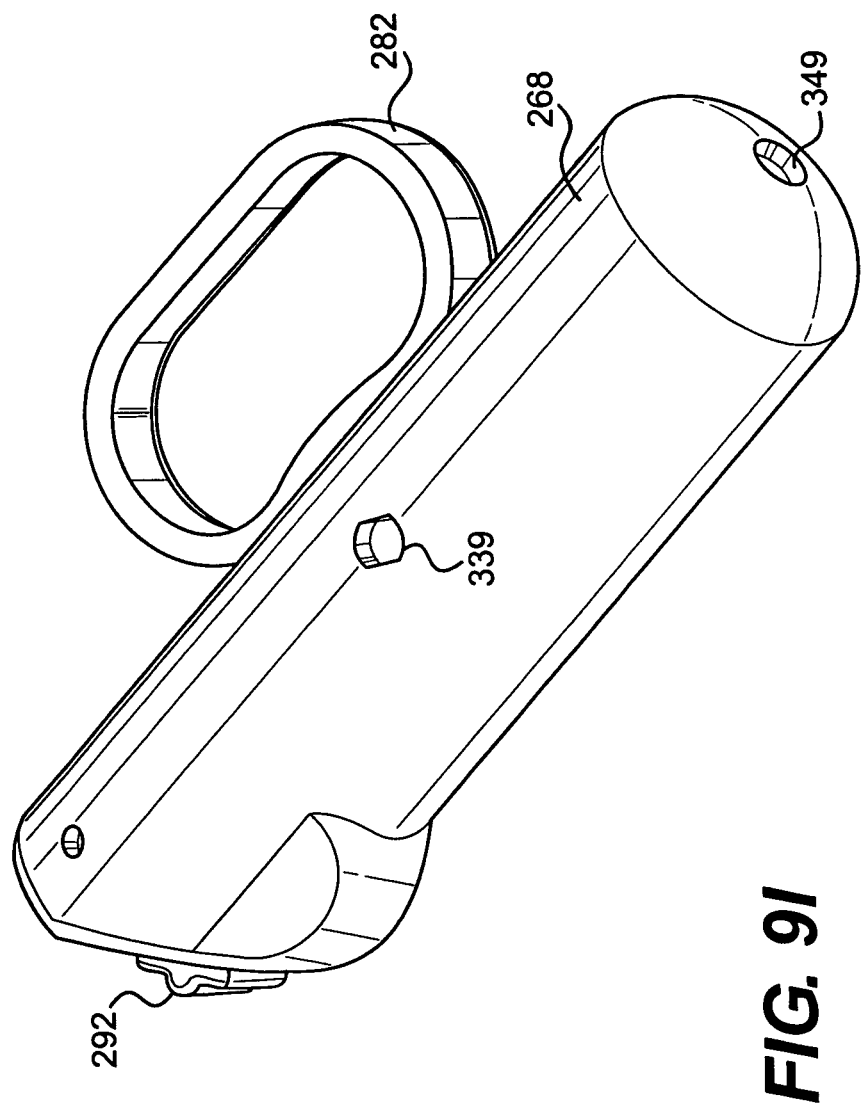
FIGS. 9I through 9K are exemplary illustrations of ambidextrous handles that can also be changed into a joystick configuration, in accordance with an embodiment.
Figure 9J:
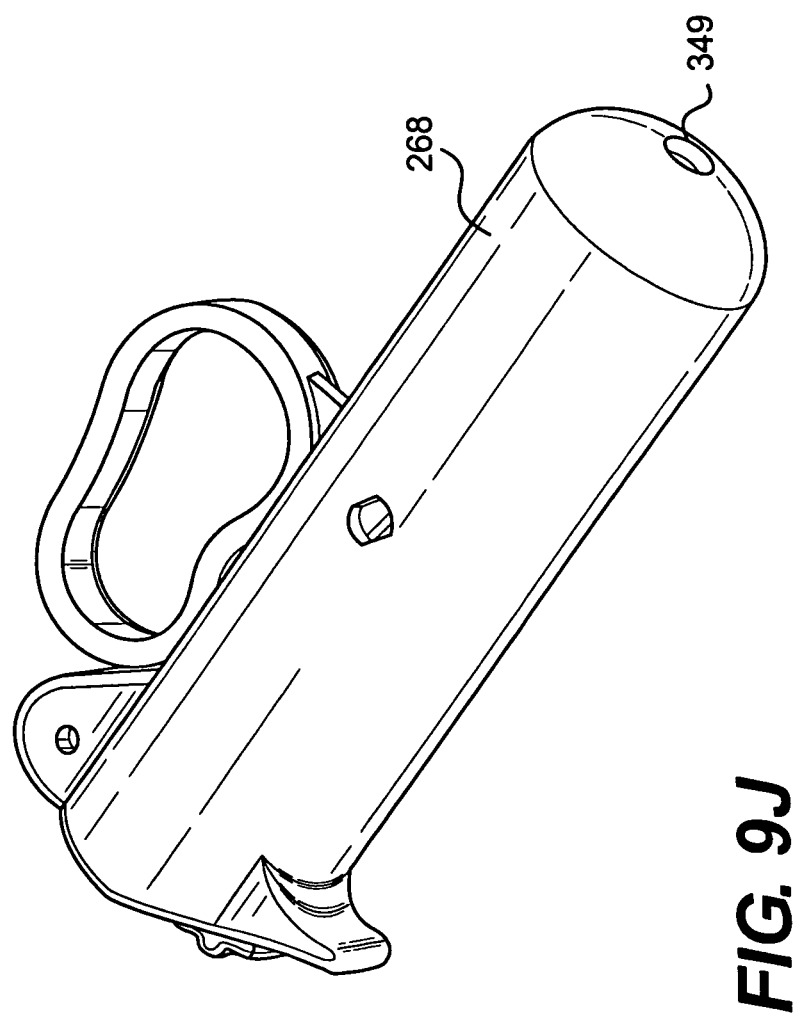

FIG. 9H illustrates a handle 268 that can change handedness by either detaching and flipping or by simply rotating relative to the stem. Because the trigger 282 and handle 268 can conform to either hand without being flipped vertically, rotating the handle with respect the stem reorients the handle. Similarly, flipping the handle vertically also switches the handedness.

The handles 268 illustrated in FIGS. 9I through 9L provide even further flexibility by providing an additional opening 349 to allow the user to stand the handle on end in joystick configuration. The user may, therefore, select to operate the handle 268 with the grip laying flat by connecting the handle at opening 339, or as a joystick by connecting to the stem at opening 349. As previously described, switch 292 locks and unlocks the handle 268 from the control stem.

Figure 9K:
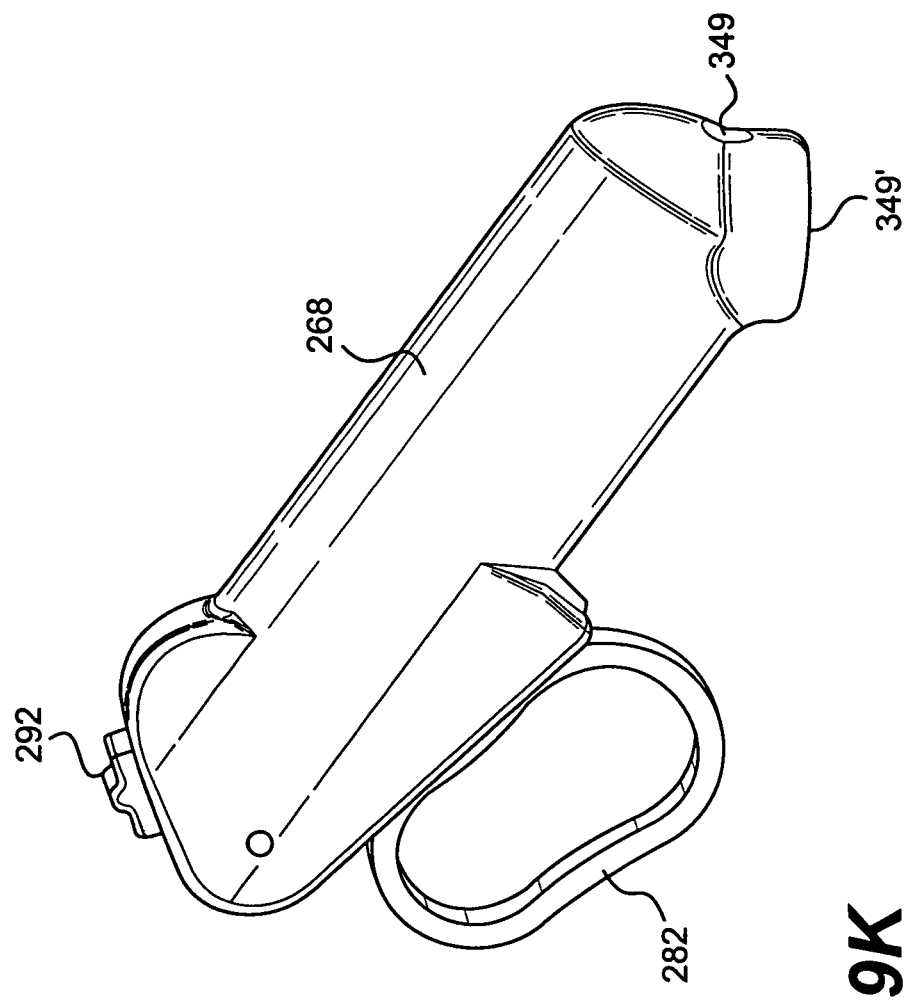

FIG. 9k illustrates a handle 268 that includes a mating feature 349' at the bottom of a rounded boss. This mating feature puts the handle 268 in pistol grip configuration, which is another type of joystick configuration. Handle 268 also includes an alternate mating feature 349 for yet another joystick configuration.

Figure 9L:
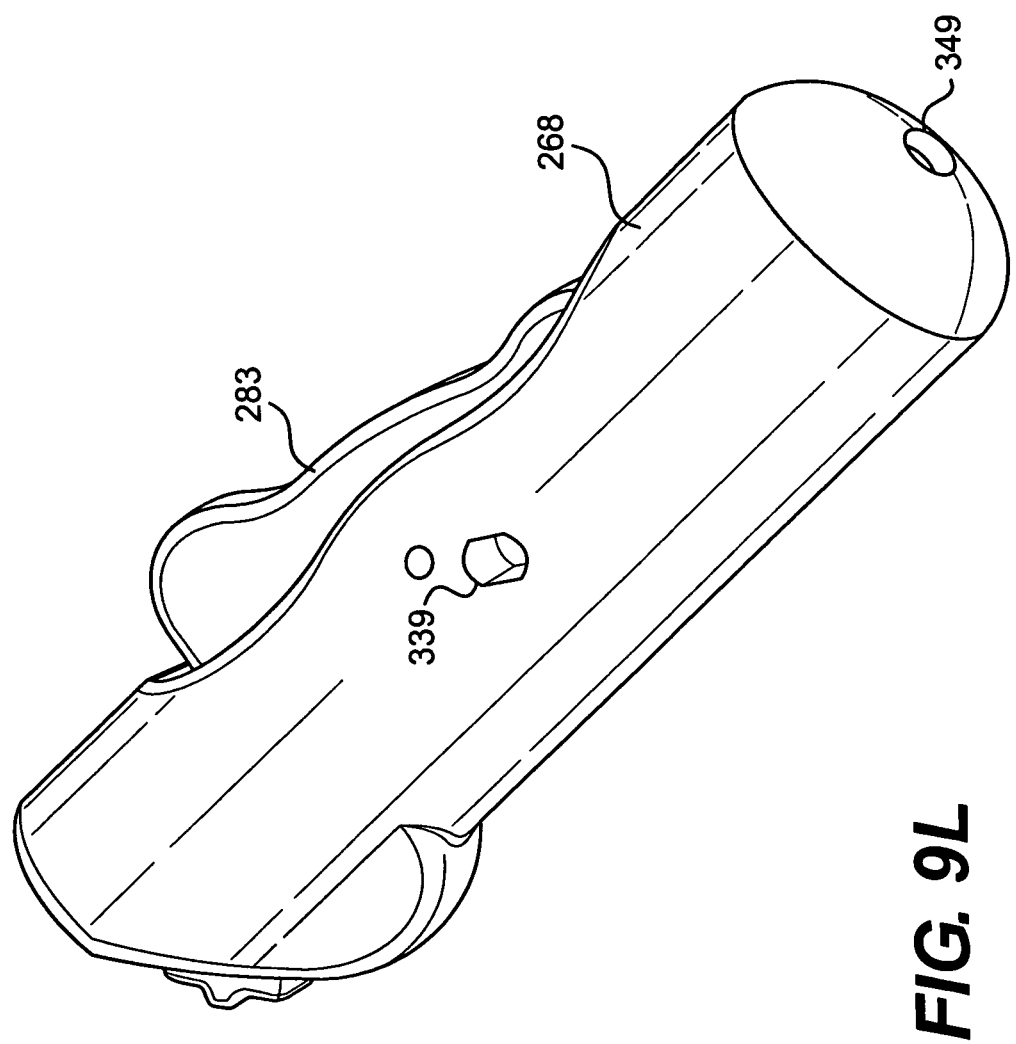
FIG. 9L is an exemplary illustration of a handle that can change between joystick configuration and side configuration, also including a rocker mechanism, in accordance with an embodiment.

FIG. 9L illustrates an ambidextrous handle 268 that can be flipped for orientation with either hand, and, alternatively, stood on its end in a joystick configuration.

The illustrated handle 268 includes a rocker mechanism 283, which is yet another type of trigger. The rocker mechanism 282 allows a user to articulate the end effector and/or articulation section of a catheter by performing a rocking motion. Rather than swinging outward like a scissor, the rocker mechanism 282 incorporates a see-saw action, such that pushing one side down forces the other side up. The rocker mechanism 282 can be spring-loaded for returning to a home position. Conversely, in another embodiment, the rocker remains in its last position until adjusted by the user.

The Catheter

Figure 10A:
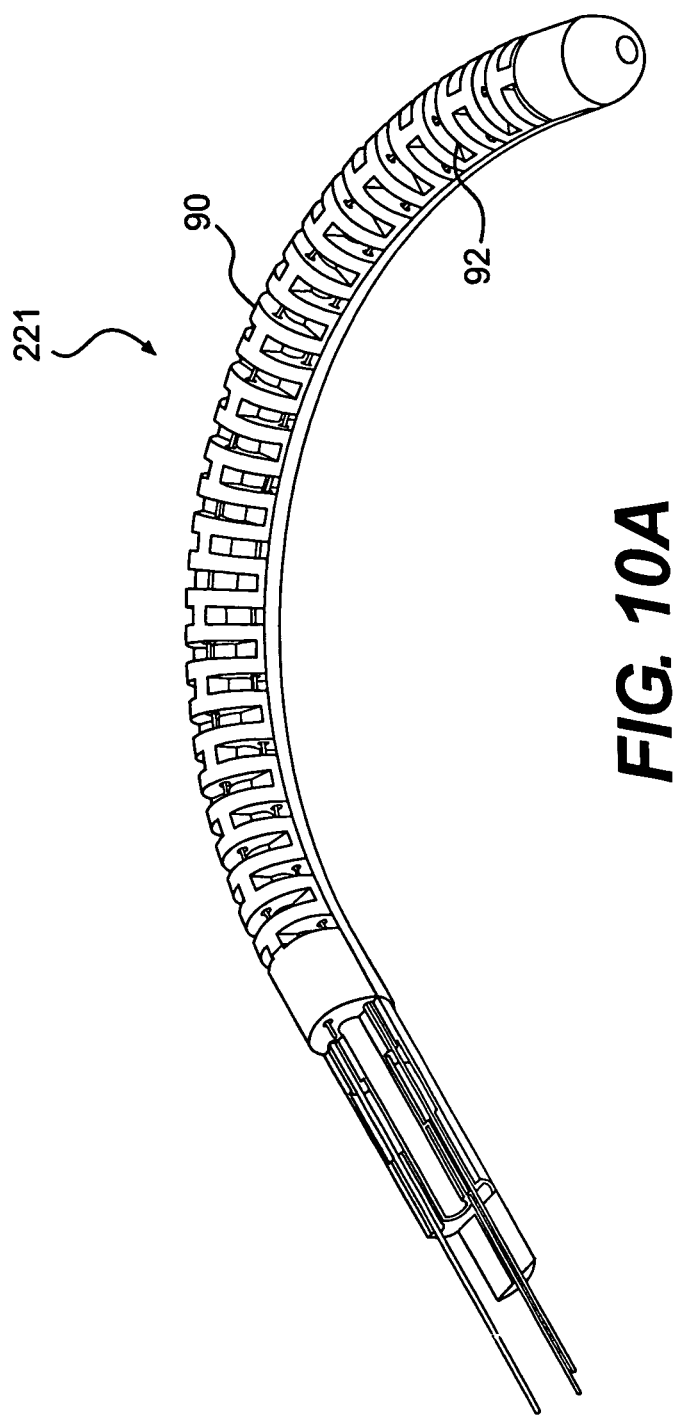
FIGS. 10A through 10C are exemplary illustrations of a catheter having a continuous body section with cut-outs that allow for articulation, in accordance with an embodiment.
Figure 10B:
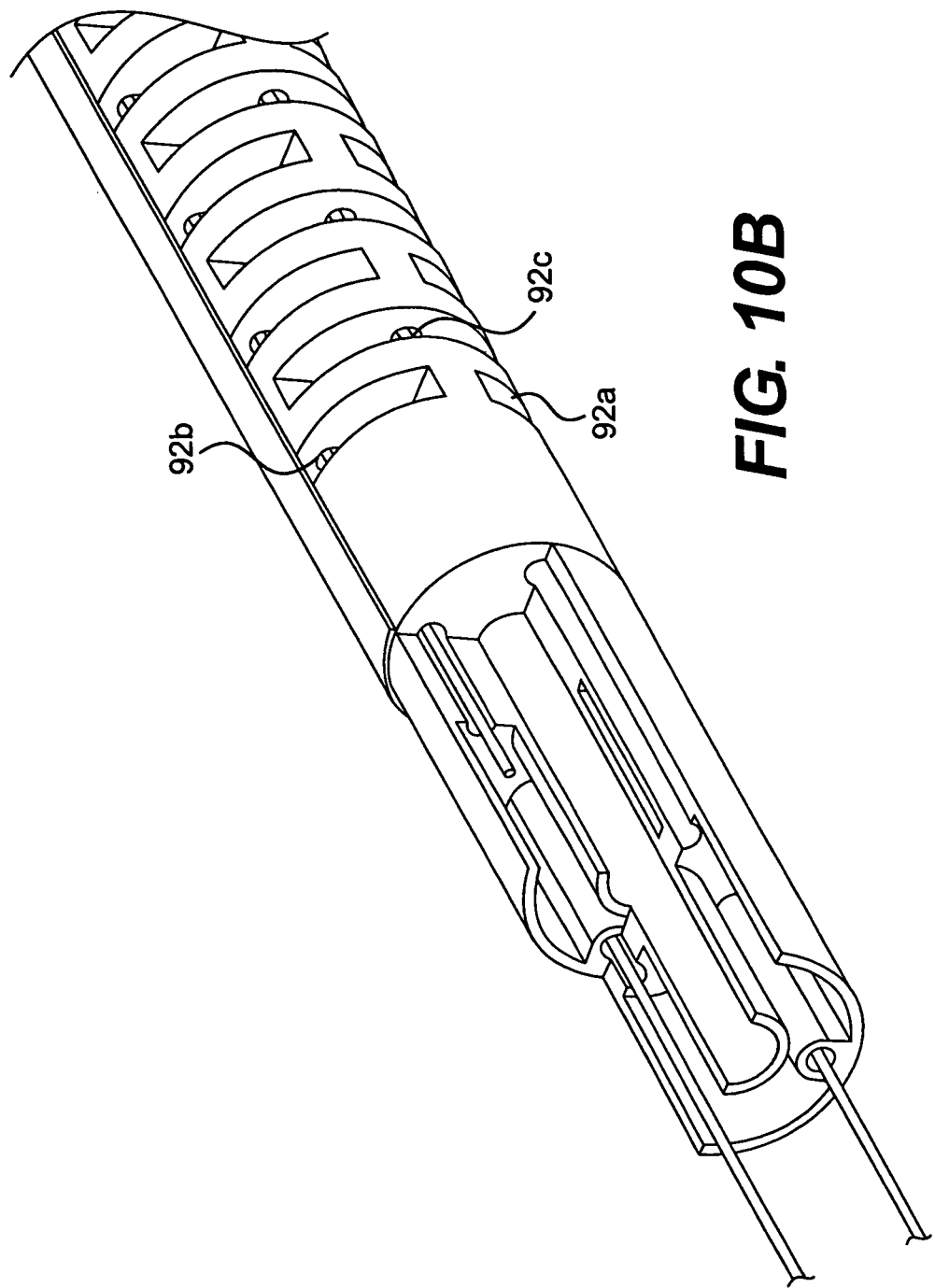
Figure 10C:
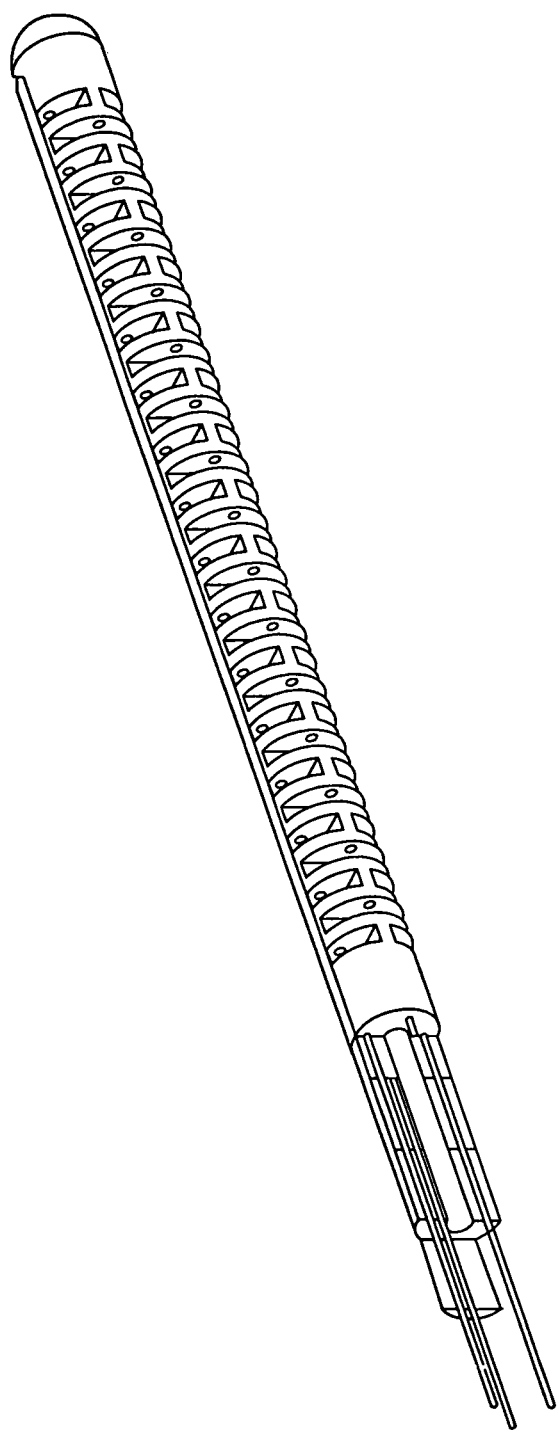

Further described herein are alternative configurations of the catheter. In one aspect, catheter 221 includes body 90 configured to provide increased torsional strength. As shown in FIGS. 10A through 10C, catheter 221 can include a continuous body section having cut-outs 92 to permit (or ease) flexing and/or bending. The catheter includes a series of opposing cut-out sections 92a, 92b (FIG. 10B) with each pair of opposing cut-outs adjacent another pair of opposing cut-outs 92c, 92d (FIG. 10B, 92d not illustrated) positioned at an angle with respect thereto. In one aspect, adjacent cut-out pairs are offset by about 90 degrees. In particular, side cut-out pairs 92c, 92d are positioned adjacent to top-bottom cut-out pairs 92a, 92b. The cut-outs permit bending while the remaining body between the cut-outs can transfer torsional loads.

Figure 11A:
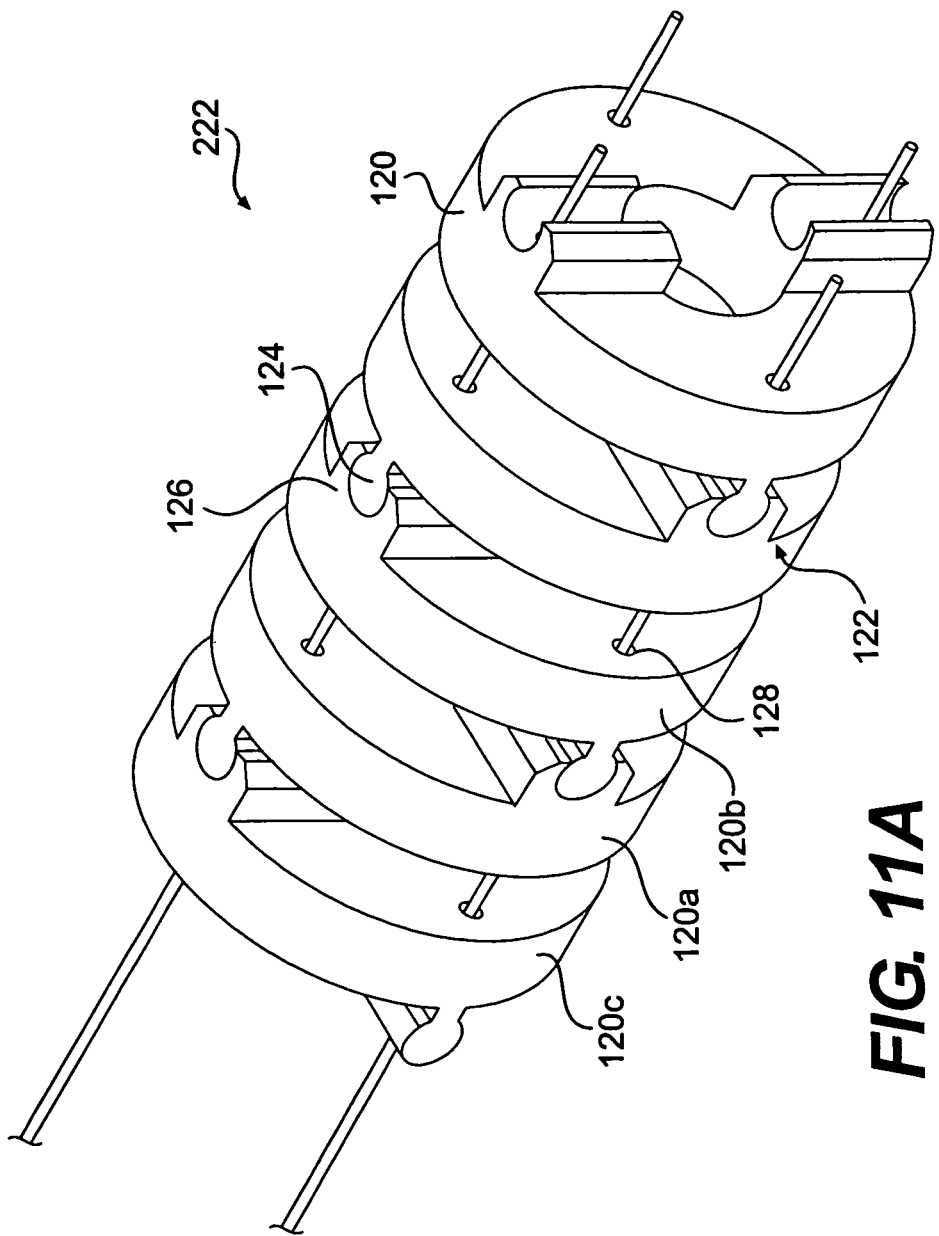
FIGS. 11A through 11C are exemplary illustrations of a catheter having multiple articulating ball sockets, in accordance with an embodiment.
Figure 11B:
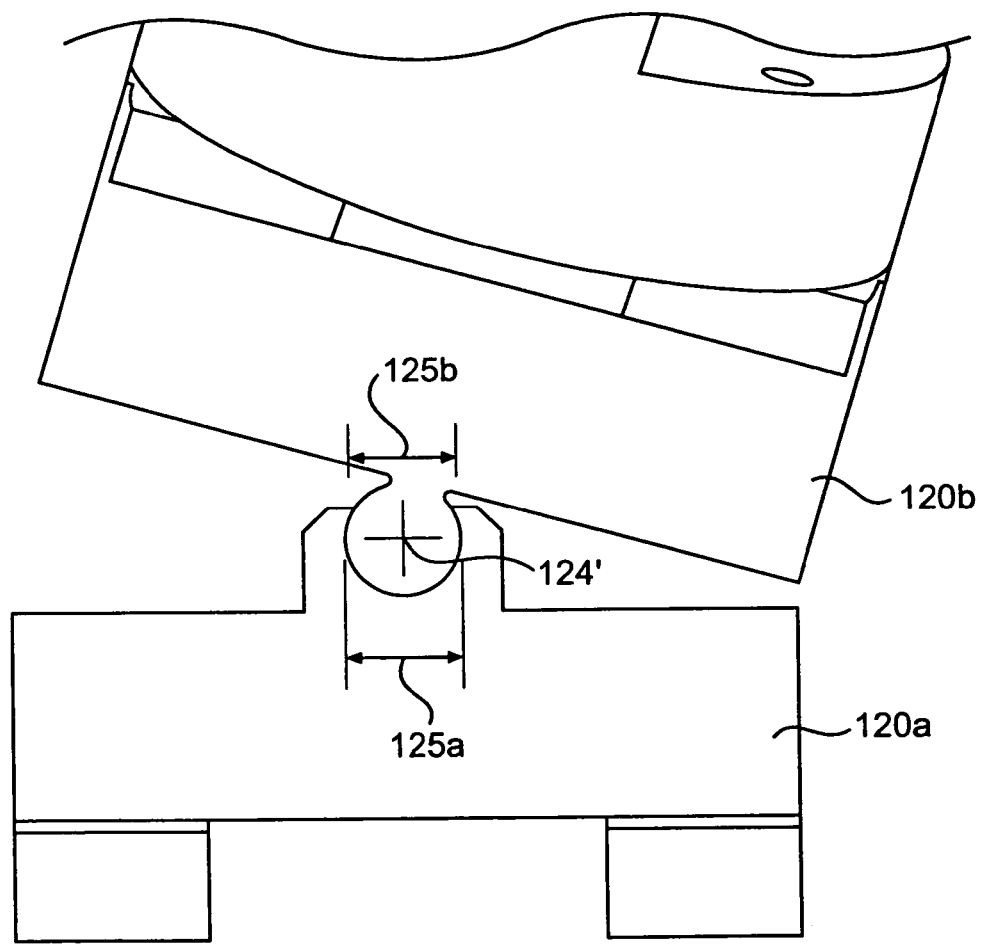
Figure 11C:
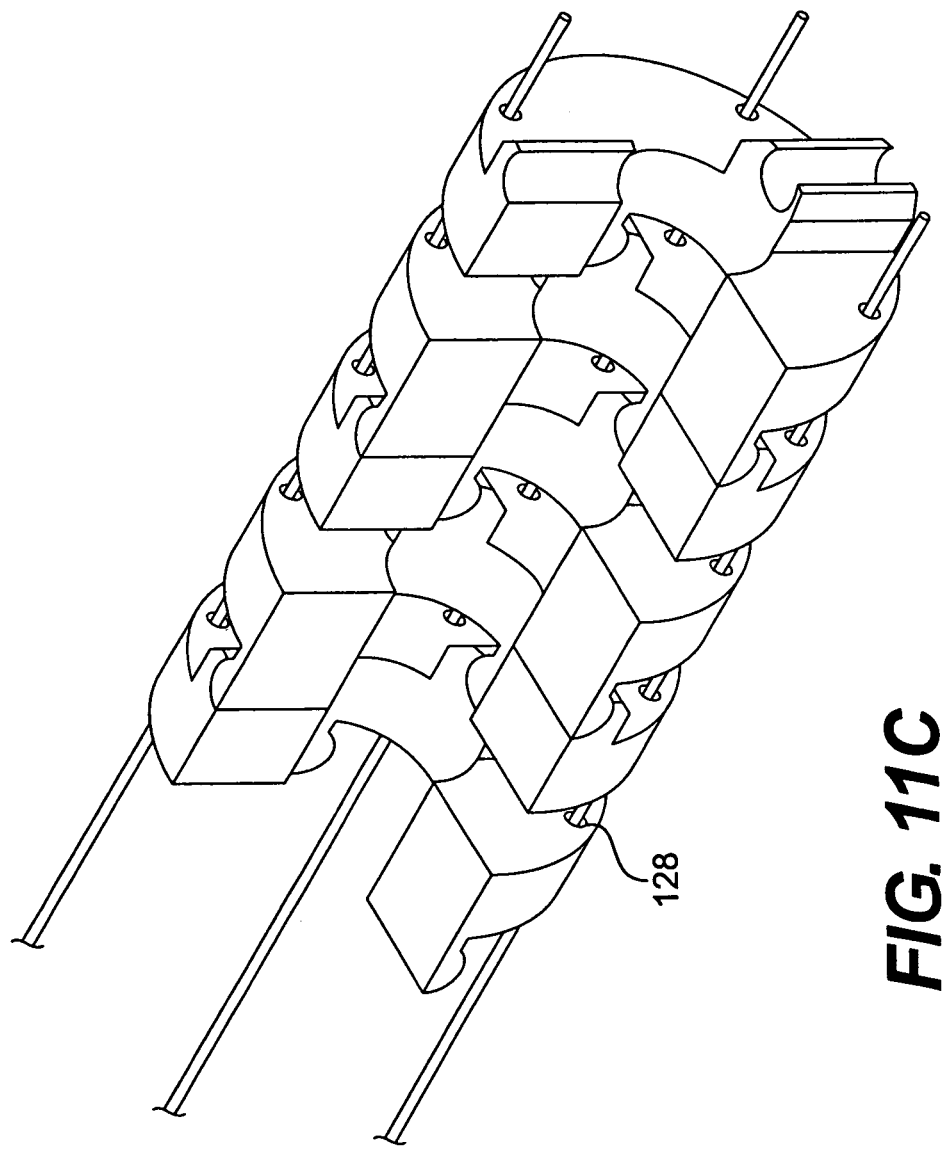

In another embodiment, catheter 222 can transmit torsional loads via mechanical interlocks between adjacent catheter body segments. FIGS. 11A through 11C illustrate segments 120 having articulating mechanical interlocks 122. The interlocks allow pivoting but do not allow rotation and/or translation of the segments with respect to one another. In other words, the mechanical interlocks limit at least one degree of freedom between adjacent catheter body segments 120.

In one aspect, mechanical interlocks 122 include a male-female connection that permits only one degree of freedom. For example, male mating member 124 can have an elongate, curved outer surface that is received in an elongate female mating member 126 having a corresponding shape. While interlocked, the male mating member can pivot within the female mating member along an axis parallel to the elongate male and female mating members. However, the male-female interlock can inhibit pivotal movement on other axes. In addition, the male-female interlock can inhibit relative rotational, longitudinal, and/or transverse movement between the adjacent segments.

For example, with respect to segments 120a, 120b (FIG. 11A) the mechanical interlocks permit up-down pivoting, but not side-to-side pivoting. Conversely, adjacent segment 120c can pivot side-to-side with respect to segment 120a, but the mechanical interlock between segments 120a and 120c prevent up-down pivoting. Taken together, the segments of catheter 222 permit up-down and side-to-side articulation, but inhibit at least rotational movement between the segments. In this way, the segments maintain torsional integrity throughout the length of catheter 222.

FIG. 11B shows a close-up side view of a ball socket (e.g., mechanical interlock). The socket of segment 120a holds the curved member of segment 120b in place by extending past the center point 124' of the curved member. In this way, the socket wraps more than half way around the curved member. As a result, the width of the socket opening 125b is less than the greatest diameter of the curved member 125a.

In addition, the curved member can be held in place laterally by the incorporation of one or more stops. For example, a socket can have an inner wall that contacts the side of the curved member. In one embodiment, the contacted inner side of the curved member is flat. Providing an inner wall on the matching socket at the other side of the same segment can prevent the connected segment from sliding loose laterally. Alternatively or in addition, a stop can exist on the outer side of the curved member. The outer stop can also integrate with the socket in one embodiment.

An over sheath can also prevent slippage or separation of the segments 102a and 120b. The over sheath may be an elongate bendable layer that surrounds the exterior of the segments. In addition to holding properties, the over sheath can prevent pinching when the catheter articulates.

In one embodiment, the segments include one or more holes 128 for receiving a cable. The holes 128 of each segment align such that the cable can be threaded though multiple sections over an articulation section. When the cable is pulled from the proximal end of the catheter, such as by the control mechanism, the segment(s) bend within the articulation section. In one embodiment, the articulation section can bend in multiple directions (e.g., left/right, up/down).

In another embodiment, the articulation section is comprised of at least one bendable and torque stable segment. While the segment(s) can be articulated from side to side and front to back, they remain rotationally rigid so that the end effector better withstands torsional forces.

Figures 12A, 12B, 12C, 12D, 12E:
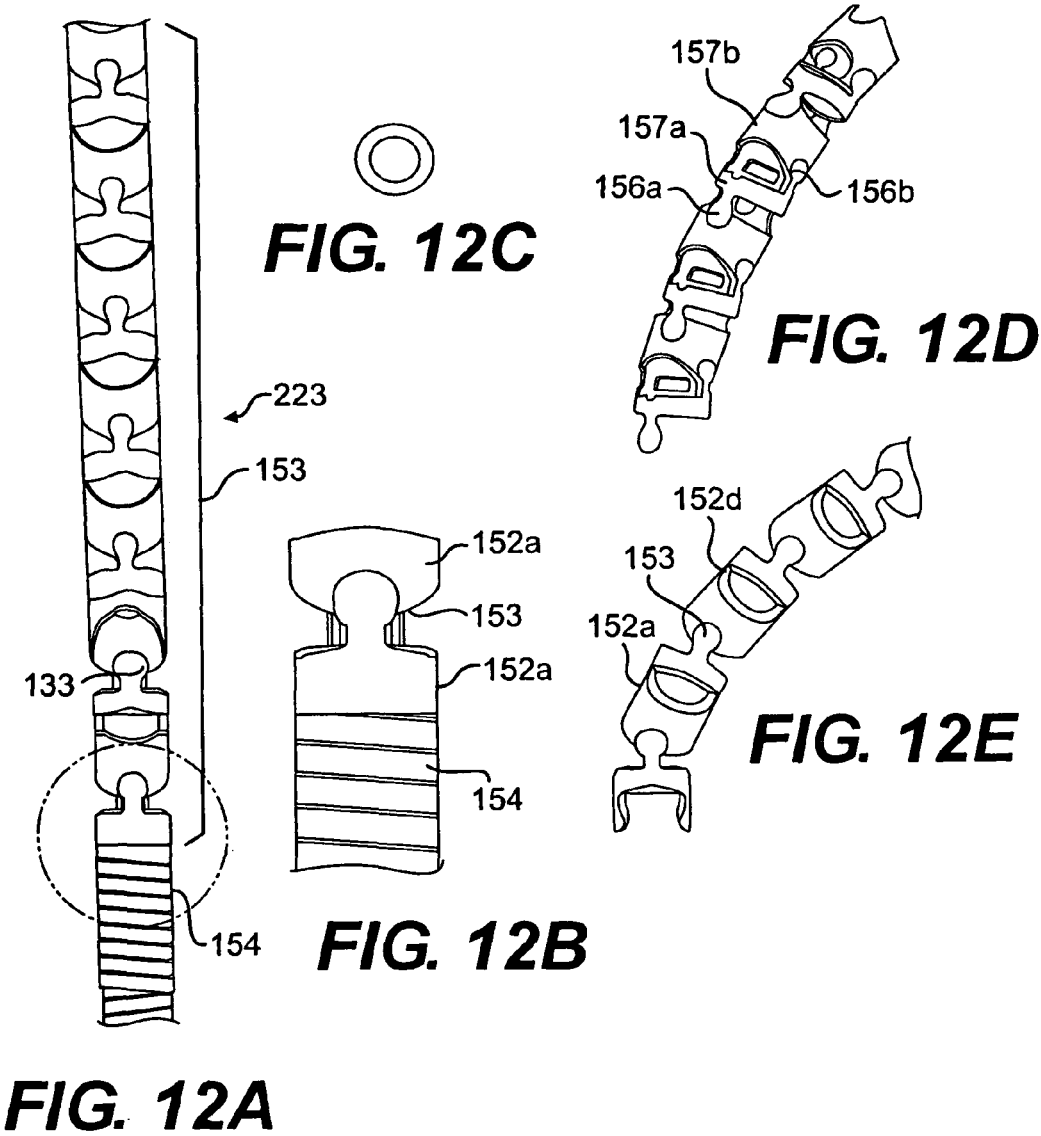
FIGS. 12A through 12G are exemplary illustrations of catheters having additional types of multiple articulating ball sockets, in accordance with an embodiment.

FIGS. 12A through 12E illustrate another embodiment of a catheter 223 utilizing mechanical interlocks for at least one degree of freedom. In FIG. 12A, the catheter includes an articulation section 155 and a rigid section 154. When a user manipulates the handle of tool 10, and articulates the catheter 223, articulation occurs along the articulation section 155. The articulation section includes multiple joint segments mechanically interlocked via entrapping balls 153. Cables 133 or other structures apply the tension to flex the articulation joints. An over braid or other sheath covers the articulation joints to prevent pinching when the articulation joints flex.

FIG. 12B shows this arrangement in detail. The articulation section 155 begins with a first joint segment 152a interlocked with a second joint segment 152b. The entrapping ball 153 fits within a socket pivot point in second joint segment 152b. By repeating this arrangement down the length of the articulation section 223, a chain of joint segments allow torque transfer from one segment to another. As a result, the articulation section achieves at least one degree of freedom.

In one embodiment, such as shown in FIG. 12C, the joint segments have a recess or opening defining a passageway. Through this passageway, one or more push-pull cables, electrical cables, lumens, and/or other tubing can access the end effector. In another embodiment, the joint segments are divided into quadrants.

While the articulation joints of FIG. 12E allow only side-to-side movement of the articulation section 223, FIG. 12D depicts multiple joint segments interlocked via entrapping balls 156a and 156b that allow for movement in two different planes. The articulation joints illustrated in FIG. 12D alternate in type. For example, segment 157a includes two entrapping balls 156a and 156b, one on each side, for movement in two separate planes. Conversely, the next segment 157b contains no entrapping balls but has two mating sockets, one on each side, for connecting with the entrapping balls in two different planes.

The catheter can be driven by user inputs. These inputs drive the articulation section in one embodiment. In another embodiment, portions of the catheter other than the articulation section can also be driven. Articulation does not require bending separate parts. Instead, it more broadly refers to the bending of the body as a whole.

The articulation section of FIGS. 12A though 12E can be constructed by micro-welding the segments together. Entrapping the ball and socket reduces the chances of segments slipping loose from one another, and also provides a low cost articulation section because other parts are not necessarily required. Preferably, each socket entraps the ball for more than 180 degrees, as shown in FIGS. 12A through 12E.

Figure 12G:
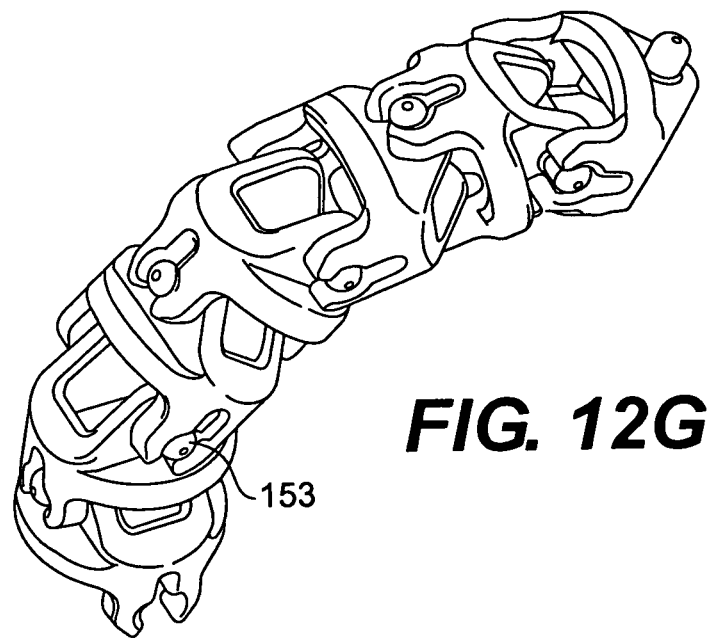
Figure 12F:
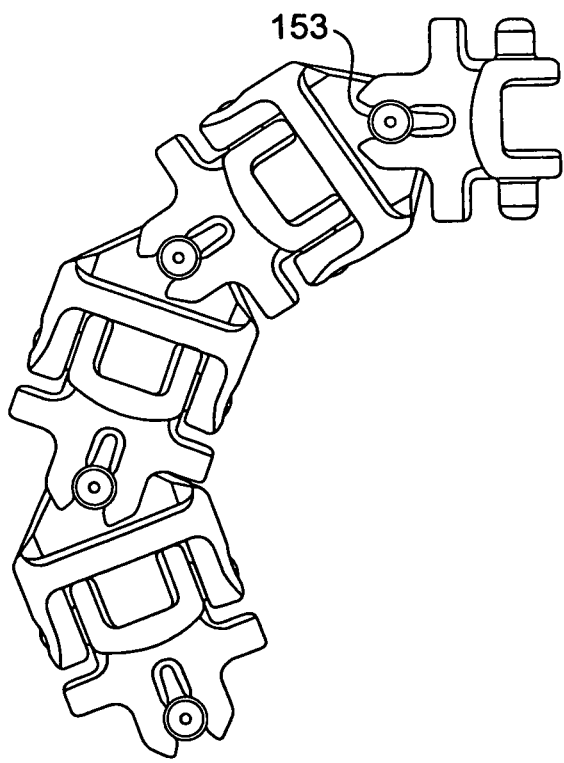

FIGS. 12F and 12G illustrate another type of ball socket system. Curved member 153 snaps into a socket. Thus, the catheter can be constructed from snapping together the segments. In addition, the segment body provides inner stops to keep the segments from sliding laterally.

Figure 13B:
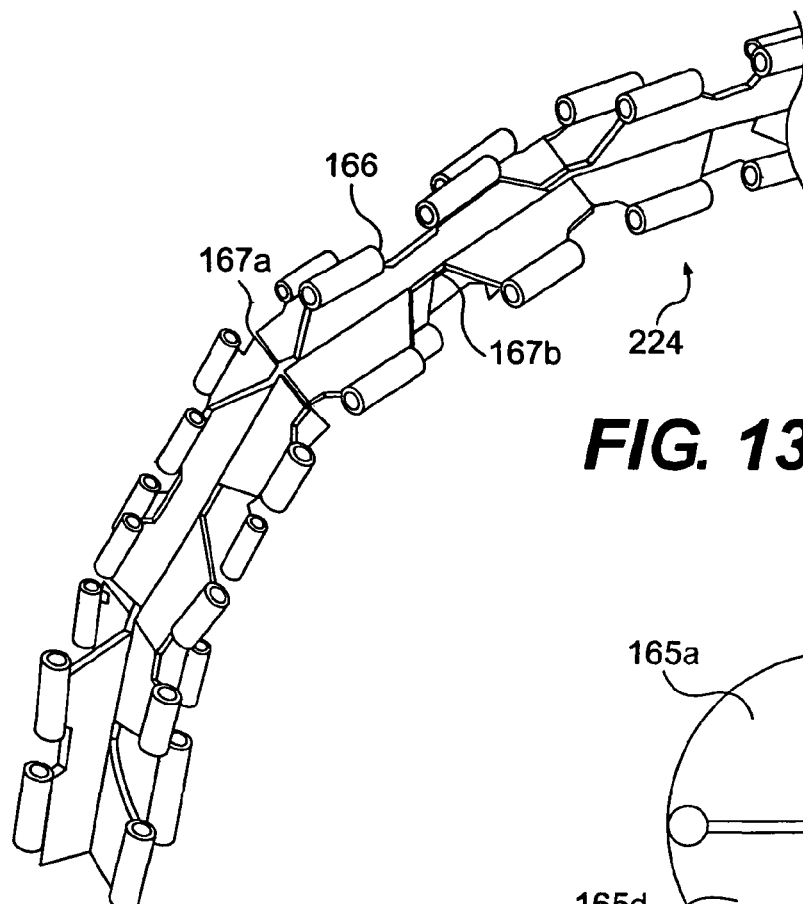
FIGS. 13A through 13D are exemplary illustrations of catheters having articulation joints, in accordance with an embodiment.
Figure 13A:
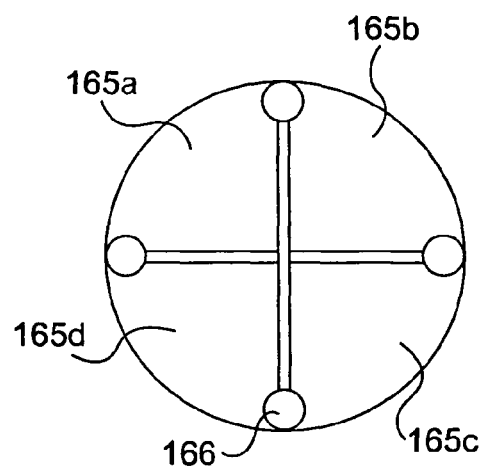
Figure 13C:
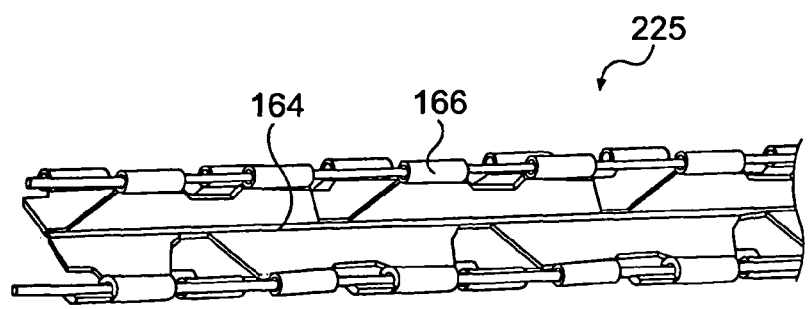
Figure 13D:
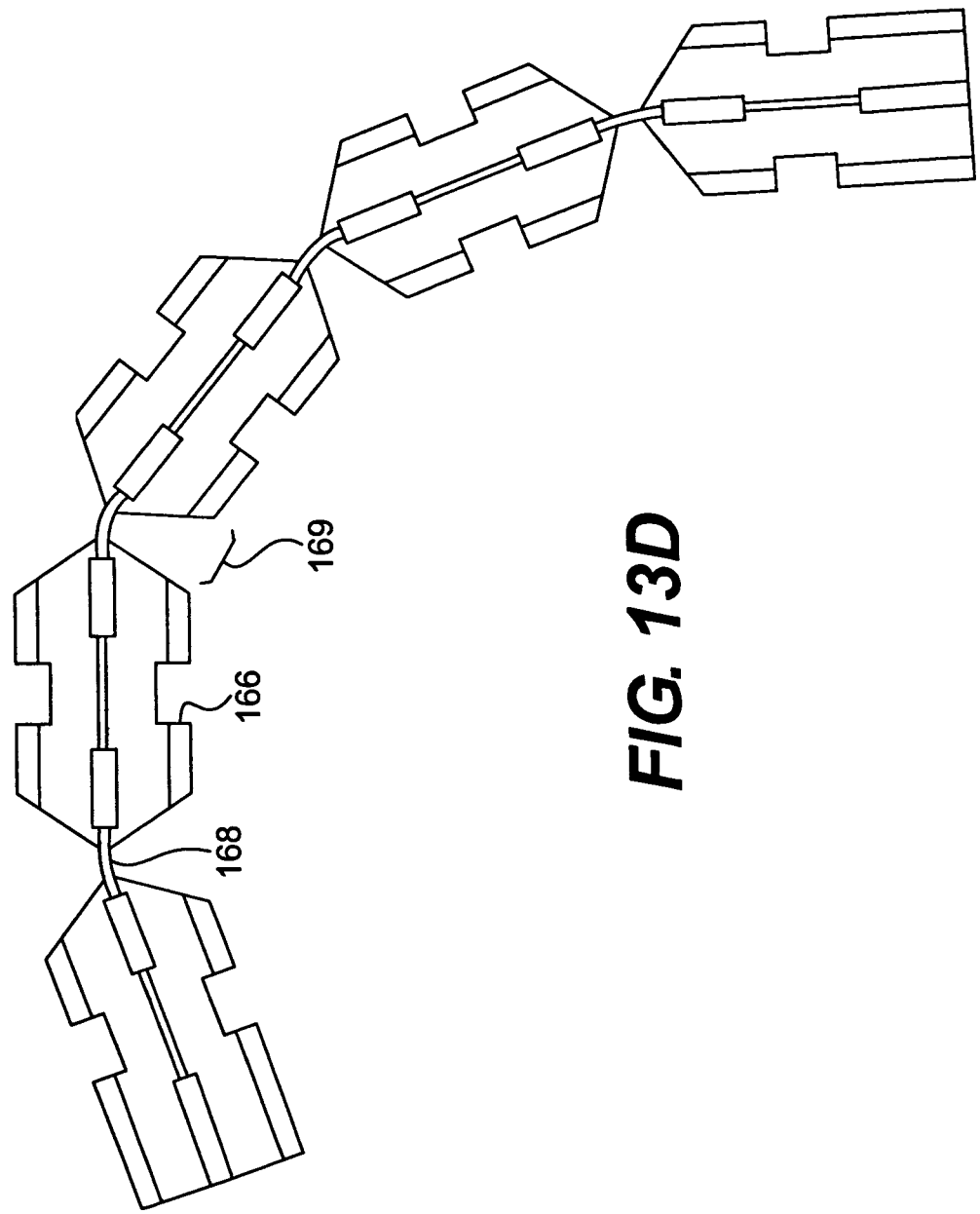

FIGS. 13A through 13D illustrate yet another type of articulation joint for use in a catheter. FIG. 13A shows the cross section of a continuous structure 225 (or series of structures), which forms a cross shape, dividing the inside of the catheter into four quadrants 165a, 165b, 165c, and 165d. The quadrants can define lumens or channels within the catheter for the passage of control cables, medical devices, and/or fluids. Eyelets 166 along the periphery of the structures receive control cables for articulating the catheter.

The articulation segments of FIGS. 13A to 13D are fixedly mated with one another and/or formed of a single, continuous structure 225 (or series of structures) that bends at hinges 167*a* and 167*b*. In one aspect, hinges 167*a*, 167*b* are defined by living hinges. For example, areas of thin cross-section allow bending between adjacent segments and define the individual segments. The articulation joint materials and hinge construction (e.g., thickness) can be selected based on the desired force-to-bend ratio for the catheter. Suitable materials for constructing the articulation joints include stainless spring steel. Possible fabrication methods include precision stamping strips of metal or laser cutting the metal and then micro welding the strips together.

The degrees of freedom are controlled based on the position of the hinges within body 164. In one aspect, each hinge only allow for bending in one plane with adjacent hinges offset from one another. For example, a first hinge 167*a* can permit up/down movement, while a second hinge 167*b* can permit left/right movement. The shape segments and/or the hinges can control maximum bending limits for the catheter. For example, to restrict bending, the space 169 between adjacent segments can be narrowed.

A multidirectional hinge is also possible if the continuous structure 225 is thin in both planes at point 168.

Figure 14D:
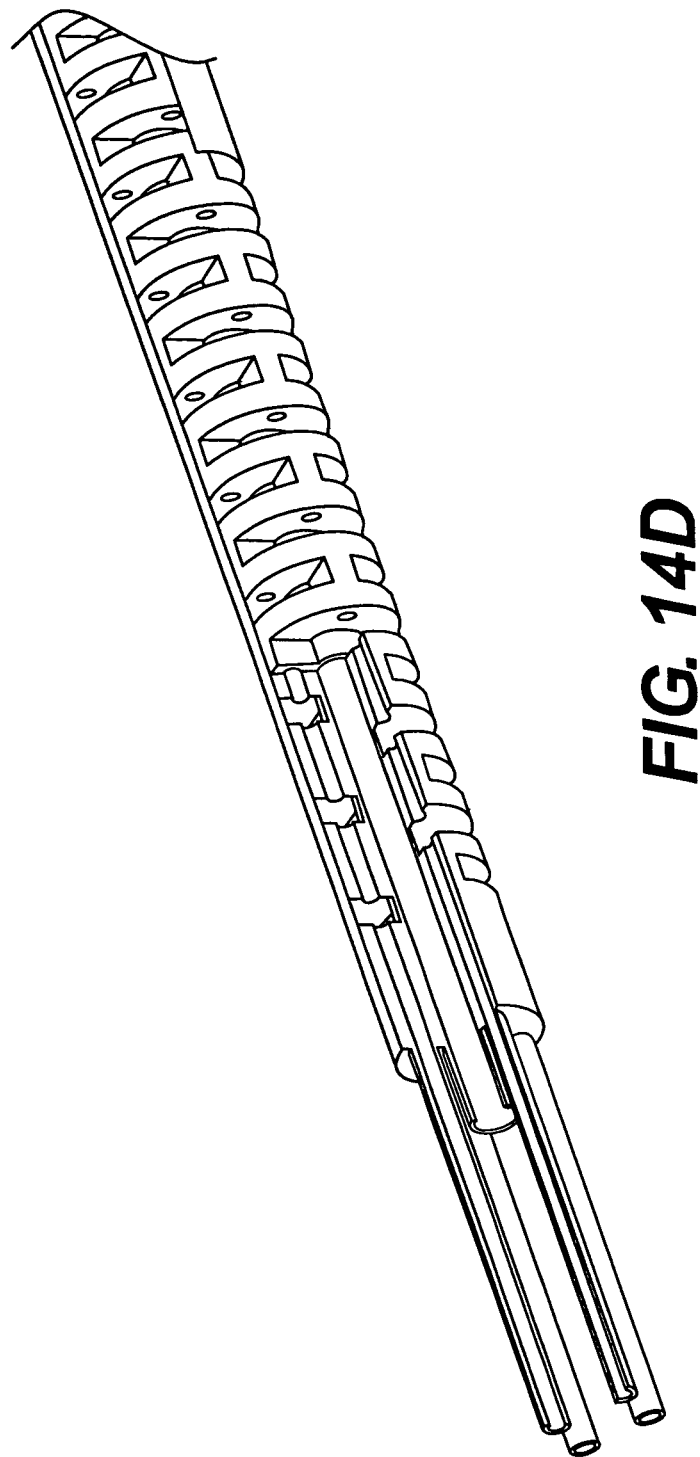

FIGS. 14A through 14E illustrate another embodiment of tool 10 including hydraulic control of at least one degree of freedom. In one aspect, catheter 223 includes at least one fluid pathway that can receive a hydraulic fluid (e.g., generally any fluid and not necessarily "industrial" hydraulic fluids) to control one degree of freedom. In another aspect, two fluid pathways can be formed in catheter 223. As shown in FIG. 14A, device 10 can include two fluid actuators 130*a*, 130*b*, each fluid actuator corresponding to two fluid pathways 132*a*, 132*b* and 132*c*, 132*d*, respectively. The fluid actuators 130*a*, 130*b* can deliver and withdraw fluid to cause expansion of the volume of at least one of the fluid pathways and thereby cause catheter 223 to bend.

For example, when a piston head 131*a* of fluid actuator 130*a* is pressed inward and moves distally within fluid actuator 130*a*, the piston head 131*a* forces fluid out of the fluid actuator 130*a* and into fluid pathway 132*a*. While the amount of fluid in the fluid actuator 130*a* on the distal side of the piston head 131*a* decreases, the amount of fluid in the fluid pathway 132*a* increases. Simultaneously, this piston head 131*a* movement draws fluid out of fluid pathway 132*b*, and into fluid actuator 131*a* on the proximal side of piston head 131*a*.

FIG. 14B illustrates a cross-sectional view of one exemplary aspect of catheter 223. Each fluid pathway 132*a*, 132*b*, 132*c*, 132*d* can be positioned in different quadrants of the catheter. When the volume of fluid within one of the fluid pathways increases, the length of the portion of catheter which the fluid pathway occupies will increase causing the catheter to bend. Similarly, withdrawing fluid will cause a reduction in the length of one side of the catheter 223 and a bending toward the reduced-volume fluid pathway.

Figure 14E:
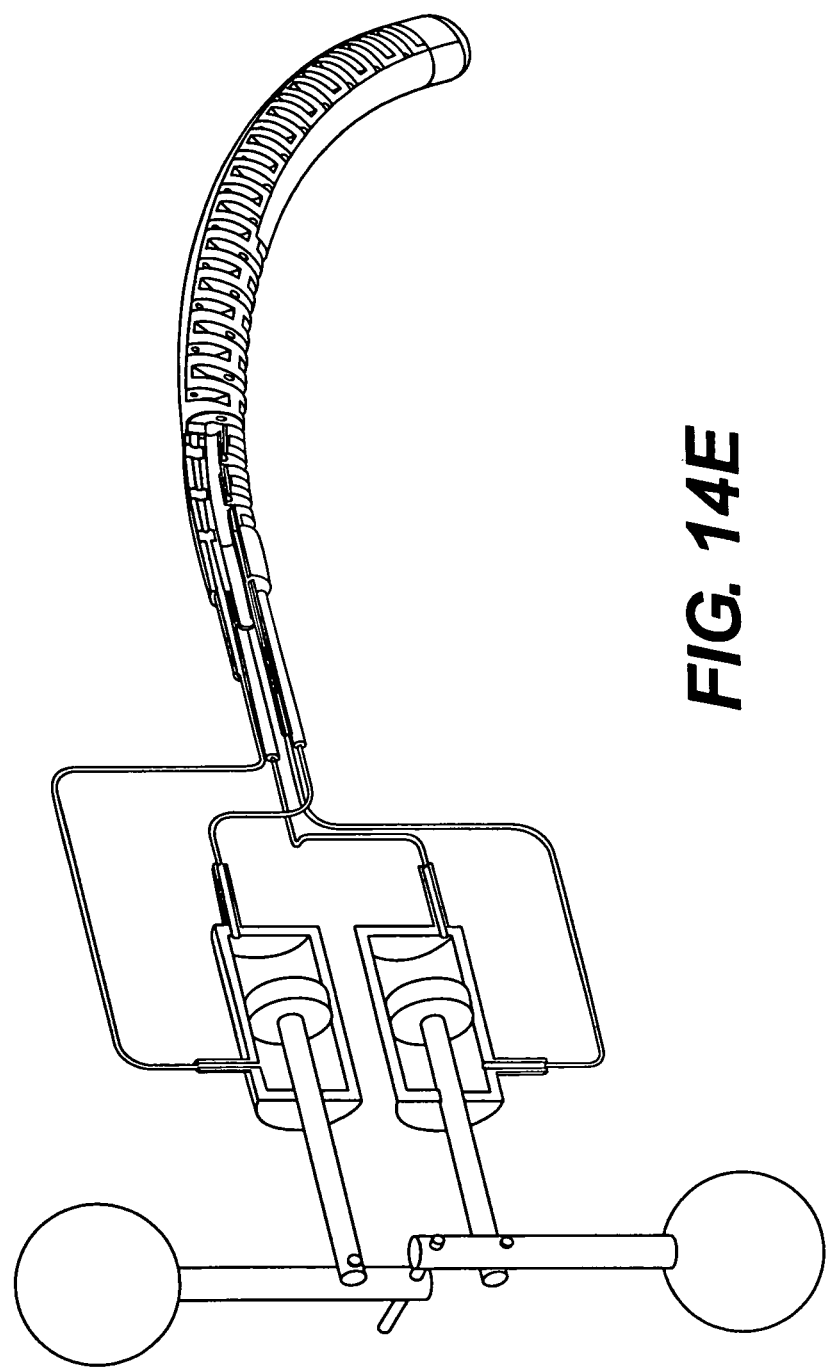

Alternatively, as illustrated in FIGS. 14C through 14E, catheter 223 can have a configuration similar to the catheter illustrated FIGS. 9A through 9D. The cut-outs 92 in catheter 223 can define a portion of fluid pathways 132*a*, 132*b*, 132*c*, 132*d* such that increasing the volume of fluid in a pathway causes the longitudinal length of the cut-out to increase. In one aspect, cut-outs 92*a*, 92*b*, 92*c*, and 9*d* are fluidly sealed. For example, as illustrated in FIG. 14C, an outer sheath 136 can enclose the body 138 of catheter 223 and cut-outs 92. When the cut-outs increase in size or volume, outer sheath 136 can stretch allow catheter 223 to bend.

In another embodiment, the shapes of inflated fluid pathways 132*a*, 132*b*, 132*c*, and 132*d* can be formed to affect the bending of the articulation section of catheter 223. As fluid fills a particular pathway, the pressure forces the articulation section of catheter 223 to conform to the shape of that fluid pathway. A user can use this embodiment to lock the catheter 223 into a particular curved shape, for example.

While catheter 222 is illustrated as having expandable fluid pathways (or cut-outs) along its whole length, in another aspect, only a portion of the catheter is articulating (i.e., the articulation section). For example, a distal portion of the catheter 223 can include cut-outs or fluidly expandable chambers or pathways to permit articulation.

One skilled in the art will appreciate that the degree of articulation (i.e., the amount of bend) can be varied depending on the amount of hydraulic pressure applied and/or on the material of catheter 223, the size of the fluid pathway, the shape of the fluid pathway, and/or the location of the fluid pathway.

Regardless of the configuration of the fluid pathways, catheter 223, like the catheters described above, can include at least one channel for the passage of at least one medical tool. For example, as illustrated in FIGS. 14B and 14C, channel 134 is positioned along the central longitudinal axis of the catheter and is surrounded by fluid pathways 132*a*, 132*b*, 132*c*, 132*d*. Channel 134 can serve as a lumen or multiple lumens in other embodiments.

Other embodiments will be apparent to those skilled in the art from consideration of the specification and practice of the embodiments disclosed herein. It is intended that the specification and examples be considered as exemplary only, with a true scope and spirit of the embodiments being indicated by the following claims.

A variety of alternative control members, which allow a distal end of tool 40 to be actuated in the up/down, right/left, forward/backward, and rotational directions, can be used with system 20. Such alternative control mechanisms are disclosed, for example, in U.S. patent application Ser. No. 11/165,593, entitled "Medical Device Control System" and U.S. patent application Ser. No. 11/474,114, entitled "Medical Device Control System," both of which are hereby incorporated by reference in their entirety.

The invention claimed is:

1. A drive system, comprising:
a first tool adapted for use by a left hand; and
a second tool adapted for use by a right hand, the second tool comprising:
a single control handle;
a housing containing a control mechanism being driven by the control handle, wherein the control handle is coupled to the housing via a shaft, an entirety of the single control handle being configured to rotate relative to the housing about a first axis defined by the shaft and a second axis different from the first axis by moving the entirety of the single control handle, wherein each of the first axis and the second axis is different from a longitudinal axis of the housing, and wherein rotating the entirety of the single control handle about the second axis causes a corresponding rotation of the shaft about the second axis;
a catheter having an end effector and an articulation section proximal to the end effector comprising a plurality of segments that pivot relative to each other via a ball and socket mechanism; and a first control cable including a proximal end and a distal end, the proximal end mating with the control mechanism and the distal end mating with the articulation section, wherein the first control cable articulates the articulation section by transferring force generated by movement of the control handle about the first axis or the second axis.

2. The drive system of claim 1, wherein the control handle includes a trigger, and the end effector is articulated by the control handle and actuated by the trigger.

3. The drive system of claim 1, further comprising a locking mechanism that inhibits rotation of the control handle about at least one of the first axis or the second axis.

4. The drive system of claim 3, wherein the locking mechanism inhibits rotation of the control handle about each of the first axis and the second axis.

5. The drive system of claim 1, wherein the control handle is coupled to a trunnion having at least one pulley.

6. The drive system of claim 5, wherein the at least one pulley is fixedly mounted to the trunnion.

7. The drive system of claim 6, wherein the trunnion includes at least one post defining the second axis.

8. The drive system of claim 1, wherein the articulation section of the catheter includes a plurality of first segments mated with a plurality of second segments, each first segment being configured to pivot relative to each second segment.

9. The drive system of claim 8, wherein a proximal surface or a distal surface of each first or second segment defines a male mating member and the other of the proximal surface or the distal surface defines a female mating member, the female mating member of each first segment having a shape complementary to the male mating member of an adjacent second segment, each first and second segment including at least one channel extending through the male mating member but not through the female mating member.

* * * * *